US010057983B1

(12) United States Patent
Etzkorn et al.

(10) Patent No.: US 10,057,983 B1
(45) Date of Patent: Aug. 21, 2018

(54) FABRICATION METHODS FOR BIO-COMPATIBLE DEVICES USING AN ETCH STOP AND/OR A COATING

(71) Applicant: Verily Life Sciences LLC, Mountain View, CA (US)

(72) Inventors: James Etzkorn, Mountain View, CA (US); Harvey Ho, San Francisco, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 572 days.

(21) Appl. No.: 14/304,650

(22) Filed: Jun. 13, 2014

(51) Int. Cl.
*H05K 3/32* (2006.01)
*H05K 1/02* (2006.01)
*H05K 3/30* (2006.01)

(52) U.S. Cl.
CPC ........... *H05K 1/0298* (2013.01); *H05K 3/303* (2013.01); *H05K 2201/20* (2013.01); *H05K 2203/0756* (2013.01); *H05K 2203/1377* (2013.01)

(58) Field of Classification Search
CPC .............. A61B 5/6832; A61B 5/14507; A61B 5/14532; A61B 5/1486; A61B 5/682; A61B 5/6821; H01L 23/291; H01L 23/3107; H05K 3/30; H05K 3/301; H05K 3/303; H05K 3/306; H05K 3/32; H05K 1/0298; H05K 2203/0756; H05K 2203/1377; H05K 2201/20; Y10T 29/49155; Y10T 29/49158
USPC ................... 29/832, 841, 840, 846
See application file for complete search history.

(56) References Cited

U.S. PATENT DOCUMENTS

| | | | | |
|---|---|---|---|---|
| 6,150,227 | A * | 11/2000 | Kinoshita | ......... H01L 21/76213 257/E21.004 |
| 6,559,905 | B1 * | 5/2003 | Akiyama | ................ H01L 24/24 257/E21.414 |
| 6,657,289 | B1 * | 12/2003 | Craig | ...................... H01L 23/13 257/678 |
| 8,258,635 | B2 * | 9/2012 | Greenberg | ............. A61N 1/375 257/788 |
| 8,501,547 | B2 | 8/2013 | Greenberg et al. | |
| 8,530,265 | B2 | 9/2013 | Fan | |
| 8,626,258 | B2 | 1/2014 | Chandrasekaran et al. | |
| 8,666,471 | B2 | 3/2014 | Rogers et al. | |
| 8,950,068 | B2 * | 2/2015 | Etzkorn | ............. A61B 5/14546 29/592.1 |

(Continued)

*Primary Examiner* — Peter DungBa Vo
*Assistant Examiner* — Kaying Kue
(74) *Attorney, Agent, or Firm* — McDonnell Boehnen Hulbert & Berghoff LLP

(57) ABSTRACT

A method may involve: forming a first bio-compatible layer; forming an etch stop over a portion of the first bio-compatible layer; forming a conductive pattern over the etch stop and the first bio-compatible layer, wherein the conductive pattern defines an antenna, sensor electrodes, electrical contacts, and one or more electrical interconnects; mounting an electronic component to the electrical contacts; forming a second bio-compatible layer over the electronic component, the antenna, the sensor electrodes, the electrical contacts, the one or more electrical interconnects, and the etch stop; and etching, using an etchant, a portion of the second bio-compatible layer to form an opening in the second bio-compatible layer and thereby expose the sensor electrodes, wherein the etch stop inhibits etching of the portion of the first bio-compatible layer by the etchant.

15 Claims, 16 Drawing Sheets

(56) References Cited

U.S. PATENT DOCUMENTS

| | | | | |
|---|---|---|---|---|
| 9,009,958 B2* | 4/2015 | Etzkorn | ................ | G02C 7/083 |
| | | | | 29/832 |
| 9,044,200 B1* | 6/2015 | Liu | ..................... | A61B 5/6832 |
| 9,101,309 B1* | 8/2015 | Liu | ..................... | A61B 5/1486 |
| 9,282,920 B2* | 3/2016 | Ho | ..................... | A61B 5/14503 |
| 9,685,689 B1* | 6/2017 | Etzkorn | ................. | H01P 11/00 |
| 9,743,885 B1* | 8/2017 | Yao | ..................... | A61B 5/6821 |
| 9,763,605 B2* | 9/2017 | Liu | ................... | A61B 5/14532 |
| 2004/0146747 A1* | 7/2004 | Nemoto | ................... | G11B 5/66 |
| | | | | 428/827 |
| 2006/0134893 A1* | 6/2006 | Savage | ............... | H01L 21/6835 |
| | | | | 438/483 |
| 2006/0252172 A1* | 11/2006 | Park | ..................... | B82Y 35/00 |
| | | | | 438/48 |
| 2007/0035717 A1* | 2/2007 | Wu | ..................... | B82Y 10/00 |
| | | | | 355/78 |
| 2009/0242925 A1* | 10/2009 | Kitagawa | ............... | H01L 33/38 |
| | | | | 257/99 |
| 2010/0200538 A1 | 8/2010 | Petisce et al. | | |
| 2010/0252840 A1* | 10/2010 | Ibbetson | ............. | H01L 25/0753 |
| | | | | 257/88 |
| 2011/0257504 A1 | 10/2011 | Hendricks et al. | | |

* cited by examiner

FABRICATION METHODS FOR BIO-COMPATIBLE DEVICES USING AN ETCH STOP AND/OR A COATING

BACKGROUND

Unless otherwise indicated herein, the materials described in this section are not prior art to the claims in this application and are not admitted to be prior art by inclusion in this section.

A body-mountable device may be configured to monitor health-related information based on at least one analyte from a user. For example, a bio-compatible device may be embedded in a polymer to provide the body-mountable device. The bio-compatible device includes a sensor configured to detect the at least one analyte (e.g., glucose) in a fluid of a user wearing the body-mountable device. The body-mountable device may also be configured to monitor various other types of health-related information.

SUMMARY

In one aspect, a method is disclosed. The method involves forming a first bio-compatible layer, wherein the first bio-compatible layer defines a first side of a bio-compatible device; forming an etch stop over a portion of the first bio-compatible layer; forming a conductive pattern over the etch stop and the first bio-compatible layer, wherein the conductive pattern defines an antenna, sensor electrodes, electrical contacts, and one or more electrical interconnects; mounting an electronic component to the electrical contacts; forming a second bio-compatible layer over the first bio-compatible layer, the electronic component, the antenna, the sensor electrodes, the electrical contacts, the one or more electrical interconnects, and the etch stop, wherein the second bio-compatible layer defines a second side of the bio-compatible device; and etching, using an etchant, a portion of the second bio-compatible layer to form an opening in the second bio-compatible layer and thereby expose the sensor electrodes, wherein the etch stop inhibits etching of the portion of the first bio-compatible layer by the etchant.

In another aspect, a device is disclosed. The device includes: a conductive pattern, wherein the conductive pattern defines an antenna, sensor electrodes, electrical contacts, and one or more electrical interconnects, and wherein the sensor electrodes are located over an etch stop; an electronic component mounted to the electrical contacts; and a bio-compatible layer over the electronic component, the antenna, the sensor electrodes, the electrical contacts, the one or more electrical interconnects, and the etch stop, wherein the bio-compatible layer defines a first side and a second side of a bio-compatible device.

In yet another aspect, a system is disclosed. The system includes: means for forming a first bio-compatible layer, wherein the first bio-compatible layer defines a first side of a bio-compatible device; means for forming an etch stop over a portion of the first bio-compatible layer; means for forming a conductive pattern over the etch stop and the first bio-compatible layer, wherein the conductive pattern defines an antenna, sensor electrodes, electrical contacts, and one or more electrical interconnects; mounting an electronic component to the electrical contacts; means for forming a second bio-compatible layer over the first bio-compatible layer, the electronic component, the antenna, the sensor electrodes, the electrical contacts, the one or more electrical interconnects, and the etch stop, wherein the second bio-compatible layer defines a second side of the bio-compatible device; and means for etching, using an etchant, a portion of the second bio-compatible layer to form an opening in the second bio-compatible layer and thereby expose the sensor electrodes, wherein the etch stop inhibits etching of the portion of the first bio-compatible layer by the etchant.

These as well as other aspects, advantages, and alternatives, will become apparent to those of ordinary skill in the art by reading the following detailed description, with reference where appropriate to the accompanying drawings.

DETAILED DESCRIPTION

The following detailed description describes various features and functions of the disclosed methods and systems with reference to the accompanying figures. In the figures, similar symbols typically identify similar components, unless context dictates otherwise. The illustrative method and system embodiments described herein are not meant to be limiting. It will be readily understood that certain aspects of the disclosed methods and systems can be arranged and combined in a wide variety of different configurations, all of which are contemplated herein.

I. Introduction

A bio-compatible device may include a first bio-compatible layer, a conductive pattern on the first bio-compatible layer, an electronic component mounted to the conductive pattern, and a second bio-compatible layer over the first bio-compatible layer, the electronic component, and the conductive pattern. The conductive pattern may define an antenna, sensor electrodes, electrical contacts, and one or more electrical interconnects. In some embodiments, the electronic component may be mounted to the electrical contacts.

When fabricating such a bio-compatible device, an etch stop may be formed over a first portion of the first bio-compatible layer. When a portion of the second bio-compatible layer is etched using an etchant to form an opening in the second bio-compatible layer and thereby expose the sensor electrodes, the etch stop may inhibit etching of the first portion of the first bio-compatible layer by the etchant.

Further, when fabricating such bio-compatible device, a coating may be formed over at least a portion of the first bio-compatible layer, at least a portion of the conductive pattern, and/or at least a portion of the bio-compatible device. The coating may help to protect the bio-compatible device from moisture.

Beneficially, embodiments described herein can be used in scenarios in which the body-mountable device comprises a variety of mountable devices that are mounted on or in portions of the human body. In addition, the fabrication methods described herein may allow the fabricated bio-compatible devices to perform one or more functions while submerged in a fluid.

II. Example Systems and Devices

An example body-mountable device that comprises an eye-mountable device that is configured to detect at least one analyte in a tear film of a user wearing the eye-mountable device will now be described in greater detail.

Figure 1:
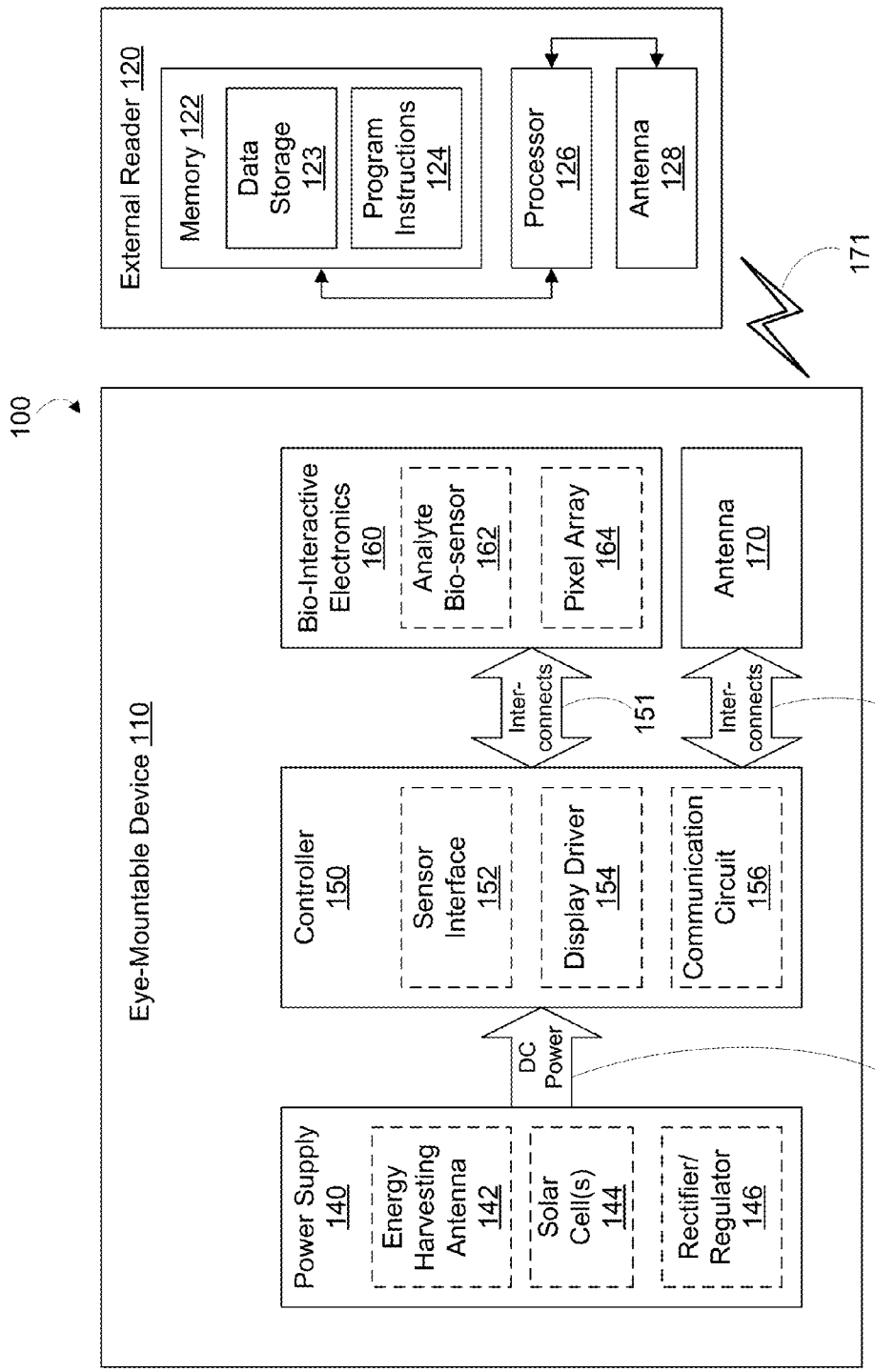
FIG. 1 is a block diagram of a system with an eye-mountable device in wireless communication with an external reader, according to an example embodiment.

FIG. 1 is a block diagram of a system 100 with an eye-mountable device 110 in wireless communication with an external reader 120. The exposed regions of the eye-mountable device 110 are made of a polymeric material that may be formed for mounting to a corneal surface of an eye and in which a structure is at least partially embedded. The structure may include a power supply 140, a controller 150, bio-interactive electronics 160, and an antenna 170.

In some embodiments, the structure may be a bio-compatible device in which some or all of the components formed or mounted thereon are encapsulated by a bio-compatible material.

In some example embodiments, the structure may be positioned away from the center of the eye-mountable device 110 and thereby avoid interference with light transmission to the central, light-sensitive region of the eye. For example, where the eye-mountable device 110 is shaped as a curved disk, the structure may be embedded around the periphery (e.g., near the outer circumference) of the disk. In other example embodiments, the structure may be positioned in or near the central region of the eye-mountable device 110. For example, portions of the structure may be substantially transparent to incoming visible light to mitigate interference with light transmission to the eye. Moreover, in some embodiments, the bio-interactive electronics 160 may include a pixel array 164 that emits and/or transmits light to be received by the eye according to display instructions. Thus, the bio-interactive electronics 160 may optionally be positioned in the center of the eye-mountable device so as to generate visual cues perceivable to a wearer of the eye-mountable device 110, such as displaying information (e.g., characters, symbols, flashing patterns, etc.) on the pixel array 164.

The power supply 140 is configured to harvest ambient energy to power the controller 150 and bio-interactive electronics 160, and may include an energy harvesting antenna 142 and/or solar cells 144. The energy harvesting antenna 142 may capture energy from incident radio radiation. The solar cells 144 may comprise photovoltaic cells configured to capture energy from incoming ultraviolet, visible, and/or infrared radiation.

A rectifier/regulator 146 may be used to condition the captured energy to a stable DC supply voltage 141 at a level suitable for operating the controller, and then supply the voltage to the controller 150. The rectifier/regulator 146 may include one or more energy storage devices to mitigate high frequency variations in the energy harvesting antenna 142 and/or solar cell(s) 144. For example, one or more energy storage devices (e.g., a capacitor or an inductor) may be connected in parallel across the outputs of the rectifier/regulator 146 to regulate the DC supply voltage 141 and may be configured to function as a low-pass filter.

The controller 150 is configured to execute instructions to operate the bio-interactive electronics 160 and the antenna 170. The controller 150 includes logic circuitry configured to operate the bio-interactive electronics 160 so as to interact with a biological environment of the eye-mountable device 110. The interaction could involve the use of one or more components, such an analyte bio-sensor 162 in the bio-interactive electronics 160, to obtain input from the biological environment. Additionally or alternatively, the interaction could involve the use of one or more components, such as a pixel array 164, to provide an output to the biological environment.

In one example, the controller 150 includes a sensor interface module 152 that is configured to operate the analyte bio-sensor 162. The analyte bio-sensor 162 may be, for example, an amperometric electrochemical sensor that includes a working electrode and a reference electrode driven by a sensor interface. A voltage is applied between the working and reference electrodes to cause an analyte to undergo an electrochemical reaction (e.g., a reduction and/or oxidation reaction) at the working electrode. The electrochemical reaction generates an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent may also be included to sensitize the electrochemical sensor to one or more desired analytes. For example, a layer of glucose oxidase ("GOX") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

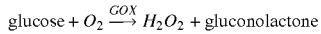

$$\text{glucose} + O_2 \xrightarrow{GOX} H_2O_2 + \text{gluconolactone}$$

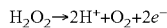

$$H_2O_2 \rightarrow 2H^+ + O_2 + 2e^-$$

The current generated by either reduction or oxidation reactions can be approximately proportionate to the reaction rate. Further, the reaction rate can be dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current can thus provide an indication of the analyte concentration.

The controller 150 can optionally include a display driver module 154 for operating the pixel array 164. The pixel array 164 can be array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 may include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 120. For example, the communication circuit 156 can cause variations in the amplitude, phase, and/or frequency of backscatter radiation from the antenna 170, and such variations may then be detected by the reader 120.

The controller 150 is connected to the bio-interactive electronics 160 via interconnects 151. Similarly, the controller 150 is connected to the antenna 170 via interconnects 157. The interconnects 151, 157 may comprise a patterned conductive material (e.g., gold, platinum, palladium, titanium, copper, aluminum, silver, metals, any combinations of these, etc.).

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical feature. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided on a chip by rectifier and/or regulator components of the same chip. That is, the functional blocks in FIG. 1 shown as the power supply block 140 and controller block 150 need not be implemented as separated modules. Moreover, one or more of the functional modules described in FIG. 1 can be implemented by separately packaged chips electrically connected to one another.

Additionally or alternatively, the energy harvesting antenna 142 and the antenna 170 can be implemented with the same, physical antenna. For example, a loop antenna can both harvest incident radiation for power generation and communicate information via backscatter radiation.

The external reader 120 includes an antenna 128 (or group of more than one antennae) to send and receive wireless signals 171 to and from the eye-mountable device 110. The external reader 120 also includes a computing system with a processor 126 in communication with a memory 122. The memory 122 is a non-transitory computer-readable medium that can include, without limitation, magnetic disks, optical disks, organic memory, and/or any other volatile (e.g., RAM) or non-volatile (e.g., ROM) storage system readable by the processor 126. The memory 122 can include a data storage 123 to store indications of data, such as sensor readings (e.g., from the analyte bio-sensor 162), program settings (e.g., to adjust behavior of the eye-mountable device 110 and/or external reader 120), etc. The memory 122 can also include program instructions 124 for execution by the processor 126 to cause the external reader 120 to perform processes specified by the program instructions. For example, the program instructions 124 may cause the external reader 120 to provide a user interface that allows for retrieving information communicated from the eye-mountable device 110 (e.g., sensor outputs from the analyte bio-sensor 162). The external reader 120 can also include one or more hardware components for operating the antenna 128 to send and receive the wireless signals 171 to and from the eye-mountable device 110. For example, oscillators, frequency injectors, encoders, decoders, amplifiers, and filters can drive the antenna 128 according to instructions from the processor 126.

The external reader 120 may be a smart phone, digital assistant, or other portable computing device with wireless connectivity sufficient to provide the wireless communication link 171. The external reader 120 can also be implemented as an antenna module that can be plugged in to a portable computing device, such as in an example where the communication link 171 operates at carrier frequencies not commonly employed in portable computing devices. In some instances, the external reader 120 is a special-purpose device configured to be worn relatively near a wearer's eye to allow the wireless communication link 171 to operate using with a low power budget. For example, the external reader 120 can be integrated in eyeglasses, integrated in a piece of jewelry such as a necklace, earing, etc., or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. To perform a reading with the system 100 configured as a tear film analyte monitor, the external reader 120 can emit radio frequency radiation 171 that is harvested to power the eye-mountable device 110 via the power supply 140. Radio frequency electrical signals captured by the energy harvesting antenna 142 (and/or the antenna 170) are rectified and/or regulated in the rectifier/regulator 146 and a regulated DC supply voltage 141 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode can be measured to provide the sensor output indicative of the analyte concentration. The controller 150 can operate the antenna 170 to communicate the sensor results back to the external reader 120 (e.g., via the communication circuit 156). The sensor result can be communicated by, for example, modulating an impedance of the antenna 170 such that the modulation in impedance is detected by the external reader 120. The modulation in antenna impedance can be detected by, for example, backscatter radiation from the antenna 170.

In some embodiments, the system 100 can operate to non-continuously ("intermittently") supply energy to the eye-mountable device 110 to power the on-board controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to charge two electrodes to a potential sufficient to induce electrochemical reactions measure the resulting amperometric current, and modulate the antenna impedance to adjust the backscatter radiation in a manner indicative of the measured current. In such an example, the supplied radio frequency radiation 171 can be considered an interrogation signal from the external reader 120 to the eye-mountable device 110 to request a measurement. By periodically interrogating the eye-mountable device 110 (e.g., by supplying radio frequency radiation 171 to temporarily turn the device on) and storing the sensor results (e.g., via the data storage 123), the external reader 120 can accumulate a set of analyte concentration measurements over time without continuously powering the eye-mountable device 110.

Figure 2A:
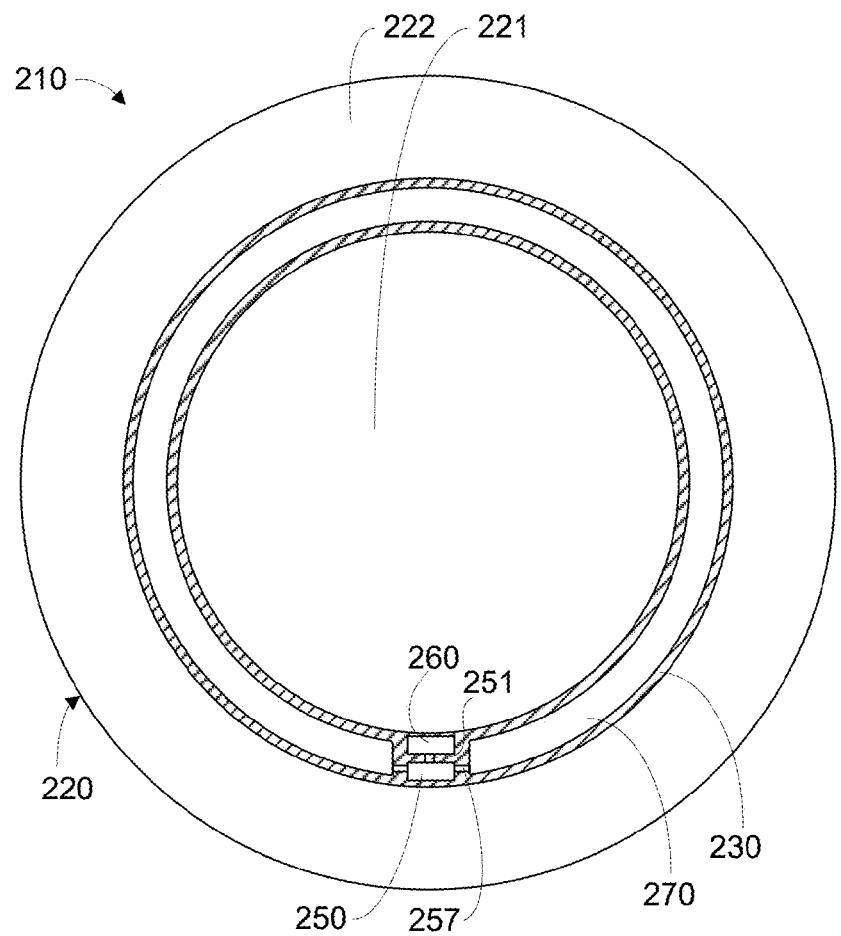
FIG. 2a is a top view of an eye-mountable device, according to an example embodiment.
Figure 2B:
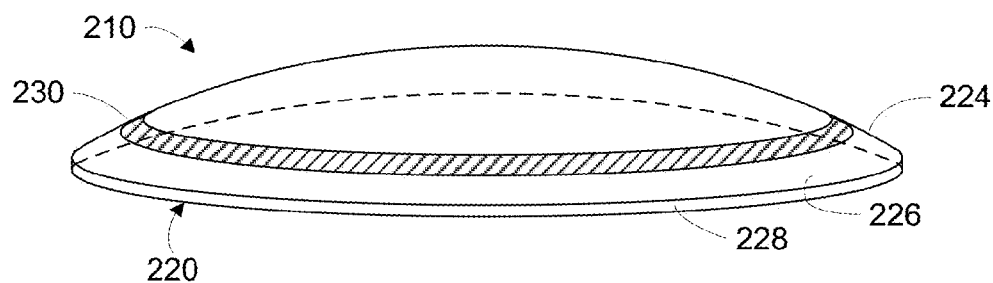
FIG. 2b is a side view of an eye-mountable device, according to an example embodiment.

FIG. 2a is a top view of an eye-mountable device 210. FIG. 2b is a side view of the eye-mountable device shown in FIG. 2a. It is noted that relative dimensions in FIGS. 2a and 2b are not necessarily to scale, but have been rendered for purposes of explanation only in describing the arrangement of the eye-mountable device 210.

The eye-mountable device 210 is formed of a polymeric material 220, shaped as a curved disk. The polymeric material 220 can be a substantially transparent material to allow incident light to be transmitted to the eye while the eye-mountable device 210 is mounted to the eye. The polymeric material 220 can be a bio-compatible material similar to those employed to form vision correction and/or cosmetic contact lenses in optometry, such as polyethylene terephthalate ("PET"), polymethyl methacrylate ("PMMA"), silicone hydrogels, and combinations of these. The polymeric material 220 can be formed with a concave surface 226 suitable to fit over to a corneal surface of an eye. The opposing side of the disk can have a convex surface 224 that does not interfere with eye-lid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface and/or the scleral surface of the wearer's eye.

While the eye-mountable device 210 is mounted in an eye, the convex surface 224 (i.e., the anterior surface) faces outward to the ambient environment while the concave surface 226 (i.e., the posterior surface) faces inward, toward the corneal surface. The convex surface 224 can therefore be considered an outer, top surface of the eye-mountable device 210 whereas the concave surface 226 can be considered an inner, bottom surface. The "top" view shown in FIG. 2a is facing the convex surface 224.

A structure (or substrate) 230 is embedded in the polymeric material 220. The structure 230 can be embedded to be situated near or along an outer periphery 222 of the polymeric material, away from the central region 221. The structure 230 does not interfere with vision because it is too close to the eye to be in focus and is positioned away from the central region 221 where incident light is transmitted to the light-sensing portions of the eye. Moreover, the structure 230 can be formed of a transparent material to further mitigate any effects on visual perception.

The structure 230 can be shaped as a flat, circular ring (e.g., a disk with a centered hole). The flat surface of the structure 230 (e.g., along the radial width) is a platform for mounting electronics such as chips (e.g., via flip-chip mounting) and for patterning conductive materials (e.g., via deposition techniques) to form electrodes, antenna(e), and/or connections. The structure 230 and the polymeric material 220 can be approximately cylindrically symmetric about a common central axis. The structure 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only. The structure 230 can be implanted in a variety of different form factors.

A loop antenna 270, a controller 250, and bio-interactive electronics 260 are disposed on the embedded structure 230. The controller 250 may be a chip including logic elements configured to operate the bio-interactive electronics 260 and the loop antenna 270. The controller 250 is electrically connected to the loop antenna 270 by interconnects 257 also situated on the structure 230. Similarly, the controller 250 is electrically connected to the bio-interactive electronics 260 by interconnects 251. The interconnects 251, 257, the loop antenna 270, and any conductive electrodes (e.g., for an electrochemical analyte bio-sensor, etc.) may be formed from any type of conductive material and may be patterned by a process for precisely patterning such materials, such as deposition or lithography. The conductive materials patterned on the structure 230 can be, for example, gold, platinum, palladium, titanium, carbon, aluminum, copper, silver, silver-chloride, conductors formed from noble materials, metals, or any combinations of these materials. Other materials may also be envisioned.

Figure 2D:
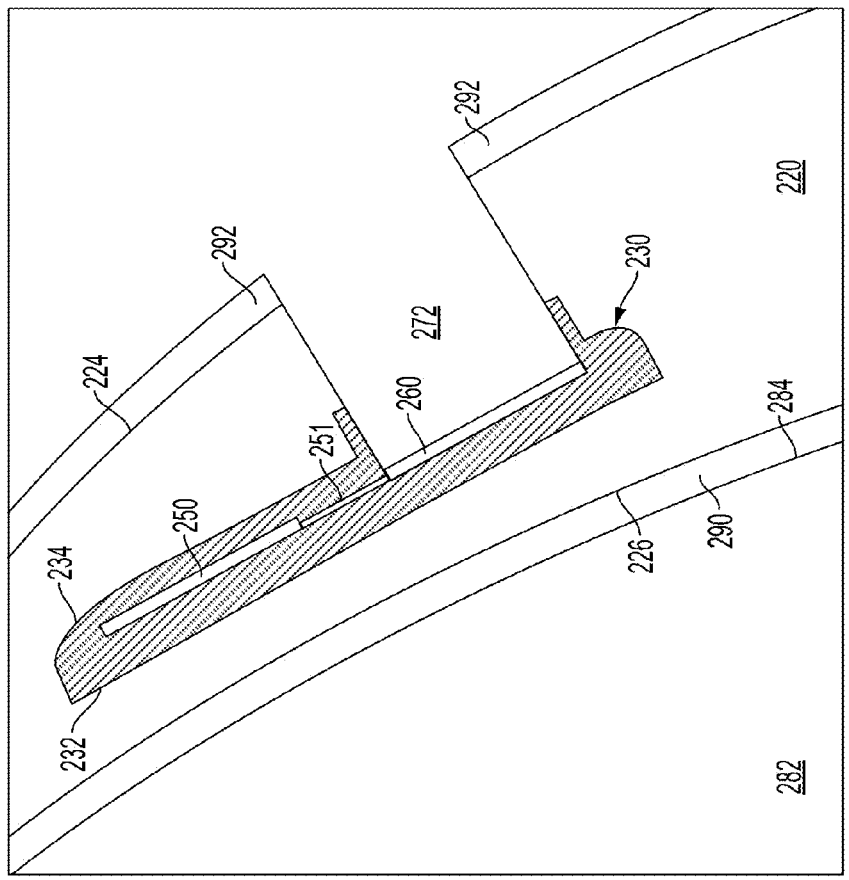
FIG. 2d is a side cross-section view showing the tear film layers surrounding the surfaces of the eye-mountable device mounted as shown in FIG. 2c, according to an example embodiment.

With reference to FIG. 2a, which is a view facing the convex surface 224 of the eye-mountable device 210, the bio-interactive electronic 260 is mounted to a side of structure 230 facing the convex surface 224. Where the bio-interactive electronics module 260 includes an analyte bio-sensor, for example, mounting such a bio-sensor on the structure 230 facing the convex surface 224 allows the bio-sensor to receive analyte concentrations in tear film through a channel 272 in the polymeric material 220 to the convex surface 224 (as illustrated in FIGS. 2c and 2d).

The loop antenna 270 is a layer of conductive material patterned along the flat surface of the structure 230 to form a flat conductive ring. In some example embodiments, the loop antenna 270 can be formed without making a complete loop. For example, the loop antenna 270 may include a cutout to allow room for the controller 250 and bio-interactive electronics 260, as illustrated in FIG. 2a. However, the loop antenna 270 can be arranged as a continuous strip of conductive material that wraps entirely around the flat surface of the structure 230 one or more times. For example, a strip of conductive material with multiple windings can be patterned on the side of the substrate 230 opposite the controller 250, the battery 255, and the bio-interactive electronics 260. Interconnects between the ends of such a wound antenna (e.g., the antenna leads) can be passed through the structure 230 to the controller 250. In some embodiments, the loop antenna can include a plurality of conductive loops spaced apart from each other, such as three conductive loops, five conductive loops, nine conductive loops, etc. With such an arrangement, the polymeric material 220 may extend between adjacent conductive loops in the plurality of conductive loops.

Figure 2C:
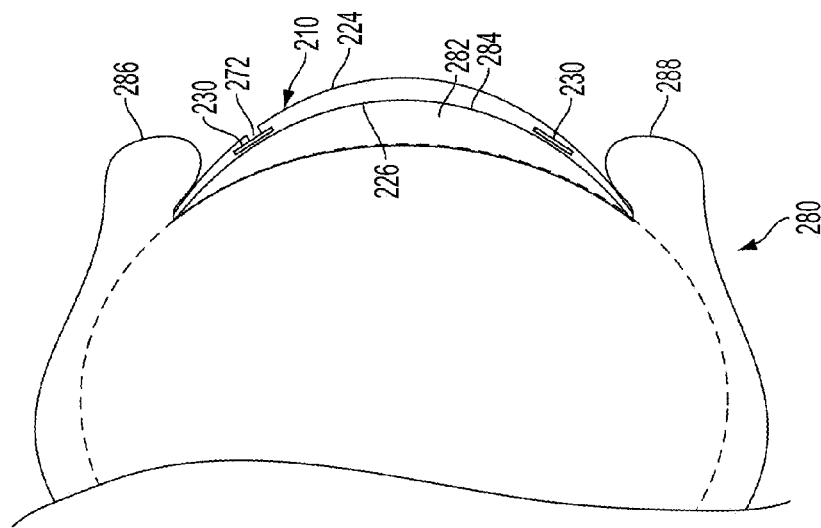
FIG. 2c is a side cross-section view of the eye-mountable device of FIG. 2a while mounted to a corneal surface of the eye, according to an example embodiment.

FIG. 2c is a side cross-section view of the eye-mountable electronic device 210 mounted to a corneal surface 284 of an eye 280. FIG. 2d is a close-in side view enhanced to show tear film layers 290, 292 surrounding the exposed surfaces 224, 226 of the eye-mountable device 210. It is noted that relative dimensions in FIGS. 2c and 2d are not necessarily to scale, but have been rendered for purposes of explanation only in describing the arrangement of the eye-mountable device 210. For example, the total thickness of the eye-mountable device 210 can be about 200 micrometers, while the thickness of the tear film layers 290, 292 can each be about 10 micrometers, although this ratio may not be reflected in the drawings. Some aspects are exaggerated to allow for illustration and facilitate explanation.

The eye 280 includes a cornea 282 that is covered by bringing the upper eyelid 286 and lower eyelid 288 together over the top of the eye 280. Incident light is received by the eye 280 through the cornea 282, where light is optically directed to light sensing elements of the eye 280 (e.g., rods and cones, etc.) to stimulate visual perception. The motion of eyelids 286, 288 distributes a tear film across the exposed corneal surface 284 of the eye 280. The tear film is an aqueous solution secreted by the lacrimal gland to protect and lubricate the eye 280. When the eye-mountable device 210 is mounted in the eye 280, the tear film coats both the convex and concave surfaces 224, 226, with an inner layer 290 (along the concave surface 226) and an outer layer 292 (along the convex surface 224). The tear film layers 290, 292 can be about 10 micrometers in thickness and together account for about 10 microliters.

The tear film layers 290, 292 are distributed across the corneal surface 284 and/or the convex surface 224 by motion of the eyelids 286, 288. For example, the eyelids 286, 288 raise and lower, respectively, to spread a small volume of tear film across the corneal surface 284 and/or the convex surface 224 of the eye-mountable device 210. The tear film layer 290 on the corneal surface 284 also facilitates mounting the eye-mountable device 210 by capillary forces between the concave surface 226 and the corneal surface 284. In some embodiments, the eye-mountable device 210 can also be held over the eye 280 in part by vacuum forces against the corneal surface 284 due to the concave curvature of the eye-facing concave surface 226.

As shown in the cross-sectional views in FIGS. 2c and 2d, the structure 230 can be inclined such that the flat mounting surfaces of the structure 230 are approximately parallel to the adjacent portion of the convex surface 224. As described above, the structure 230 is a flattened ring with an inward-facing surface 232 (facing the concave surface 226 of the polymeric material 220) and an outward-facing surface 234 (closer to the convex surface 224). The structure 230 can include electronic components and/or patterned conductive materials mounted to either or both mounting surfaces 232, 234.

As shown in FIG. 2d, the bio-interactive electronics 260, the controller 250, and the conductive interconnect 251 are located between the outward-facing surface 234 and the inward-facing surface 232 such that the bio-interactive electronics 260 are facing the convex surface 224. As described above, the polymer layer defining the anterior side may be greater than 50 micrometers thick, whereas the polymer layer defining the posterior side may be less than 150 micrometers. Thus, the bio-interactive electronics 260 may be at least 50 micrometers away from the convex surface 224 and may be a greater distance away from the concave surface 226. However, in other examples, the bio-interactive electronics 260 may be mounted on the inward-facing surface 232 of the substrate 230 such that the bio-interactive electronics 260 are facing the concave surface 226. The bio-interactive electronics 260 could also be positioned closer to the concave surface 226 than the convex surface 224. With this arrangement, the bio-interactive electronics 260 can receive analyte concentrations in the tear film 292 through the channel 272.

While the body-mountable device has been described as comprising the eye-mountable device 110 and/or the eye-mountable device 210, the body-mountable device could comprise other mountable devices that are mounted on or in other portions of the human body.

For example, in some embodiments, the body-mountable device may comprise a tooth-mountable device. In some embodiments, the tooth-mountable device may take the form of or be similar in form to the eye-mountable device 110 and/or the eye-mountable device 210. For instance, the tooth-mountable device could include a polymeric material and/or polymer that is the same as or similar to any of the polymeric materials or polymers described herein and a structure that is the same as or similar to any of the structures described herein. With such an arrangement, the tooth-mountable device may be configured to detect at least one analyte in a fluid (e.g., saliva) of a user wearing the tooth-mountable device.

Moreover, in some embodiments, the body-mountable device may comprise a skin-mountable device. In some embodiments, the skin-mountable device may take the form of or be similar in form to the eye-mountable device 110 and/or the eye-mountable device 210. For instance, the skin-mountable device could include a polymeric material and/or polymer that is the same as or similar to any of the polymeric materials described herein and a structure that is the same as or similar to any of the structures described herein. With such an arrangement, the skin-mountable device may be configured to detect at least one analyte in a fluid (e.g., perspiration, blood, etc.) of a user wearing the skin-mountable device.

Further, some embodiments may include privacy controls which may be automatically implemented or controlled by the wearer of a body-mountable device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a body-mountable device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

III. Example Methods

Figure 3A:
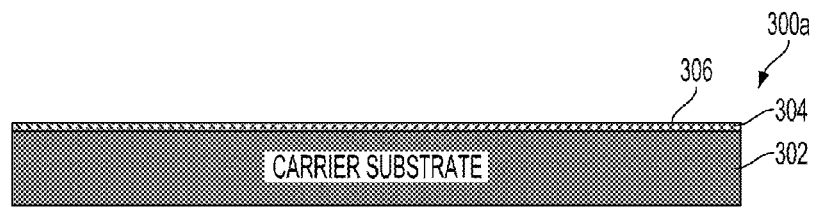
FIGS. 3a-t show stages of fabricating a bio-compatible device, according to an example embodiment.
Figure 3B:
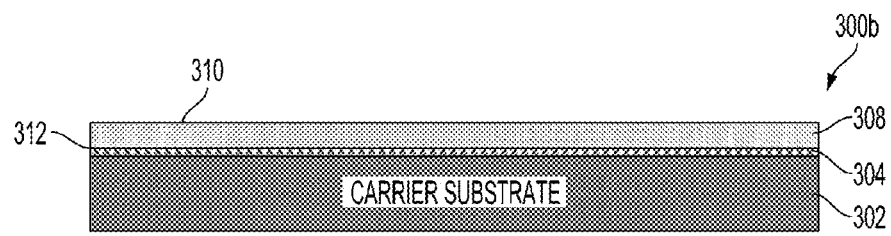
Figure 3C:
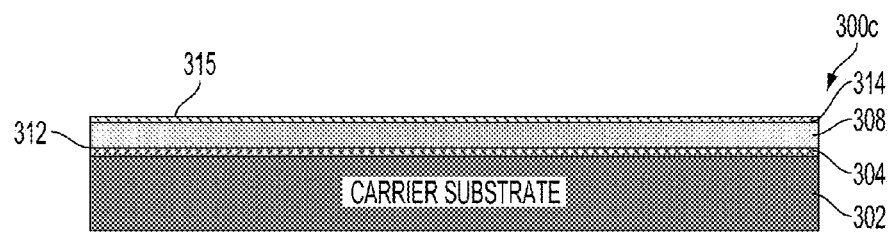
Figure 3D:
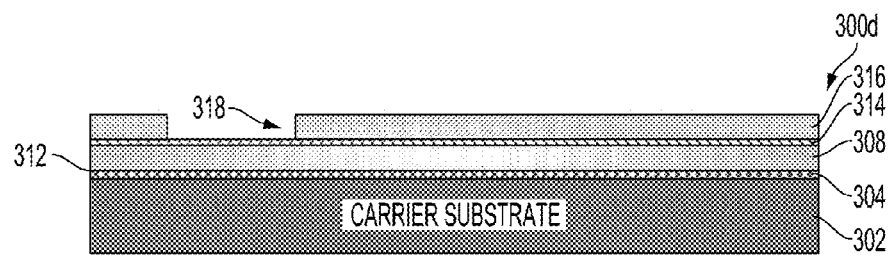
Figure 3E:
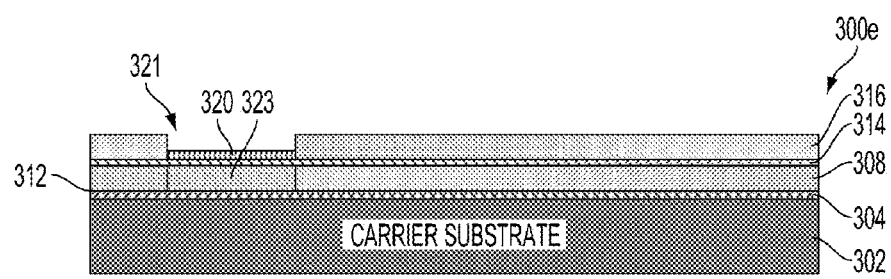
Figure 3F:
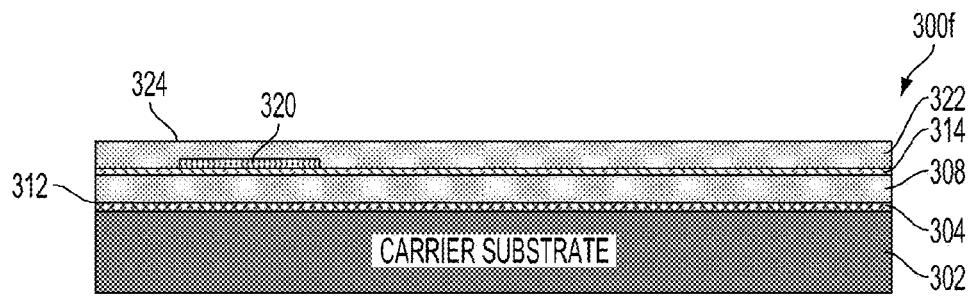
Figure 3G:
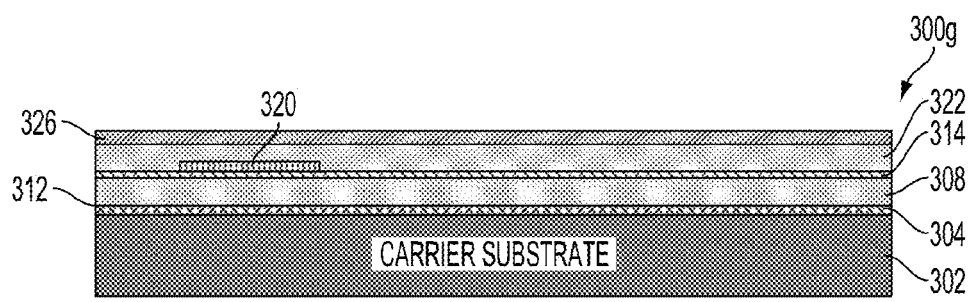
Figure 3H:
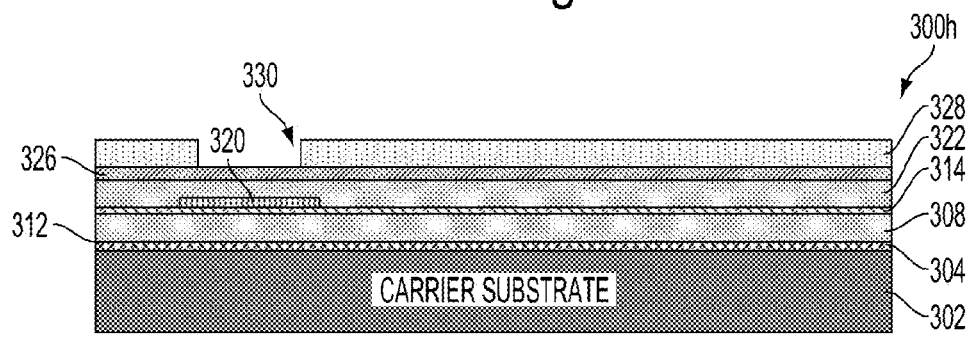
Figure 3I:
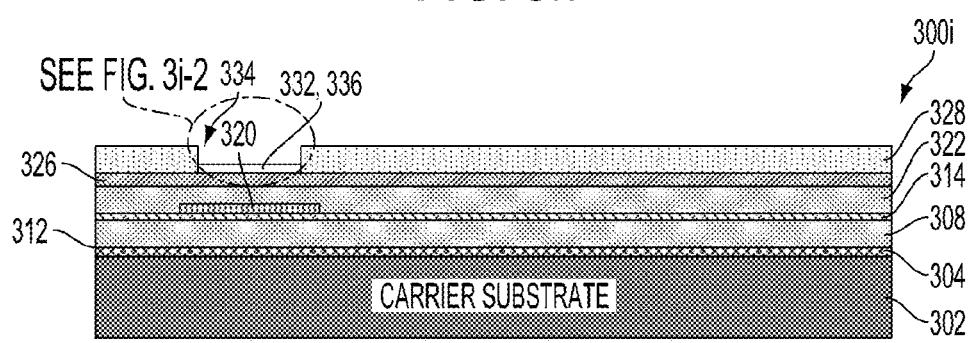
Figures 2, 3I:
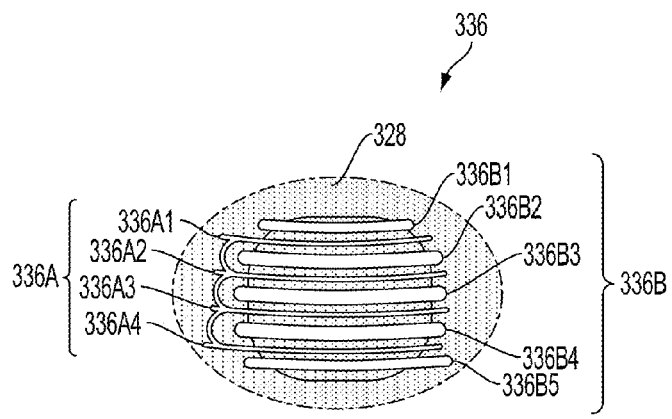
Figure 3J:
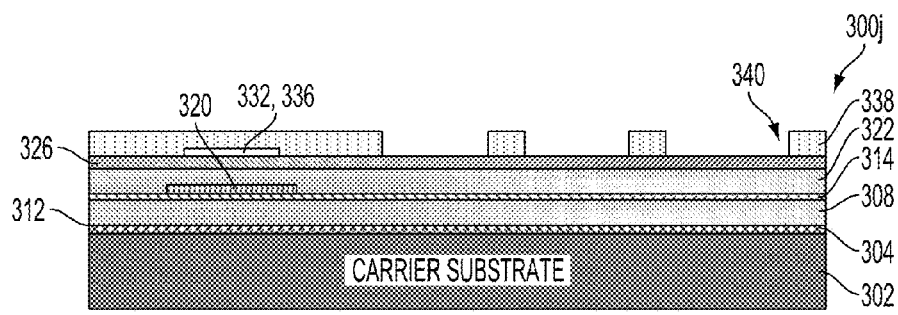
Figure 3K:
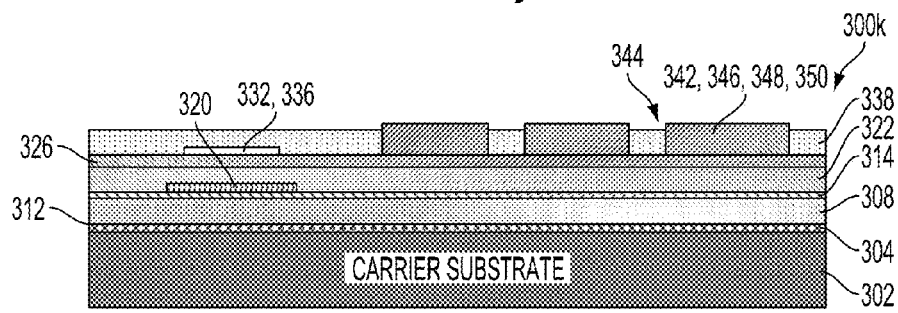
Figure 3L:
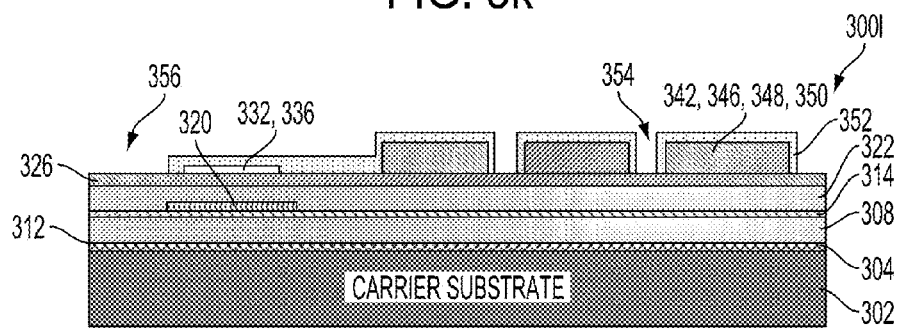
Figure 3M:
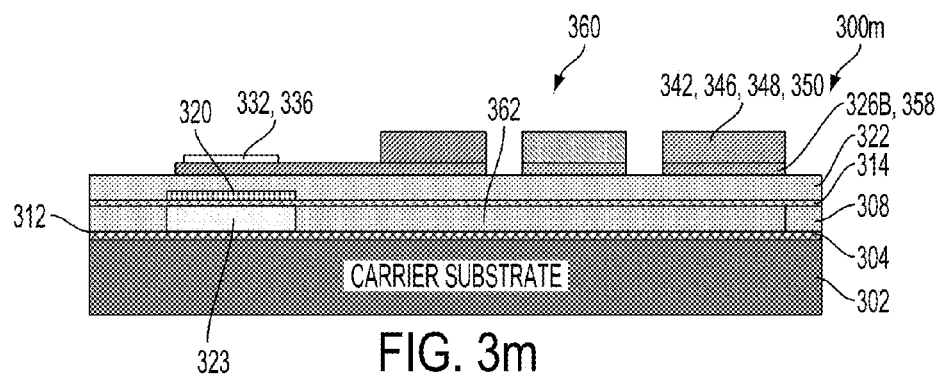
Figure 3N:
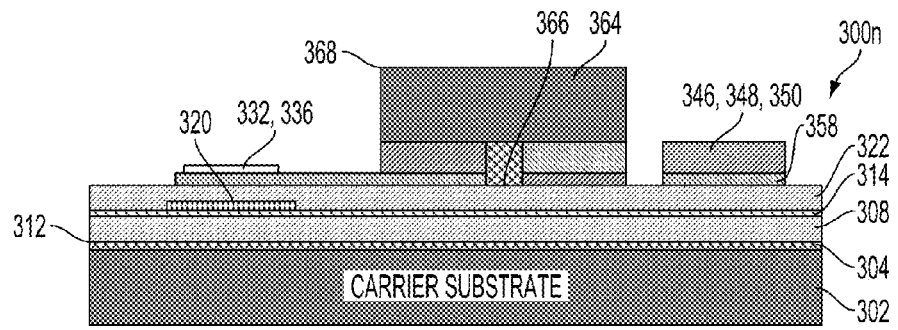
Figure 3O:
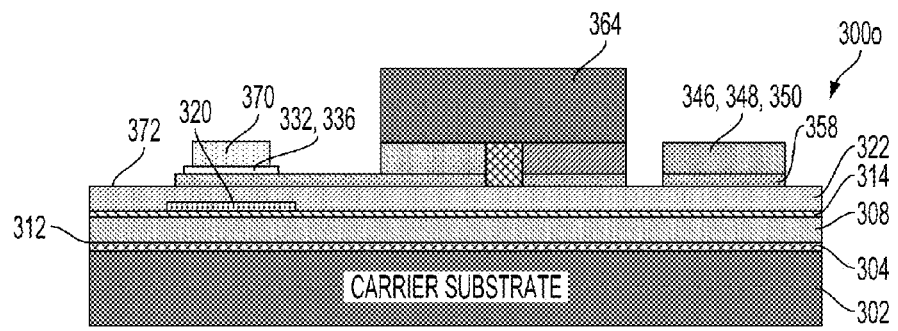
Figure 3P:
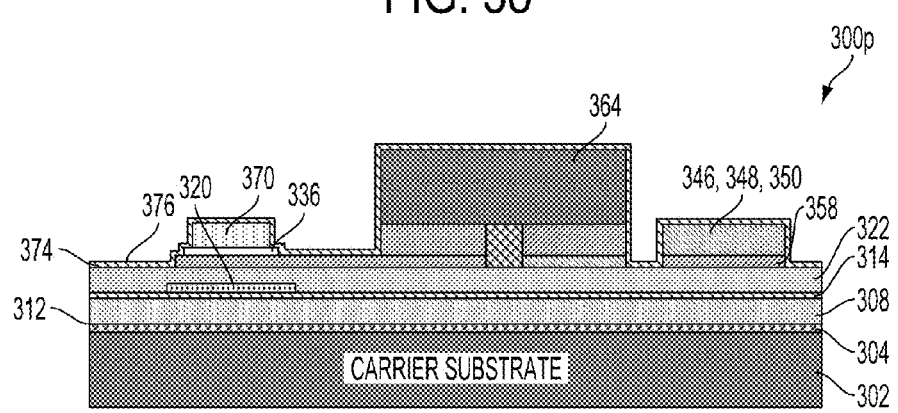
Figure 3Q:
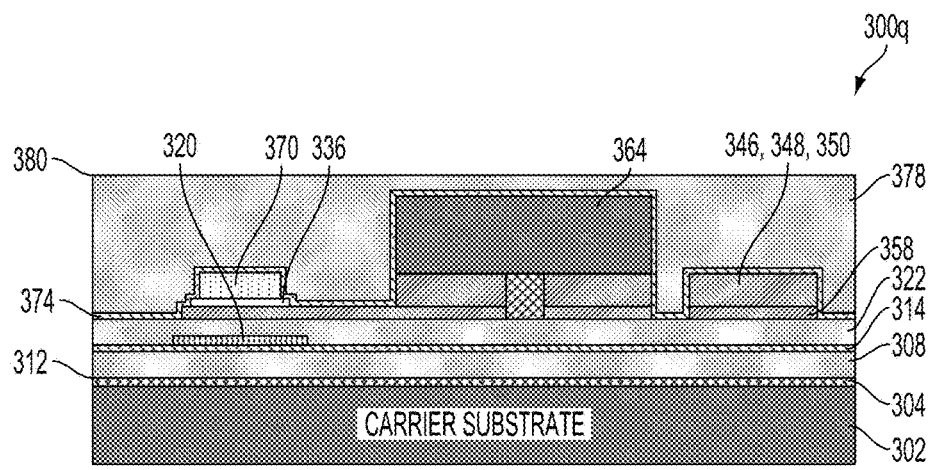
Figure 3R:
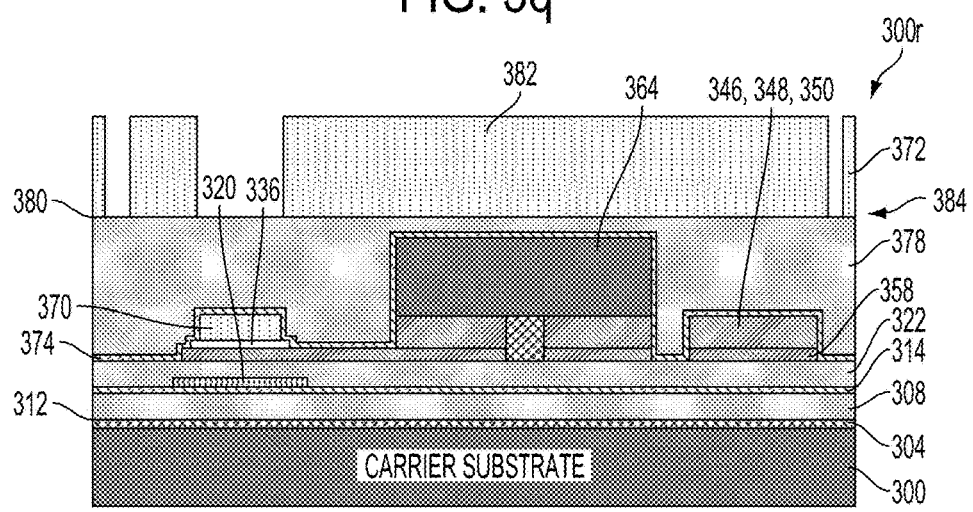
Figure 3S:
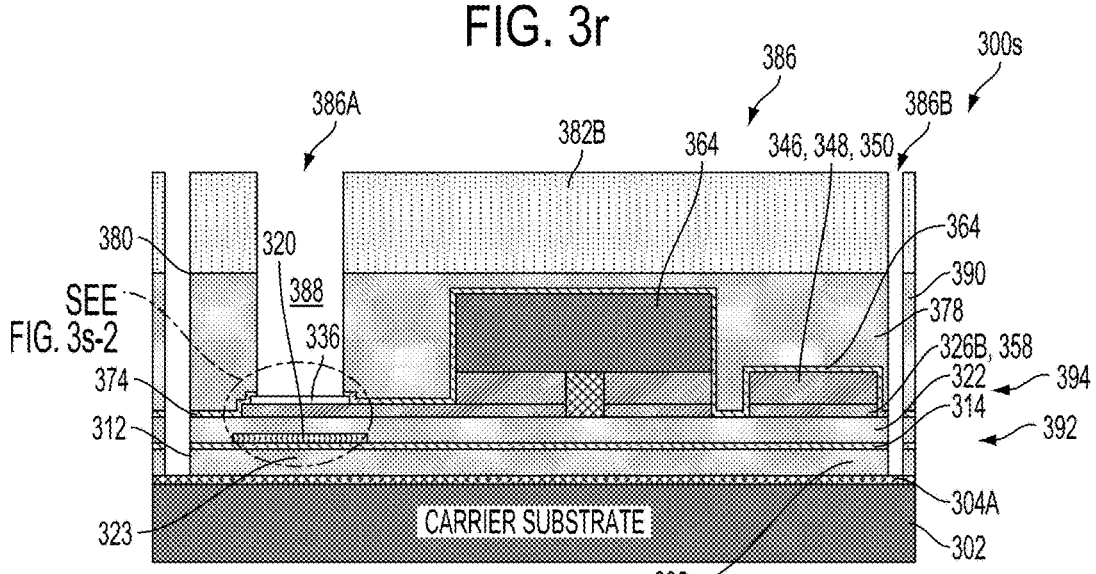
Figures 2, 3S:
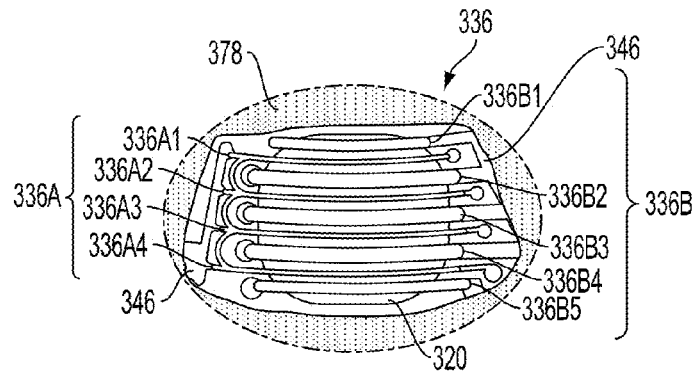
Figure 3T:
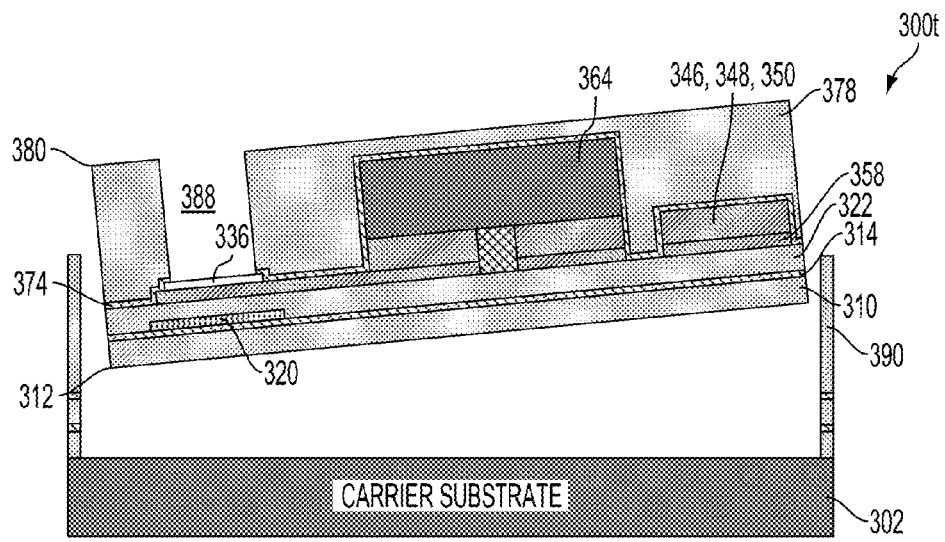

FIGS. 3a-t illustrate stages in a process for fabricating a bio-compatible device, such as a bio-compatible device 300t shown in FIG. 3t. The illustrations shown in FIGS. 3a-t are generally shown in cross-sectional views to illustrate sequentially formed layers developed to create the bio-compatible device. The layers can be developed by microfabrication and/or manufacturing techniques such as, for example, electroplating, photolithography, deposition, and/or evaporation fabrication processes and the like. The various materials may be formed according to patterns using photoresists and/or masks to pattern materials in particular arrangements, such as to form wires, electrodes, electrical contacts, etc. Additionally, electroplating techniques may also be employed to coat an arrangement of electrodes with a metallic plating. For example, an arrangement of conductive material formed by a deposition and/or photolithography process can be plated with a metallic material to create a conductive structure with a desired thickness. However, the dimensions, including relative thicknesses and widths, of the various layers illustrated and described in connection with FIGS. 3a-t to create a bio-compatible device are not illustrated to scale. Instead, the drawings in FIGS. 3a-t schematically illustrate the ordering of the various layers for purposes of explanation only.

FIG. 3a illustrates a carrier substrate 302 with a sacrificial layer 304 formed on the carrier substrate 302 to provide a partially-fabricated device 300a. The sacrificial layer 304 may have a surface 306.

The carrier substrate 302 may be any flat surface on which the layers of the encapsulated electronics structure can be assembled. For example, the carrier substrate 302 may be a wafer (e.g., a silicon wafer) similar to those used in the fabrication of semiconductor devices and/or microelectronics.

In some embodiments, the sacrificial layer 304 may adhere to the carrier substrate 302. Moreover, in some embodiments, the sacrificial layer 304 may bond with a bio-compatible layer formed on the sacrificial layer 304. With this arrangement, the bio-compatible layer formed on the sacrificial layer 304 may adhere to the sacrificial layer 304.

The sacrificial layer 304 may include a variety of materials. For example, the sacrificial layer 304 may include one or more metal layers, one or more polymer layers, and/or more or more inorganic layers. In addition, the sacrificial layer 304 may include one or more layers of a heat or an ultraviolet release film.

In some examples, the one or more metal layers of the sacrificial layer 304 may include aluminum, titanium, chromium, gold, nickel, and/or magnesium. And in at least one such example, the sacrificial layer 304 may include one metal layer that includes chromium or aluminum. In addition, the one or more metal layers may include one or more natural oxide layers that forms on at least one metal layer of the one or more metal layers. Further, in some examples, the one or more polymer layers of the sacrificial layer 304 may include a variety of polymers that can be dissolved in a solvent, acid, or base. For example, the one or more polymer layers may include a photoresist layer comprising polymethyl methacrylate ("PMMA") and/or 2-ethoxyethyl acetate. In such an example, the one or more polymer layers may be any AZ4000 series photoresist sold by Capital Scientific, such as AZ4620®. Further still, in some examples, the one or more inorganic layers of the sacrificial layer 304 may include aluminum oxide, silicon oxide, and silicon nitride.

Moreover, the sacrificial layer 304 may have a variety of thicknesses. For example, the sacrificial layer 304 may have a thickness between 10 nanometers to 2 micrometers, such as 10, 100, or 1000 nanometers. Further, in an example, the sacrificial layer 304 may be formed by a microfabrication process such as sputtering or evaporation.

Further, the carrier substrate 302 may be baked before forming the sacrificial layer 304. The carrier substrate 302 may be baked in a variety of ways. For example, the carrier substrate 302 may be baked at a temperature for a time period. In some embodiments, the temperature may be 90 degrees Celsius (C). Moreover, in some embodiments, the time period may be 2 minutes.

Further still, the carrier substrate 302 may be plasma cleaned before forming the sacrificial layer 304. The carrier substrate 302 may be plasma cleaned in a variety of ways. For example, the carrier substrate 302 may be plasma cleaned at a power for a time period. In some embodiments, the power may be high. Moreover, in some embodiments, the time period may be 2 minutes.

Moreover, a surface of the carrier substrate 302 may be treated, such that the sacrificial layer 304 bonds to the treated surface during formation of the sacrificial layer 304. The surface of the carrier substrate 302 may be treated in a variety of ways. For example, the surface may be treated by sputtering etching using an etchant at a power for a time period. In some embodiments, the etchant may include an argon plasma and/or an oxygen plasma. Moreover, in some embodiments, the power may be between 100 to 200 Watts (W). Further, in some embodiments, the time period may be between 1 to 2 minutes. In some examples, the etchant may unevenly etch the surface of the carrier substrate 302, such that the surface may be roughened. Other plasmas and/or types of plasmas may be used as well, such as plasma asher, a reactive ion etcher, etc.

As shown in FIG. 3b, a first bio-compatible layer 308 is formed on the sacrificial layer 304 to provide a partially-fabricated device 300b. The first bio-compatible layer 308 may be formed on the sacrificial layer 304, such that the first bio-compatible layer 308 adheres to the sacrificial layer 304. The first bio-compatible layer 308 defines a first side 312 of the bio-compatible device. That is, the first bio-compatible layer 308 defines an outer edge of the bio-compatible device.

The first bio-compatible layer 308 may include a variety of materials. For example, the first bio-compatible layer 308 may include can include parylene, polybenzobisoxazole ("PBO"), polyimides ("PI"), benzocyclobutene ("BCB"), polyethylene terephthalate ("PET"), other silicone elastomers, and/or another bio-compatible polymeric material that is suitable for processing. And in at least one such example, the first bio-compatible layer 308 may include polymeric comprising dichlorodi-p-xylylene. In such an example, the first bio-compatible layer 308 may be parylene-C sold by Specialty Coating Systems.

The term "bio-compatibility," as used in this disclosure, refers generally to the ability of a material or device to co-exist with a biological host. Bio-compatible materials are generally those that do not bring about a host response (such as an immune response) that results in deleterious effects to either the biological host or the material. In addition to being bio-compatible, the first bio-compatible layer 308 may be an electrically insulating material to isolate encapsulated electronics from the surrounding environment (e.g., from current-carrying particles and/or fluids).

Moreover, the first bio-compatible layer 308 may have a variety of thicknesses. For example, the first bio-compatible layer 308 may have a thickness between 5 to 50 micrometers, such as 10 micrometers. Other thicknesses of the first bio-compatible layer 308 are possible as well.

In an example, the first bio-compatible layer 308 may be formed by a microfabrication process such as chemical vapor deposition, and provides a surface on which various components can be formed. The first bio-compatible layer 308 may be formed on part of or all of the sacrificial layer 304. For example, the first bio-compatible layer 308 may be deposited on the sacrificial layer 304 to create a continuous layer that spans the entirety of the sacrificial layer 304. And in at least one such example, the first bio-compatible layer 308 may be a conformal coat. Alternatively, the first bio-compatible layer 308 may be deposited only in certain locations on the sacrificial layer 304. In such an example, the first bio-compatible layer 308 may be patterned in certain locations on the sacrificial layer 304 using one or more masks.

Further, the first bio-compatible layer 308 may be deposited onto the sacrificial layer 304 with a substantially uniform thickness such that a surface of the first bio-compatible layer 308 opposite the carrier substrate 302 forms a flat surface. In addition, the first bio-compatible layer 308 may have sufficient structural rigidity to be used as a substrate for assembling various components.

In an example, equipment that forms the first bio-compatible layer 308 may be preheated for around 1 hour before forming the first bio-compatible layer 308.

Moreover, an adhesion promoter may be applied to a surface of the sacrificial layer 304 before the first bio-compatible layer 308 is formed. With such an arrangement, adhesion of the first bio-compatible layer 308 to the sacrificial layer 304 may be improved. For example, an adhesion promoter may be applied to the surface 306 of the sacrificial layer 304.

In some embodiments, the adhesion promoter may comprise 3-methacryloyloxypropyltrimethoxysilane. And in such embodiments, the adhesion promoter may be A174 sold by Specialty Coating Systems and/or Sigma Aldrich. Moreover, in some embodiments, the adhesion promoter may comprise hexamethyldisilazane (HDMS). Other adhesion promoters are possible as well.

The adhesion promoter may be applied in a variety of ways. For example, the adhesion promoter may be applied by spin coating at a rate, baking at a temperature for a first time period, rinsing with a fluid, and baking at the temperature for a second time period. In some embodiments, the rate may be 3000 rotations per minute (rpm). And in such embodiments, applying the adhesion promoter by spin coating may involve accelerating and/or decelerating the partially-fabricated device 300a at a rate between 100 to 3000 rpm per second, such as 1000 to 1500 rpm per second. Moreover, in some embodiments, the temperature may be 90 degrees C. Further, in some embodiments, the first time period may be 2 minutes. Further still, in some embodiments, the fluid may include isopropyl alcohol (IPA). And, in some embodiments, the second time period may be 1 minute.

In another example, the adhesion promoter may be applied by soaking the partially-fabricated device 300a in a mixture including the adhesion promoter for a first time period, air drying on a towel for a second time period, rinsing with a fluid, and drying with a gas. In some embodiments, the mixture may comprise 100 parts deionized water (DI water), 100 parts IPA, and 1 part the adhesion promoter. Moreover, in some embodiments, the mixture may settle for around 2 hours before soaking the partially-fabricated device 300a in the mixture. Further, in some embodiments, the first time period may be 30 minutes. Moreover, in some embodiments, the second time period may be at least 30 minutes. Further, in some embodiments, the fluid may include IPA. And, in some embodiments, the gas may include nitrogen. All of the rinsing described herein may be performed in a variety ways, such as soaking in a bath in a tank, an automated spray, manually via a squirt bottle, etc.

In such an example, soaking the partially-fabricated device 300a in a mixture including the adhesion promoter for the first time period, air drying on a towel for the second time period, rinsing with the fluid, and/or drying with the gas may occur at room temperature. Moreover, in such an example, applying the adhesion promoter may further involve baking the partially-fabricated device 300a at a temperature for a time period after the adhesion promoter is applied to a surface of the sacrificial layer 304. In some embodiments, the temperature may be 90 degrees C. Moreover, in some embodiments, the time period may be 2 minutes.

Moreover, the partially-fabricated device 300a may be plasma cleaned before applying the adhesion promoter to a surface of the sacrificial layer 304. The partially-fabricated device 300a may be plasma cleaned in a variety of ways. For example, the partially-fabricated device 300a may be plasma cleaned at a power for a time period. In some embodiments, the power may be high. Moreover, in some embodiments, the time period may be 5 minutes.

Further, a surface of the sacrificial layer 304 may be treated, such that the first bio-compatible layer 308 bonds to the treated surface during formation of the first bio-compatible layer 308. For example, the surface 306 of the sacrificial layer 304 may be treated, such that the first bio-compatible layer 308 bonds to the treated surface during formation of the first bio-compatible layer 308. With this arrangement, the surface 308 may be roughened, such that adhesion of the first bio-compatible layer 308 to the sacrificial layer 304 may be improved.

The surface 306 may be treated in a variety of ways. For example, the surface 306 of the sacrificial layer 304 may be treated by etching using an inductively coupled plasma at a power for a time. In some embodiments, the inductively coupled plasma may include an oxygen plasma. Moreover, in some embodiments, the power may be 400 W with a 300 W bias. Further, in some embodiments, the time period may be 1 to 3 minutes. In some examples, the inductively coupled plasma may unevenly etch the surface 306, such that the surface 306 may be roughened. Other plasmas and/or types of plasmas may be used as well, such as plasma asher, a reactive ion etcher, etc.

Next, a first coating 314 is formed on the first bio-compatible layer 308 to provide a partially-fabricated device 300c as shown in FIG. 3c. The first coating 314 may help to protect the bio-compatible device from moisture.

The first coating 314 may include a variety of materials. For example, the first coating 314 may include one or more layers of inorganic materials, such as aluminum oxide, silicon oxide, titanium oxide, and/or silicon nitride. Further, in some examples, the first coating 314 may include one or more polymer layers. Further still, in some examples, the first coating 314 may include one or more inorganic layers and one or more polymer layers. In an example, the first coating 314 may be substantially transparent.

In an example, the one or more polymer layers of the first coating 314 may be composed of the same polymeric material as the first bio-compatible layer 308. However, in other examples, the one or more polymer layers of the first coating 314 may be composed of a different polymeric material than the first bio-compatible layer 308. The one or more polymer layers of the first coating 314 can be any of the polymeric materials mentioned herein that is bio-compatible.

In an example, the first coating 314 may include one aluminum oxide layer and one polymer layer. In addition, in such an example, the polymer layer of the first coating 314 may be formed on the first bio-compatible layer 308 and the inorganic layer may be formed on the polymer layer.

As another example, the first coating 314 may include two or more inorganic layers and two or more polymer layers, such as three inorganic layers and two polymer layers. And in such an example, respective inorganic layers may be formed on respective polymer layers in an alternating arrangement. Such an alternating arrangement of polymer layers and inorganic layers may improve the moisture protection and/or flexibility of the first coating 314. In an example, when the first coating 314 includes two or more layers, the layer of the two or more layers that is located over the other layers of the two or more layers may be an inorganic layer.

Moreover, the first coating 314 may have a variety of thicknesses. For example, the first coating 314 may have a thickness between 1 to 150 micrometers, such as 30 nanometers. In an example, when the first coating comprises one aluminum oxide layer and one polymer layer, the aluminum oxide layer may have a thickness of 20 nanometers and the polymer layer may have a thickness of 5 nanometers. In another example, when the first coating 314 includes two or more layers, each layer of the two or more layers may have a thickness between 1 to 30 nanometers.

In an example, the first coating 314 may be formed by a microfabrication process such as atomic layer deposition. The first coating 314 may be formed on part of or all of the first bio-compatible layer 308. For example, the first coating 314 may be deposited on the first bio-compatible layer 308 to create a continuous layer that spans the entirety of the first bio-compatible layer 308. Alternatively, the first coating 314 may be deposited only in certain locations on the first bio-compatible layer 308. In such an example, the first coating 314 may be patterned only in certain locations on the first bio-compatible layer 308 using one or more masks. In addition, the first coating 314 may be applied volumetrically.

Moreover, the partially-fabricated device 300b may be cleaned before forming the first coating 314 on the first bio-compatible layer 308. The partially-fabricated device 300b may be cleaned in a variety of ways. For example, the partially-fabricated device 300b may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further, the partially-fabricated device 300b may be baked before forming the first coating 314 on the first bio-compatible layer 308. The partially-fabricated device 300b may be baked at a temperature for a time period. In some embodiments, the temperature may be 90 degrees C. Moreover, in some embodiments, the time period may be 2 minutes. Further, in some embodiments, the partially-fabricated device 300b may be baked on a hot plate. After the partially-fabricated device 300b is baked, the partially-fabricated device 300b may be cooled to room temperature.

Further still, the partially-fabricated device 300b may be plasma cleaned before forming the first coating 314 on the first bio-compatible layer 308. With this arrangement, a surface 310 of the first bio-compatible layer 308 (as shown in FIG. 3b) may be roughened, such that adhesion of the first coating 314 to the first bio-compatible layer 308 may be improved. The partially-fabricated device 300b may be plasma cleaned in a variety of ways. For example, the partially-fabricated device 300b may be plasma cleaned at a power for a time period. In some embodiments, the power may be high. Moreover, in some embodiments, the time period may be 2 minutes.

In another example, the surface 310 of the first bio-compatible layer 308 may be treated before forming the first coating 314. With this arrangement, the surface 310 of the first bio-compatible layer 308 may be roughened, such that adhesion of the first coating 314 to the first bio-compatible layer 308 may be improved. The surface 310 may be treated in a variety of ways. For example, the surface 310 of the first bio-compatible layer 308 may be treated by etching using an inductively coupled plasma at a power for a time. In some embodiments, the inductively coupled plasma may include an oxygen plasma. Moreover, in some embodiments, the power may be 400 W with a 300 W bias. In some examples, the inductively coupled plasma may unevenly etch the surface 310, such that the surface 310 may be roughened. Further, in some embodiments, the time period may be 1 to 3 minutes. Other plasmas and/or types of plasmas may be used as well, such as plasma asher, a reactive ion etcher, etc.

As shown in FIG. 3d, a first mask 316 is formed on a portion 318 of the first coating 314 to provide a partially-fabricated device 300d. The first mask 316 may include a variety of materials. For example, the first mask 316 may include a photoresist layer, such as a photoresist layer comprising 2-ethoxyethyl acetate. In such an example, the first mask 316 may be AZ4620® sold by Capital Scientific.

Moreover, the first mask 316 may have a variety of thicknesses. For example, the first mask 316 may have thicknesses of 5 micrometers. Other thicknesses of the first mask 316 are possible as well.

In an example, the first mask 316 may be formed on the portion 318 of the first coating 314 by spin coating and patterning.

The first mask 316 may be spin coated in a variety of ways. For example, a material may be spin coated by placing the material on the partially-fabricated device 300c, applying a spread cycle, applying a spin cycle, and applying a deceleration cycle.

In some embodiments, placing the material on the partially-fabricated device 300c may include pouring (or pipetting) the material onto the partially-fabricated device 300c.

Moreover, in some embodiments, applying the spread cycle may include rotating the partially-fabricated device 300c at a first rate for a first time period. And in such embodiments, the first rate may be 500 rpm. And in such embodiments, the first time period may be 8 seconds. With this arrangement, the material may be spread over the portion 318 of the first coating 314. The spread cycle may further include accelerating the partially-fabricated device 300c at a second rate for a second time period before rotating the partially-fabricated device 300c at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300c at a first rate for a first time period. And in such embodiments, the first rate may be 3000 rpm. And in such embodiments, the first time period may be 38 seconds. With this arrangement, the thickness of the first mask 316 may be formed. The spin cycle may further include accelerating the partially-fabricated device 300c at a second rate for a second time period before rotating the partially-fabricated device 300c at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300c at a rate for a time period. And in such embodiments, the rate may be 1500 rpm per second. And in such embodiments, the time period may be 2 seconds.

Moreover, in some embodiments, the partially-fabricated device 300c may be placed in a vacuum chuck before placing the material on the partially-fabricated device 300c. And in such embodiments, the partially-fabricated device 300c may be removed from the vacuum chuck after applying the declaration cycle.

After the first mask 316 is spin coated, the first mask 316 may be baked before patterning. The first mask 316 may be baked in a variety of ways. For example, the first mask 316 may be baked at a temperature for a time period. In some embodiments, the temperature may be 90 degrees C. Moreover, in some embodiments, the time period may be 45 minutes. After the first mask 316 is baked, the first mask 316 may sit for a time period before further processing. In some embodiments, the time period may be 45 minutes.

In addition, the first mask 316 may be patterned in a variety of ways. For example, a material may be patterned by exposing and developing. In such an example, the material may be exposed to light at an intensity for a first time period, and developed by soaking in a fluid for a second time period. In some embodiments, the light may be ultra violet light (UV light) that is generated by a mercury lamp. Moreover, in some embodiments, the intensity may be 19 milliwatts per centimeter (mW/cm$^2$). Further, in some embodiments, the first time period may be 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 3 minutes. In an example, after the first mask 316 is exposed, the first mask 316 may sit for a time period before the first mask 316 is developed. In some embodiments, the time period is 15 minutes.

Further, the partially-fabricated device 300c may be cleaned before forming the first mask 316 on the portion 318 of the first coating 314. The partially-fabricated device 300c may be cleaned in a variety of ways. For example, the partially-fabricated device 300c may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300c may be baked before forming the first mask 316 on the portion 318 of the first coating 314. The partially-fabricated device 300c may be baked at a temperature for a time period. In some embodiments, the temperature may be 90 degrees C. Moreover, in some embodiments, the time period may be 2 minutes.

As shown in FIG. 3e, an etch stop 320 is formed on an exposed portion 321 of the first coating 314 (i.e., the portion that is not covered by the first mask 316) to provide a partially-fabricated device 300e. With this arrangement, the etch stop 320 is formed over a first portion 323 of the first bio-compatible layer 308.

The etch stop 320 may include a variety of materials. For example, the etch stop 320 may include one or more non-conductive materials, such as silicon oxide, silicon nitride, and aluminum oxide. Further, the etch stop 320 may include one or more metals, such as aluminum, titanium, nickel, and/or chromium. In an example, the etch stop 320 may include an aluminum layer.

Moreover, the etch stop 320 may have a variety of thicknesses. For example, the etch stop 320 may have a thickness between 1 to 500 nanometers, such as 300 nanometers. In an example, the etch stop 320 may be formed by a microfabrication process such as chemical vapor deposition. The etch stop 320 may be deposited on the exposed portion 321 of the first coating 314 to create a continuous layer that spans the entirety of the exposed portion 321 of the first coating 314. Alternatively, the etch stop 320 may be deposited only in certain locations on the exposed portion 321 of the first coating 314. In such an example, the etch stop 320 may be patterned only in certain locations on the exposed portion 321 of the first coating 314 using one or more masks.

Next, the first mask 316 is removed and a second bio-compatible layer 322 is formed on the etch stop 320 and the first coating 314 to provide a partially fabricated device 300f, as shown in FIG. 3f. With this arrangement, the second bio-compatible layer 322 may be formed over the etch stop 320 and the first bio-compatible layer 308.

The first mask 316 may be removed in a variety of ways. For example, the first mask 316 may be removed by soaking in a first fluid for a first time period, rinsing in a second fluid, drying with a gas, and baking at a temperature for a second time period. In some embodiments, the first fluid may include a solvent, such as acetone. Moreover, in some embodiments, the first time period may be 4 hours. Further, in some embodiments, the second fluid may include IPA. Further still, in some embodiments, the gas may include nitrogen. Moreover, in some embodiments, the temperature may be 90 degrees C. Further, in some embodiments, the second time period may be 2 minutes.

In an example, removal may further involve sonicating for a time period after soaking in the first fluid and before rinsing in the second fluid. In some embodiments, the time period may be around 3 seconds. Moreover, in some embodiments, the first mask 316 may be removed by one or more cycles of soaking in the first fluid and sonicating. As another example, the first mask 316 may be removed using an inductively coupled plasma, such as oxygen plasma.

In an example, the second bio-compatible layer 322 can be composed of the same material as the first bio-compatible layer 308. However, in other examples, the second bio-compatible layer 322 can be composed of a different material than the first bio-compatible layer 308. The second bio-compatible layer 322 can be any one of the materials mentioned herein that is both bio-compatible and electrically insulating. When the etch stop 320 includes one or more metals, the second bio-compatible layer 322 may thus serve to insulate the etch stop 320 so as to reduce shorting of a conductive pattern formed over the etch stop 320.

Moreover, the second bio-compatible layer 322 may have a variety of thicknesses. In an example, the second bio-compatible layer 322 may have the same or similar thickness of the first bio-compatible layer 308. For example, the second bio-compatible 322 may have a thickness between 5 to 50 micrometers, such as 10 micrometers. However, in other examples, the second bio-compatible layer 322 may have a thickness that is different than the thickness of the first bio-compatible layer 308.

Further, in an example, the second bio-compatible layer 322 may be formed in the same or similar way as the first bio-compatible layer 308. However, in other examples, the second bio-compatible layer 322 may be formed by a different process (or processes) than the process (or processes) used to form the first bio-compatible layer 308.

For example, the second bio-compatible layer 322 may be formed by a microfabrication process such as chemical vapor deposition. The second bio-compatible layer 322 may be deposited on the etch stop 320 and the first coating 314 to create a continuous layer that spans the entirety of the etch stop 320 and the first coating 314. And in at least one such example, the second bio-compatible layer 322 may be a conformal coat. In some embodiments, the second bio-compatible layer 322 may be formed on part of or all of the first coating 314.

In an example, equipment that forms the second bio-compatible layer 322 may be preheated for around 1 hour before forming the second bio-compatible layer 322.

Moreover, the partially-fabricated device 300e may be cleaned before forming the second bio-compatible layer 322 on the etch stop 320 and the first coating 314. The partially-fabricated device 300e may be cleaned in a variety of ways. For example, the partially-fabricated device 300e may be cleaned by rinsing in a fluid for a first time period, drying with a gas, and baking at a temperature for a second time period. In some embodiments, the fluid may include DI water. Moreover, in some embodiments, the first time period may be at least 30 seconds. Further, in some embodiments, the gas may include nitrogen. Further still, in some embodiments, the temperature may be 90 degrees C. Moreover, in some embodiments, the time period may be 2 minutes.

Further, the partially-fabricated device 300e may be plasma cleaned before forming the second bio-compatible layer 322 on the etch stop 320 and the first coating 314. The partially-fabricated device 300e may be plasma cleaned in a variety of ways. For example, the partially-fabricated device 300e may be plasma cleaned at a power for a time period. In some embodiments, the power may be high. Moreover, in some embodiments, the time period may be 5 minutes. After the partially-fabricated device 300e is plasma cleaned, the partially-fabricated device 300e may be placed under a vacuum before formation of the second bio-compatible layer 322.

In an example, a surface of the first coating 314 is treated, such as a surface 315 of the first coating 314 (as shown in FIG. 3c). With this arrangement, the surface 315 may be roughened, such that adhesion of the second bio-compatible layer 322 to the first coating 314 may be improved. The surface 315 may be treated in a variety of ways. For example, the surface 315 may be treated by etching using an inductively coupled plasma at a power for a time. In some embodiments, the inductively coupled plasma may include an oxygen plasma. Moreover, in some embodiments, the power may be 400 W with a 300 W bias. In some examples, the inductively coupled plasma may unevenly etch the surface 315, such that the surface 315 may be roughened. Further, in some embodiments, the time period may be 30 seconds. Other plasmas and/or types of plasmas may be used as well, such as plasma asher, a reactive ion etcher, etc.

Next, a seed layer 326 is formed on the second bio-compatible layer 322 to provide a partially-fabricated device 300g, as shown in FIG. 3g. With this arrangement, the seed layer 326 is formed over the etch stop 320 and the first bio-compatible layer 308.

Such a seed layer 326 can be used to adhere to both the second bio-compatible layer 322, and an additional metal structure that is patterned on the seed layer 326, as will be described below. For example, the seed layer 326 may include one or more materials that adhere to the second bio-compatible layer 322 and/or serve as a guide to electroplate the remainder of a metal structure that forms a component. In such an example, the seed layer 326 may include one or more layers of titanium, nickel, aluminum, platinum, and/or gold.

For instance, in some examples, the seed layer 326 may include a first layer that includes titanium, nickel, aluminum, and/or platinum and a second layer that includes gold. And in at least one such example, the first layer of the seed layer 326 may be a titanium layer and the second layer of seed layer 326 may be a gold layer.

Moreover, the seed layer 326 may have a variety of thicknesses. For example, when the seed layer includes a first layer and a second layer, the first layer may have a thickness between 1 to 30 nanometers, such as 30 nanometers; and the second layer may have a thickness between 100 to 1000 nanometers, such as 500 nanometers. Other thicknesses for the seed layer 326 are possible as well.

In an example, the seed layer 326 may be formed by a microfabrication process such as sputtering. However, in other examples, the seed layer 326 may be formed by other microfabrication processes such as evaporation. In some embodiments, when the seed layer 326 includes a first layer and a second layer: the first layer may be formed on the second bio-compatible layer 322 and the second layer may be formed on the first layer. With this arrangement, the first layer of the seed layer 326 may adhere to the second bio-compatible layer 322 and a conductive pattern may be formed on the second layer of the seed layer 326. Accordingly, in such an example, the first layer of the seed layer 326 may be referred to as an adhesion layer.

In some examples, the seed layer 326 may be formed on the second bio-compatible layer 322 at a temperature. With this arrangement, one or more stresses on the partially-fabricated device 300f may be reduced. In some embodiments, the temperature may be less than 100 C. Other temperatures are possible as well. Moreover, in some examples, the temperature may be selected based on the one or more materials of the first bio-compatible layer 308 and/or the one or more materials of the second bio-compatible layer 322.

Further, in some examples, a surface 324 of the second bio-compatible layer 322 (shown in FIG. 3f) may treated before forming the seed layer 314 on the second bio-compatible layer 322. With this arrangement, the surface 324 of the second bio-compatible layer 322 may be roughened, such that adhesion of the seed layer 326 to the second bio-compatible layer 322 may be improved. The surface 324 may be treated in a variety of ways. For example, the surface 324 of the second bio-compatible layer 324 may be treated by sputtering etching using an etchant at a power for a time period. In some embodiments, the etchant may include an argon plasma and/or an oxygen plasma. Moreover, in some embodiments, the power may be between 100 to 200 W. Further, in some embodiments, the time period may be between 1 to 2 minutes. In some examples, the etchant may unevenly etch the surface 324 of the second bio-compatible layer 322, such that the surface 324 may be roughened. Other plasmas and/or types of plasmas may be used as well, such as plasma asher, a reactive ion etcher, etc.

As shown in FIG. 3h, a second mask 328 is formed on a portion of 330 of the seed layer 326 to provide a partially-fabricated device 300h. At least part of the portion 330 of the seed layer 326 may not be located over the etch stop 320. The second mask 328 may include a variety of materials. For example, the second mask 328 can be composed of the same material as the first mask 316. However, in other examples, the second mask 328 can be composed of a different material than the first mask 316. The second mask 328 may include any of the materials mentioned herein that the first mask 316 may include.

Moreover, the second mask 328 may have a variety of thicknesses. In an example, the second mask 328 may have the same or similar thickness as the first mask 316. For example, the second mask 328 may have thicknesses of 5 micrometers. However, in other examples, the second mask 328 may have a thickness that is different than the thickness of the first mask 316.

Further, in an example, the second mask 328 may be formed on the portion 330 of the seed layer 326 the same or similar way as the first mask 316 may be formed on the portion 318 of the first coating 314. For example, the second mask 328 may be formed on the portion 330 of the seed layer 326 by spin coating and patterning.

The second mask 328 may be spin coated in a variety of ways. For example, a material may be spin coated by placing the material on the partially-fabricated device 300g, applying a spread cycle, applying a spin cycle, and applying a deceleration cycle.

In some embodiments, placing the material on the partially-fabricated device 300g may include pouring (or pipetting) the material onto the partially-fabricated device 300g.

Moreover, in some embodiments, applying the spread cycle may include rotating the partially-fabricated device 300g at a first rate for a first time period. And in such embodiments, the first rate may be 500 rpm. And in such embodiments, the first time period may be 8 seconds. With this arrangement, the material may be spread over the portion 330 of the seed layer 326. The spread cycle may further include accelerating the partially-fabricated device 300g at a second rate for a second time period before rotating the partially-fabricated device 300g at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300g at a first rate for a first time period. And in such embodiments, the first rate may be 3000 rpm. And in such embodiments, the first time period may be 38 seconds. With this arrangement, the thickness of the second mask 328 may be formed. The spin cycle may further include accelerating the partially-fabricated device 300g at a second rate for a second time period before rotating the partially-fabricated device 300g at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300g at a rate for a time period. And in such embodiments, the rate may be 1500 rpm per second. And in such embodiments, the time period may be 2 seconds.

Moreover, in some embodiments, the partially-fabricated device 300g may be placed in a vacuum chuck before placing the material on the partially-fabricated device 300g. And in such embodiments, the partially-fabricated device 300g may be removed from the vacuum chuck after applying the declaration cycle.

After the second mask 328 is spin coated, the second mask 328 may be baked before patterning. The second mask 328 may be baked in a variety of ways. For example, the second mask 328 may be baked at a temperature for a time period. In some embodiments, the temperature may be 90 degrees C. Moreover, in some embodiments, the time period may be 45 minutes. After the second mask 328 is baked, the second mask 328 may sit for a time period before further processing. In some embodiments, the time period may be 45 minutes.

In addition, the second mask 328 may be patterned in a variety of ways. For example, a material may be patterned by exposing and developing. In such an example, the material may be exposed to light at an intensity for a first time period, and developed by soaking in a fluid for a second time period. In some embodiments, the light may be UV light that is generated by a mercury lamp. Moreover, in some embodiments, the intensity may be 19 mW/cm². Further, in some embodiments, the first time period may be 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 3 minutes. In an example, after the second mask 328 is exposed, the second mask 328 may sit for a time period before the second mask 328 is developed. In some embodiments, the time period may be 15 minutes.

Further, the partially-fabricated device 300g may be cleaned before forming the second mask 328 on the portion 330 of the seed layer 326. The partially-fabricated device 300g may be cleaned in a variety of ways. For example, the partially-fabricated device 300g may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300g may be baked before forming the second mask 328 on the portion 330 of the seed layer 326. The partially-fabricated device 300g may be baked at a temperature for a time period. In some embodiments, the temperature may be 90 degrees C. Moreover, in some embodiments, the time period may be 2 minutes.

As shown in FIG. 3i, a first metal layer 332 is formed on an exposed portion 334 (i.e., the portion that is not covered by the second mask 328) of the seed layer 326 to provide a partially-fabricated device 300i. With this arrangement, the first metal layer 332 is formed over the etch stop 320. The first metal layer 332 defines sensor electrodes 336.

The first metal layer 332 may include a variety of conductive materials. For example, the first metal layer may include one or more layers of titanium, aluminum, chromium, palladium, and/or platinum. In an example, the first metal layer may include a first layer that includes titanium, aluminum, and/or chromium; a second layer that includes palladium; and a third layer that includes platinum. And in at least one such example, the first layer of the first metal layer 332 may be a titanium layer, the second layer of the first metal layer 332 may be a palladium layer, and the third layer of the first metal layer 332 may be a platinum layer.

Moreover, the first metal layer 332 may have a variety of thicknesses. For example, when the first metal layer 332 includes a first layer, a second layer, and a third layer: the first layer may have a thickness between 1 to 50 nanometers, such as 30 nanometers; the second layer may have a thickness between 1 to 50 nanometers, such as 30 nanometers; and the third layer may have a thickness between 100 to 500 nanometers, such as 500 nanometers. Other thicknesses of the first metal layer 332 are possible as well.

In an example, the first metal layer 332 may be formed by a microfabrication process such as sputtering. However, in other examples, the first metal layer 332 may be formed by other microprocesses such as evaporation. In some embodiments, when the first metal layer 332 includes a first layer, a second layer, and a third layer: the first layer may be formed on the exposed portion 334 of the seed layer 326, the second layer may be formed on the first layer, and the third layer may be formed on the second layer. With this arrangement, the first layer may adhere to the exposed portion 334 of the seed layer 326 and the second layer may reduce alloying of the third layer with the first layer. Accordingly, in such an example, the first layer of the first metal layer 332 may be referred to as an adhesion layer and the second layer of the first metal layer 332 may be referred to as a barrier layer. In addition, in such an example, the third layer of the first metal layer 332 may define the sensor electrodes 336.

In some examples, the first metal layer 332 may be formed on the exposed portion 334 of the seed layer 326 at a temperature. With this arrangement, one or more stresses on the partially-fabricated device 300i may be reduced. In some embodiments, the temperature may be less than 100 C. Other temperatures are possible as well. Moreover, in some examples, the temperature may be selected based on the one or more materials of the first bio-compatible layer 308 and/or the one or more materials of the second bio-compatible layer 322.

Further, in some examples, a surface of the exposed portion 334 of the seed layer 326 may treated before forming the first metal layer 332 on the exposed portion 334 of the seed layer 326. With this arrangement, the surface of the exposed portion 334 of the seed layer 326 may be roughened, such that adhesion of the first metal layer 332 to the exposed portion 334 of the seed layer 326 may be improved. The surface may be treated in a variety of ways. For example, the surface of the exposed portion 334 of the seed layer 326 may be treated by sputtering etching using an etchant at a power for a time period. In some embodiments, the etchant may include an argon plasma and/or an oxygen plasma. Moreover, in some embodiments, the power may be between 100 to 200 W. Further, in some embodiments, the time period may be between 1 to 2 minutes. In some examples, the etchant may unevenly etch the surface of the exposed portion 334 of the seed layer 326, such that the surface may be roughened. Other plasmas and/or types of plasmas may be used as well, such as plasma asher, a reactive ion etcher, etc.

FIG. 3i-2 shows a top view of the first metal layer 332 formed on the exposed portion 334 of the seed layer 326. As noted, the first metal layer 332 defines sensor electrodes 336. As shown in FIG. 3i-2, the sensor electrodes 336 include a working electrode 336A and a counter electrode 336B in an interdigitated arrangement. In the illustrated example, the working electrode 336A includes four fingers (336A1, 336A2, 336A3, and 336A4) that each have a width, for example, between 1 to 100 micrometers. The counter electrode 336B includes five fingers (336B1, 336B2, 336B3, 336B4, and 336B5) that each have a width, for example, between 100 micrometers and 5000 micrometers. In some embodiments, the width of the fingers of the counter electrode 336B may be greater than the width of the fingers of the working electrode 336A by a factor of four. For example, the width of the fingers of the counter electrode 336B may be 100 micrometers and the width of the fingers of the working electrode 336A may be 25 micrometers. In addition, each of the fingers of the counter electrode 336B may be spaced apart from a respective finger of the working electrode 336A by a certain distance, such as 50 micrometers. The sensor electrodes 336 may be electrically connected to an electronic component via electrical interconnects.

Although one example of the sensor electrodes 336 has been described with reference to FIG. 3i-2, the sensor electrodes 336 may take a variety of other forms as well. As one example, the sensor electrodes 336 may include three electrodes, such as a working electrode, a counter electrode, and a reference electrode. In such an example, when the working electrode and the counter electrode are formed in an interdigitated arrangement, the fingers of the working electrode may have the same or similar width as the fingers of the counter electrode. Further, the number electrodes in the sensor electrodes 336 and one or more dimensions of the electrodes in the sensor electrodes 336 (e.g., width of the fingers) may be selected based on a variety of parameters, such as the sensitivity of the sensor electrodes 336.

As shown in FIG. 3j, the second mask 328 is removed and a third mask 338 is formed on the first metal layer 332 and a portion 340 of the seed layer 326 to provide a partially-fabricated device 300j.

The second mask 328 may be removed in a variety of ways. In an example, the second mask 328 may be removed the same or similar was as the first mask 316 may be removed. For example, the second mask 328 may be removed by soaking in a first fluid for a first time period, sonicating for a second time period, rinsing in a second fluid, drying with a gas, and baking at a temperature for a third time period. In some embodiments, the first fluid may include a solvent, such as acetone. Moreover, in some embodiments, the first time period may be 4 hours. Further, in some embodiments, the second time period may be around 2 seconds. Further still, in some embodiments, the second fluid may include IPA. Moreover, in some embodiments, the gas may include nitrogen. Further, in some embodiments, the temperature may be 90 degrees C. Further still, in some embodiments, the second time period may be 2 minutes. As another example, the second mask 328 may be removed using an inductively coupled plasma, such as oxygen plasma.

In some embodiments, after the second mask 328 is removed, an inspection may be performed to determine if any cracks formed in the first metal layer 332.

The third mask 338 may include a variety of materials. For example, the third mask 338 can be composed of the same material as the first mask 316 and/or the second mask 328. However, in other examples, the third mask 338 can be composed of a different material than the first mask 316 and/or the second mask 328. The third mask 338 may include any of the materials mentioned herein that the first mask 316 and the second mask 328 may include.

Moreover, the third mask 338 may have a variety of thicknesses. In an example, the third mask 338 may have the same or similar thickness as the first mask 316 and/or the second mask 328. For example, the third mask 338 may have thicknesses of 5 micrometers. However, in other examples, the third mask 338 may have a thickness that is different than the thickness of the first mask 316 and/or the second mask 328.

Further, in an example, the third mask 338 may be formed on the first metal layer 332 and the portion 340 of the seed layer 326 the same or similar way as the first mask 316 may be formed on the portion 318 of the first coating 314 and/or the second mask 328 may be formed on the portion 330 of the seed layer 326. For example, the third mask 338 may be formed on the first metal layer 332 and the portion 340 of the seed layer 326 by spin coating and patterning.

The third mask 338 may be spin coated in a variety of ways. For example, a material may be spin coated by placing the material on the partially-fabricated device 300i (after the second mask 328 is removed), applying a spread cycle, applying a spin cycle, and applying a deceleration cycle.

In some embodiments, placing the material on the partially-fabricated device 300i may include pouring (or pipetting) the material onto the partially-fabricated device 300i.

Moreover, in some embodiments, applying the spread cycle may include rotating the partially-fabricated device 300i (after the second mask 328 has been removed) at a first rate for a first time period. And in such embodiments, the first rate may be 500 rpm. And in such embodiments, the first time period may be 8 seconds. With this arrangement, the material may be spread over the first metal layer 332 and the portion 340 of the seed layer 326. The spread cycle may further include accelerating the partially-fabricated device 300i at a second rate for a second time period before rotating the partially-fabricated device 300i at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300i at a first rate for a first time period. And in such embodiments, the first rate may be 3000 rpm. And in such embodiments, the first time period may be 38 seconds. With this arrangement, the thickness of the third mask 338 may be formed. The spin cycle may further include accelerating the partially-fabricated device 300i at a second rate for a second time period before rotating the partially-fabricated device 300i at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300i at a rate for a time period. And in such embodiments, the rate may be 1500 rpm per second. And in such embodiments, the time period may be 2 seconds.

Moreover, in some embodiments, the partially-fabricated device 300i may be placed in a vacuum chuck before placing the material on the partially-fabricated device 300i. And in such embodiments, the partially-fabricated device 300i may be removed from the vacuum chuck after applying the declaration cycle.

After the third mask 338 is spin coated, the third mask 338 may be baked before patterning. The third mask 338 may be baked in a variety of ways. For example, the third mask 338 may be baked at a temperature for a time period. In some embodiments, the temperature may be 90 degrees C. Moreover, in some embodiments, the time period may be 45 minutes. After the third mask 338 is baked, the third mask 338 may sit for a time period before further processing. In some embodiments, the time period may be 45 minutes. During the time period, the third mask 338 may be cooled to room temperature.

In addition, the third mask 338 may be patterned in a variety of ways. For example, a material may be patterned by exposing and developing. In such an example, the material may be exposed to light at an intensity for a first time period, and developed by soaking in a fluid for a second time period. In some embodiments, the light may be UV light that is generated by a mercury lamp. Moreover, in some embodiments, the intensity may be 19 mW/cm$^2$. Further, in some embodiments, the first time period may be 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 3 minutes. In an example, after the third mask 338 is exposed, the third mask 338 may sit for a time period before the third mask 338 is developed. In some embodiments, the time period may be 15 minutes.

Further, the partially-fabricated device 300i may be cleaned before forming the third mask 328 on the first metal layer 332 and the portion 340 of the seed layer 326. The partially-fabricated device 300i may be cleaned in a variety of ways. For example, the partially-fabricated device 300i may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300i may be baked before forming the third mask 338 on the first metal layer 332 and the portion 340 of the seed layer 326. The partially-fabricated device 300i may be baked at a temperature for a time period. In some embodiments, the temperature may be 90 degrees C. Moreover, in some embodiments, the time period may be 2 minutes. Further, in some embodiments, the partially-fabricated device 300i may be baked on a hot plate. After the partially-fabricated device 300i is baked, the partially-fabricated device 300i may be cooled to room temperature.

As shown in FIG. 3k, a second metal layer 342 is formed on an exposed portion 344 of the seed layer 326 (i.e., the portion that is not covered by the third mask 338) to provide a partially-fabricated device 300k. The second metal layer 342 defines components including an antenna 346, electrical contacts 348, and electrical interconnects 350. In some examples, the electrical contacts 348 may be referred to as bond pads. Further, in some examples, the electrical interconnects 350 may function to electrically connect one or more components of the bio-compatible device, such as the sensor electrodes 336 and an electronic component.

The second metal layer 342 may include a variety of conductive materials. For example, the second metal layer 342 may include one or more layers of platinum, silver, gold, palladium, titanium, copper, chromium, nickel, aluminum, and/or other metals or conductive materials. In some embodiments, the second metal layer 342 may include a substantially transparent conductive material for at least some components (e.g., a material such as indium tin oxide). In an example, the second metal layer 342 may comprise one gold layer.

Moreover, the second metal layer 342 may have a variety of thicknesses. For example, the second metal layer 342 may have a thickness between 5 to 20 micrometers, such as 9 to 10 micrometers. Other thicknesses of the second metal layer 342 are possible as well.

In an example, the second metal layer 342 may be formed by a microfabrication process such as electroplating. Other microfabrication processes for forming the second metal layer 342 are possible as well. The second metal layer 342 may be electroplated in a variety ways. For example, the second metal layer 342 may be electroplated in a bath at a current for a time period. In some embodiments, the current is 30 milliamps (mA). Moreover, in some embodiments, the time period is 120 minutes.

Moreover, the partially-fabricated device 300j may be plasma cleaned before forming the second metal layer 342 on the exposed portion 344 of the seed layer 326. The partially-fabricated device 300j may be plasma cleaned in a variety of ways. For example, the partially-fabricated device 300j may be plasma cleaned at a power for a time period. In some embodiments, the power may be high. Moreover, in some embodiments, the time period may be 2 minutes.

Next, the third mask 338 is removed and a fourth mask 352 is formed on the first metal layer 332, the second metal layer 342, and a portion 354 of the seed layer 326 to provide a partially-fabricated device 300l as shown in FIG. 3l. With this arrangement, a portion 356 of the seed layer 326 is exposed.

The third mask 338 may be removed in a variety of ways. In an example, the third mask 338 may be removed in the same or similar way as the first mask 316 and/or the second mask 328. For example, the third mask 338 may be removed by soaking in a first fluid for a time period, rinsing in a second fluid, and drying with a gas. In some embodiments, the first fluid may include a solvent, such as acetone. Moreover, in some embodiments, the first time period may be around 2 minutes. Further, in some embodiments, the second fluid may include IPA. Further still, in some embodiments, the gas may include nitrogen. As another example, the third mask 338 may be removed using an inductively coupled plasma, such as oxygen plasma.

The fourth mask 352 may include a variety of materials. For example, the fourth mask 352 can be composed of the same material as the first mask 316, the second mask 328, and/or the third mask 328. However, in other examples, the fourth mask 352 can be composed of a different material than the first mask 316, the second mask 328, and/or the third mask 328. The fourth mask 352 may include any of the materials mentioned herein that the first mask 316, the second mask 328, and third mask 338 may include.

Moreover, the fourth mask 352 may have a variety of thicknesses. In an example, the fourth mask 352 may have the same or similar thickness as the first mask 316, the second mask 328, and/or the third mask 328. For example, the fourth mask 352 may have thicknesses of 5 micrometers. However, in other examples, the fourth mask 352 may have a thickness that is different than the thickness of the first mask 316, the thickness of the second mask 328, and/or the thickness of the third mask 338.

Further, in an example, the fourth mask 352 may be formed on the first metal layer 332, the second metal layer 342, and the portion 354 of the seed layer 326 the same or similar way as the first mask 316 may be formed on the portion 318 of the first coating 314, the second mask 328 may be formed on the portion 330 of the seed layer 326, and the third mask 338 may be formed on the first metal layer 332 and the portion 340 of the seed layer 326. For example, the fourth mask 352 may be formed on the first metal layer 332, the second metal layer 342, and the portion 354 of the seed layer 326 by spin coating and patterning.

The fourth mask 352 may be spin coated in a variety of ways. For example, a material may be spin coated by placing the material on the partially-fabricated device 300k (after the third mask 338 is removed), applying a spread cycle, applying a spin cycle, and applying a deceleration cycle.

In some embodiments, placing the material on the partially-fabricated device 300k may include pouring (or pipetting) the material onto the partially-fabricated device 300k.

Moreover, in some embodiments, applying the spread cycle may include rotating the partially-fabricated device 300k at a first rate for a first time period. And in such embodiments, the first rate may be 500 rpm. And in such embodiments, the first time period may be 8 seconds. With this arrangement, the material may be spread over the first metal layer 332, the second metal layer 342, and the portion 354 of the seed layer 326. The spread cycle may further include accelerating the partially-fabricated device 300k at a second rate for a second time period before rotating the partially-fabricated device 300k at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300k at a first rate for a first time period. And in such embodiments, the first rate may be 3000 rpm. And in such embodiments, the first time period may be 38 seconds. With this arrangement, the thickness of the fourth mask 352 may be formed. The spin cycle may further include accelerating the partially-fabricated device 300k at a second rate for a second time period before rotating the partially-fabricated device 300k at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300k at a rate for a time period. And in such embodiments, the rate may be 1500 rpm per second. And in such embodiments, the time period may be 2 seconds.

Moreover, in some embodiments, the partially-fabricated device 300k may be placed in a vacuum chuck before placing the material on the partially-fabricated device 300k. And in such embodiments, the partially-fabricated device 300k may be removed from the vacuum chuck after applying the deceleration cycle.

After the fourth mask 352 is spin coated, the fourth mask 352 may be baked before patterning. The fourth mask 352 may be baked in a variety of ways. For example, the fourth mask 352 may be baked at a temperature for a time period. In some embodiments, the temperature may be 90 degrees C. Moreover, in some embodiments, the time period may be 5 minutes. After the fourth mask 352 is baked, the fourth mask 352 may sit for a time period before further processing. In some embodiments, the time period may be 5 minutes.

In addition, the fourth mask 352 may be patterned in a variety of ways. For example, a material may be patterned by exposing and developing. In such an example, the material may be exposed to light at an intensity for a first time period, and developed by soaking in a fluid for a second time period. In some embodiments, the light may be UV light that is generated by a mercury lamp. Moreover, in some embodiments, the intensity may be 19 mW/cm$^2$. Further, in some embodiments, the first time period may be 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 2 minutes. In an example, after the fourth mask 352 is exposed, the fourth mask 352 may sit for a time period before the fourth mask 352 is developed. In some embodiments, the time period may be 5 minutes.

Further, after the fourth mask 352 is developed, the partially-fabricated device 300l may be further processed. The partially-fabricated device 300l may be further processed in a variety of ways. For example, the partially-fabricated device 300l may be further processed by rinsing in a fluid, drying with a gas, and baking at a temperature for a time period. In some embodiments, the fluid may include DI water. Moreover, in some embodiments, the gas may include nitrogen. Further, in some embodiments, the temperature may be 90 degrees C. Further still, in some embodiments, the time period may be 30 minutes. After the partially-fabricated device 300l is further processed, the partially-fabricated device 300l may be cooled to room temperature.

Further, the partially-fabricated device 300k may be cleaned before forming the fourth mask 352 on the first metal layer 332, the second metal layer 342, and the portion 354 of the seed layer 326. The partially-fabricated device 300k may be cleaned in a variety of ways. For example, the partially-fabricated device 300k may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300k may be baked before forming the fourth mask 352 on the first metal layer 332, the second metal layer 342, and the portion 354 of the seed layer 326. The partially-fabricated device 300k may be baked at a temperature for a time period. In some embodiments, the temperature may be 90 degrees C. Moreover, in some embodiments, the time period may be 2 minutes. Further, in some embodiments, the partially-fabricated device 300k may be baked on a hot plate. After the partially-fabricated device 300k is baked, the partially-fabricated device 300k may be cooled to room temperature.

As shown in FIG. 3m, the exposed portion 356 of the seed layer 326 (i.e., the portion of the seed layer 326 that is not covered by the fourth mask 352) is removed thereby leaving the portion 354 of the seed layer 326 and the fourth mask 352 is removed to provide a partially-fabricated device 300m. The portion 354 of the seed layer 326 may include a portion 326B of the seed layer 326. The portion 326B of the seed layer 326 may define an electrical interconnects 358.

The portion 356 of the seed layer 326 may be removed in a variety of ways. For example, the portion 356 of the seed layer 326 may be removed by wet etching. In some embodiments, when the seed layer 326 includes a gold layer and a titanium layer, the portion 356 of the seed layer 326 may be removed by wet etching the gold layer of the portion 356 of the seed layer 326 and the titanium layer of the portion 356 of the seed layer 326.

The gold layer of the portion 356 of the seed layer 326 may be wet etched in a variety of ways. For example, the gold layer of the portion 356 of the seed layer 326 may be wet etched for a time period at a temperature. In some embodiments, the time period may be between 1 to 2 minutes. Moreover, in some embodiments, the temperature may be room temperature. After the gold layer of the portion 356 of the seed layer 326 is wet etched, removing the portion 356 of the seed layer 326 may involve rinsing in a fluid and drying with a gas. In some embodiments, the fluid may include DI water. Moreover, in some embodiments, the gas may include nitrogen.

Moreover, the titanium layer of the portion 356 of the seed layer 326 may be wet etched in a variety of ways. For example, the titanium layer of the portion 356 of the seed layer 326 may be wet etched for a time period at a temperature. In some embodiments, the time period may be 1 minute. Moreover, in some embodiments, the temperature may be 100 degrees C. After the titanium layer of the portion 356 of the seed layer 326 is wet etched, removing the portion 356 of the seed layer 326 may involve rinsing in a fluid and drying with a gas. In some embodiments, the fluid may include DI water. Moreover, in some embodiments, the gas may include nitrogen. In an example, after the titanium layer of the portion 356 of the seed layer 326 is wet etched, the partially-fabricated device 300m may change color.

As noted, the portion of 326B of the seed layer 326 may define the electrical interconnects 358. The electrical interconnects 358 may function to electrically connect one or more components of the bio-compatible device 300t, such as the sensor electrodes 336 and an electronic component. With this arrangement, an electrical connection via the electrical interconnects 358 may have a higher resistance than an electrical connection via the electrical interconnects 350.

Together, the first metal layer 332, the second metal layer 342, and the portion 326B of the seed layer 326 may define a conductive pattern 360. With this arrangement, the conductive pattern 360 is formed over the etch stop 320, the first portion 323 of the first bio-compatible layer 308, and a second portion 362 of the first bio-compatible layer 308. As shown in FIG. 3m, the second portion 362 of the first bio-compatible layer 308 is not covered by the etch stop 320. The conductive pattern 360 defines the sensor electrodes 336, the antenna 346, the electrical contacts 348, the electrical interconnects 350, and the electrical interconnects 358.

Moreover, a surface of the partially-fabricated device 300l (after the portion 356 of the seed layer 326 has been removed) may be treated before the fourth mask 352 is removed. The surface the partially-fabricated device 300l may be treated in a variety of ways. For example, the surface of the partially-fabricated device 300l may be treated by etching using an inductively coupled plasma at a power for a time period. With this arrangement, the surface of the partially-fabricated device 300l may be roughened. In some embodiments, the inductively coupled plasma may include an oxygen plasma. Moreover, in some embodiments, the power may be 400 W with a 300 W bias. Further, in some embodiments, the time period may be 30 seconds. In some examples, the inductively coupled plasma may unevenly etch the surface of the partially-fabricated device 300l, such that the surface may be roughened. Other plasmas and/or types of plasmas may be used as well, such as a plasma asher, a reactive ion etcher, etc.

After the surface of the partially-fabricated device 300l is treated, a resistance of the conductive pattern 360 may be measured. The resistance of the conductive pattern 360 may be measured in a variety of ways. For example, the resistance of the conductive pattern 360 may be measured by applying a voltage source to the conductive pattern 360 and measuring a current of the conductive pattern 360. In some embodiments, the voltage source may be 10 volts (V). Moreover, in some embodiments, the surface of the partially-fabricated device 300l may be further treated if the measured current of the conductive pattern 360 is greater than or equal to 1 nanoampere (nA). The surface of the partially-fabricated device 300l may be further treated in the same or similar way as the surface of the partially-fabricated device 300l is treated as described herein.

The fourth mask 352 may be removed in a variety of ways. In an example, the fourth mask 352 may be removed the same or similar way as the first mask 316 may be removed, the second mask 328 may be removed, and/or the third mask 338 may be removed. For example, the fourth mask 352 may be removed by soaking in a first fluid for a first time period, rinsing in a second fluid, drying with a gas, and baking at temperature for a second time period. In some embodiments, the first fluid may include a solvent, such as acetone. Moreover, in some embodiments, the first time period may be 5 minutes. Further, in some embodiments, the second fluid may include IPA. Further still, in some embodiments, the gas may include nitrogen. Moreover, in some embodiments, the temperature may be 90 degrees C. Further, in some embodiments, the second time period may be 2 minutes. As another example, the fourth mask 338 may be removed using an inductively coupled plasma, such as oxygen plasma.

After the fourth mask 352 is removed, a resistance of the conductive pattern 360 may be measured. The resistance of the conductive pattern 360 may be measured in a variety of ways. For example, the resistance of the conductive pattern 360 may be measured by applying a voltage source to the conductive pattern 360 and measuring a current of the conductive pattern 360. In some embodiments, the voltage source may be 10 V. Moreover, in some embodiments, the measured current of the conductive pattern 360 may be less than 1 nA.

Next, an electronic component 364 is mounted to the electrical contacts 348 to provide a partially-fabricated device 300n, as shown in FIG. 3n. The electronic component 364 could include, for example, one or more chips, such as an application-specific integrated circuits (ASIC), and one or more discrete electronic components, including capacitors, batteries, light emit diodes (LED), and/or photodiodes. Heat, pressure, a pick-and-place tool and a bonding medium (e.g., anisotropic conductive paste (ACP), anisotropic conductive film (ACF), solder and flux, solder paste, introducing underfill on solder bumps, etc.), ultra-sonic bonding, or a flip-chip bonder, for example, may be used to adhere a first surface 366 of the electronic component 364 to the electrical contacts 348. The electronic component 364 has a second surface 368 opposite the first surface 366.

In an example, the electronic component 364 may be mounted to the electrical contacts 348 by a tool with a force for a time period at a tool head temperature and a base temperature. In some embodiments, the force may be 1 newton (N). Moreover, in some embodiments, the time period may be 30 seconds. Further, in some embodiments, the tool head temperature may be 180 degrees C. Further still, in some embodiments, the base temperature may be 85 degrees C.

Moreover, the partially-fabricated device 300m may be cleaned before mounting the electronic component 364 to the electrical contacts 348. The partially-fabricated device 300m may be cleaned in a variety of ways. For example, the partially-fabricated device 300m may be cleaned by rinsing with a fluid, drying with a gas, and baking at temperature for a time period. In some embodiments, the fluid may include IPA. Moreover, in some embodiments, the gas may include nitrogen. Further, in some embodiments, the temperature may be 90 degrees C. Further still, in some embodiments, the time period may be 2 minutes.

Further still, the partially-fabricated device 300m may be plasma cleaned before mounting the electronic component 364 to the electrical contacts 348. The partially-fabricated device 300m may be plasma cleaned in a variety of ways. For example, the partially-fabricated device 300m may be plasma cleaned at a power for a time period. In some embodiments, the power may be high. Moreover, in some embodiments, the time period may be 2 minutes.

Although partially-fabricated device 300n has been described as including the electronic component 364 mounted to the electrical contacts 348, the partially-fabricated device 300n may include two or more electronic components mounted to the electrical contacts 348. The two or more electronic components may each take the form of or be similar in form to any of the electronic components described herein. In addition, the two or more electronic components may each be mounted to the electrical contacts 348 in the same or similar way as the electronic component 364 is mounted to the electrical contacts 348.

Next, a fifth mask 370 is formed on the first metal layer 332 to provide a partially-fabricated device 300o as shown in FIG. 3o. In some embodiments, the fifth mask 370 may be formed on part of or all of the first metal layer 332.

The fifth mask 370 may include a variety of materials. For example, the fifth mask 370 can be composed of the same material as the first mask 316, the second mask 328, the third mask 338, and/or the fourth mask 352. However, in other examples, the fifth mask 370 can be composed of a different material than the first mask 316, the second mask 328, the third mask 328, and/or the fourth mask 352.

Moreover, the fifth mask 370 may have a variety of thicknesses. In an example, the fifth mask 370 may have the same or similar thickness as the first mask 316, the second mask 328, the third mask 328, and/or the fourth mask 352. For example, the fifth mask 370 may have thicknesses of 5 micrometers. However, in other examples, the fifth mask 370 may have a thickness that is different than the thickness of the first mask 316, the thickness of the second mask 328, the thickness of the third mask 338, and/or the thickness of the fourth mask 352.

Further, in an example, the fifth mask 370 may be formed on the first metal layer 332 the same or similar way as the first mask 316 may be formed on the portion 318 of the first coating 314, the second mask 328 may be formed on the portion 330 of the seed layer 326, the third mask 338 may be formed on the first metal layer 332 and the portion 340 of the seed layer 326, and the fourth mask 352 may be formed on the first metal layer 332, the second metal layer 342, and the portion 354 of the seed layer 326. For example, the fifth mask 370 may be formed on the first metal layer 332 by spin coating and patterning.

The fifth mask 370 may be spin coated in a variety of ways. For example, a material may be spin coated by placing the material on the partially-fabricated device 300n, applying a spread cycle, applying a spin cycle, and applying a deceleration cycle.

In some embodiments, placing the material on the partially-fabricated device 300n may include pouring (or pipetting) the material onto the partially-fabricated device 300n.

Moreover, in some embodiments, applying the spread cycle may include rotating the partially-fabricated device 300n at a first rate for a first time period. And in such embodiments, the first rate may be 500 rpm. And in such embodiments, the first time period may be 8 seconds. With this arrangement, the material may be spread over the first metal layer 332. The spread cycle may further include accelerating the partially-fabricated device 300n at a second rate for a second time period before rotating the partially-fabricated device 300n at the first rate for the first time period. In some embodiments, the second rate may be 250 rpm per second. Moreover, in some embodiments, the second time period may be 2 seconds.

Further, in some embodiments, applying the spin cycle may include rotating the partially-fabricated device 300n at a first rate for a first time period. And in such embodiments, the first rate may be 3000 rpm. And in such embodiments, the first time period may be 38 seconds. With this arrangement, the thickness of the fourth mask 370 may be formed. The spin cycle may further include accelerating the partially-fabricated device 300n at a second rate for a second time period before rotating the partially-fabricated device 300n at the first rate for the first time period. In some embodiments, the second rate may be 1500 rpm per second. Moreover, in some embodiments, the second time period may be 2 seconds.

Further still, in some embodiments, applying the deceleration cycle comprises decelerating the partially-fabricated device 300n at a rate for a time period. And in such embodiments, the rate may be 1500 rpm per second. And in such embodiments, the time period may be 2 seconds.

Moreover, in some embodiments, the partially-fabricated device 300n may be placed in a vacuum chuck before placing the material on the partially-fabricated device 300n. And in such embodiments, the partially-fabricated device 300n may be removed from the vacuum chuck after applying the declaration cycle.

After the fifth mask 370 is spin coated, the fifth mask 370 may be baked before patterning. The fifth mask 370 may be baked in a variety of ways. For example, the fifth mask 370 may be baked at a temperature for a time period. In some embodiments, the temperature may be 90 degrees C. Moreover, in some embodiments, the time period may be 5 or 45 minutes. After the fifth mask 370 is baked, the fourth mask 370 may sit for a time period before further processing. In some embodiments, the time period is 5 or 45 minutes.

In addition, the fifth mask 370 may be patterned in a variety of ways. For example, a material may be patterned by exposing and developing. In such an example, the material may be exposed to light at an intensity for a first time period, and developed by soaking in a fluid for a second time period. In some embodiments, the light may be UV light that is generated by a mercury lamp. Moreover, in some embodiments, the intensity may be 19 mW/cm$^2$. Further, in some embodiments, the first time period may be 12 seconds. Moreover, in some embodiments, the fluid may comprise four parts DI water and one part a fluid comprising potassium borates. And in such embodiments, the fluid comprising potassium borates may be AZ® 400K Developer sold by AZ Electronics Materials. Further still, in some embodiments, the second time period may be about 3 minutes. In an example, after the fifth mask 370 is exposed, the fifth mask 370 may sit for a time period before the fifth mask 370 is developed. In some embodiments, the time period may be 15 minutes.

Further, the partially-fabricated device 300n may be cleaned before forming the fifth mask 370 on the first metal layer 332. The partially-fabricated device 300n may be cleaned in a variety of ways. For example, the partially-fabricated device 300n may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further still, the partially-fabricated device 300n may be baked before forming the fifth mask 370 on the first metal layer 332. The partially-fabricated device 300n may be baked at a temperature for a time period. In some embodiments, the temperature may be 90 degrees C. Moreover, in some embodiments, the time period may be 2 minutes. Further, in some embodiments, the partially-fabricated device 300n may be baked on a hot plate. After the partially-fabricated device 300n is baked, the partially-fabricated device 300n may be cooled to room temperature.

As shown in FIG. 3p, a second coating 374 is formed on the second bio-compatible layer 322, the electronic component 364, the antenna 346, the fifth mask 370, the electrical contacts 348, the electrical interconnects 350, and the electrical interconnects 358 to provide a partially-fabricated device 300p. With this arrangement, the second coating 374 is formed over the first coating 314 and the first bio-compatible layer 308. The second coating 374 may help to protect the bio-compatible device 300t from moisture.

In an example, the second coating 374 can be composed of the same material as the first coating 314. However, in other examples, the second coating 374 can be composed of a different material than the first coating 314. The second coating 314 may include any of the materials mentioned herein that the first coating 314 may include.

Moreover, the second coating 374 may have a variety of thicknesses. In an example, the second coating 374 may have the same or similar thickness as the first coating 314. For example, the second coating 374 may have a thickness between 1 to 150 micrometers, such as 30 nanometers. However, in other examples, the second coating 374 may have a thickness that is different than the thickness of the first coating 314.

Further, in an example, the second coating 374 may be formed on the second bio-compatible layer 322, the electronic component 364, the antenna 346, the sensor electrodes 336, the electrical contacts 348, the electrical interconnects 350, and the electrical interconnects 358 the same or similar way as the first coating 314 may be formed on the first bio-compatible layer 308. However, in other examples, the second coating 374 may be formed by a different process (or processes) than the process (or processes) used to form the first bio-compatible layer 308.

For example, the second coating 374 may be formed by microfabrication process such as atomic layer deposition. The second coating 374 may be formed on part of or all of the second bio-compatible layer 322, the electronic component 364, the antenna 346, the fifth mask 370, the electrical contacts 348, the electrical interconnects 350, and the electrical interconnects 358. For example, the second coating 374 may be deposited to create a continuous layer that spans the entirety of the second bio-compatible layer 322, the electronic component 364, the antenna 346, the fifth mask 370, the electrical contacts 348, the electrical interconnects 350, and the electrical interconnects 358. Alternatively, the second coating 374 may be deposited only in certain locations on the second bio-compatible layer 322, the electronic component 364, the antenna 346, the fifth mask 370, the electrical contacts 348, the electrical interconnects 350, and the electrical interconnects 358. In such an example, the second coating 374 may be patterned only in certain locations on the second bio-compatible layer 322, the electronic component 364, the antenna 346, the fifth mask 370, the electrical contacts 348, the electrical interconnects 350, and the electrical interconnects 358 using one or more masks. In addition, in some embodiments, the second coating 374 may be applied volumetrically.

Moreover, the partially-fabricated device 300o may be cleaned before forming the second coating 374 on the second bio-compatible layer 322, the electronic component 364, the antenna 346, the fifth mask 370, the electrical contacts 348, the electrical interconnects 350, and the electrical interconnects 358. The partially-fabricated device 300o may be cleaned in a variety of ways. For example, the partially-fabricated device 300o may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further, the partially-fabricated device 300o may be baked before forming the second coating 374 on the second bio-compatible layer 322, the electronic component 364, the antenna 346, the fifth mask 370, the electrical contacts 348, the electrical interconnects 350, and the electrical interconnects 358. The partially-fabricated device 300o may be baked at a temperature for a time period. In some embodiments, the temperature may be 90 degrees C. Moreover, in some embodiments, the time period may be 5 minutes. Further, in some embodiments, the partially-fabricated device 300o may be baked on a hot plate. After the partially-fabricated device 300o is baked, the partially-fabricated device 300o may be cooled to room temperature.

Further still, the partially-fabricated device 300o may be plasma cleaned before forming the second coating 374 on the first bio-compatible layer 308, the electrical contacts 358, the sensor electrodes 336, the fifth mask 370, the electronic component 364, the antenna 346, the electrical contacts 348, and/or the electrical interconnects 350. The partially-fabricated device 300o may be plasma cleaned in a variety of ways. For example, the partially-fabricated device 300o may be plasma cleaned at a power for a time period. In some embodiments, the power may be high. Moreover, in some embodiments, the time period may be 2 minutes.

In an example, a surface of the second bio-compatible layer 322 is treated, such as a surface 372 of the second bio-compatible layer 322 (as shown in FIG. 3o). With this arrangement, for example, the surface 372 may be roughened, such that adhesion of a coating to the first bio-compatible layer 308 may be improved. The surface 372 may be treated in a variety of ways. For example, the surface 372 may be treated by etching using an inductively coupled plasma at a power for a time. In some embodiments, the inductively coupled plasma may include an oxygen plasma. Moreover, in some embodiments, the power may be 400 W with a 300 W bias. In some examples, the inductively coupled plasma may unevenly etch the surface 372, such that the surface 372 may be roughened. Further, in some embodiments, the time period may be 30 seconds. Other plasmas and/or types of plasmas may be used as well, such as plasma asher, a reactive ion etcher, etc.

As shown in FIG. 3q, a third bio-compatible layer 378 is formed on the second coating 374 to provide a partially-fabricated device 300q. With this arrangement, the third bio-compatible layer 378 is formed over the first bio-compatible layer 308, the electronic component 364, the antenna 346, the sensor electrodes 336, the electrical contacts 348, the electrical interconnects 350, the electrical interconnects 358, and the etch stop 320. The third bio-compatible layer 378 defines a second side 380 of the bio-compatible device. That is, the second bio-compatible layer 378 defines an outer edge of the bio-compatible device.

In an example, the third bio-compatible layer 378 can be composed of the same polymeric material as the first bio-compatible layer 308 and/or the second bio-compatible layer 322. However, in other examples, the third bio-compatible layer 378 can be composed of a different polymeric material than the first bio-compatible layer 308 and/or the second bio-compatible layer 322. The third bio-compatible layer 378 can be any one of the polymeric materials mentioned herein that is both bio-compatible and electrically insulating. The third bio-compatible layer 378 thus serves to seal and insulate the assembled components.

Moreover, the third bio-compatible layer 378 may have a variety of thicknesses. For example, the third bio-compatible layer 378 may have a thickness between one or more embedded components and a surface of the third bio-compatible layer 378 between 5 to 100 micrometers, such as 10 micrometers. Other thicknesses of the third bio-compatible layer 378 are possible as well.

In an example, the third bio-compatible layer 378 may be formed in the same or similar way as the first bio-compatible layer 308 and/or the second bio-compatible layer 322. However, in other example, the third bio-compatible layer 378 may be formed by a different process (or processes) than the process (or processes) used to form the first bio-compatible layer 308 and/or the second bio-compatible 322.

For example, the third bio-compatible layer 378 may be formed by a microfabrication process such as chemical vapor deposition. The third bio-compatible layer 378 may be deposited on the second coating 374 to create a continuous layer that spans the entirety of the second coating 374. And in at least one such example, the third bio-compatible layer 378 may be a conformal coat. With this arrangement, the third bio-compatible layer 378 may be deposited to create a continuous layer that spans the entirety of the assembled components. For example, the third bio-compatible layer 378 can span a region that extends beyond a footprint of the assembled components. As a result, the assembled components can be surrounded by portions of the third bio-compatible layer 378 that rest over the first bio-compatible layer 308. Alternatively, the third bio-compatible layer 378 may be deposited only in certain locations on the second coating 374. In such an example, the third bio-compatible layer 378 be patterned in certain locations on the second coating 374 using one or more masks.

In an example, equipment that forms the third bio-compatible layer 378 may be preheated for around 1 hour before forming the third bio-compatible layer 378.

Moreover, the partially-fabricated device 300p may be cleaned before forming the third bio-compatible layer 378 on the second coating 374. The partially-fabricated device 300p may be cleaned in a variety of ways. For example, the partially-fabricated device 300p may be cleaned by rinsing in a fluid, drying with a gas, and baking at a temperature for a time period. In some embodiments, the fluid may include DI water. Moreover, in some embodiments, the gas may include nitrogen. Further, in some embodiments, the temperature may be 90 degrees C. Further still, in some embodiments, the time period may be 2 minutes.

In an example, a surface of the second coating 374 is treated, such as a surface 376 of the second coating 374 (as shown in FIG. 3p). With this arrangement, the surface 376 may be roughened, such that adhesion of third bio-compatible layer 378 to the second coating 374 may be improved. The surface 376 may be treated in a variety of ways. For example, the surface 376 may be treated by etching using an inductively coupled plasma at a power for a time. In some embodiments, the inductively coupled plasma may include an argon plasma and/or an oxygen plasma. Moreover, in some embodiments, the power may be 400 W with a 300 W bias. In some examples, the inductively coupled plasma may unevenly etch the surface 376, such that the surface 376 may be roughened. Further, in some embodiments, the time period may be 30 seconds. Other plasmas and/or types of plasmas may be used as well, such as plasma asher, a reactive ion etcher, etc.

Next, an etch mask 382 is formed over a portion 384 of the third bio-compatible layer 378 to provide a partially-fabricated device 300r, as shown in FIG. 3r. The etch mask 382 may include a variety of materials. For example, the etch mask 382 may include one or more photoresist layers, such as one photoresist layer comprising cyclopentanone. In such an example, the etch mask 382 may be KMPR® sold by Micro Chem. Further, in some examples, the etch mask may include one or more metal layers, such as one or more metal layers that include aluminum, titanium, and/or chromium. Further still, in some examples, the etch mask 382 may include one or more inorganic material layers, such as one or more inorganic material layers that include silicon oxide, aluminum oxide, and/or silicon nitride.

Moreover, the etch mask 382 may have a variety of thicknesses. For example, the etch mask 382 may have a thickness between 100 to 150 micrometers, such as 150 micrometers. Other thicknesses of the etch mask 382 are possible as well.

In an example, the etch mask 382 may be formed by spin coating and patterning. However, in other examples, the etch mask 382 may be formed by microfabrication processes such as evaporation and/or sputtering.

The etch mask 382 may be spin coated in a variety of ways. For example, the etch mask 382 may be spin coated in steps. In such an example, a first step may involve placing a first material on the partially-fabricated device 300q, applying a spread cycle, applying a spin cycle, and applying a deceleration cycle.

In some embodiments, placing the first material on the partially-fabricated device 300q may include pouring (or pipetting) the first material onto the partially-fabricated device 300q.

Moreover, in some embodiments, applying the spread cycle may include rotating the partially-fabricated device 300q at a first rate for a first time period. And in such embodiments, the first rate may be 500 rpm. And in such embodiments, the first time period may be 5 seconds. With this arrangement, the first material may be spread over the partially-fabricated device 300q. The spread cycle may further include accelerating the partially-fabricated device 300q at a second rate for a second time period before rotating the partially-fabricated device 300q at the first rate for the first time period. In some embodiments, the second rate may be 100 rpm per second. Moreover, in some embodiments, the second time period may be 5 seconds.

Further, in some embodiments, applying the spin cycle may include rotating the partially-fabricated device 300q at a first rate for a first time period. And in such embodiments, the first rate may be 1000 rpm. And in such embodiments, the first time period may be 118 seconds. With this arrangement, a first portion of the thickness of the etch mask 382 may be formed. The spin cycle may further include accelerating the partially-fabricated device 300q at a second rate for a second time period before rotating the partially-fabricated device 300q at the first rate for the first time period. In some embodiments, the second rate may be 500 rpm per second. Moreover, in some embodiments, the second time period may be 2 seconds.

Further still, in some embodiments, applying the deceleration cycle comprises decelerating the partially-fabricated device 300q at a rate for a time period. And in such embodiments, the rate may be 500 rpm per second. And in such embodiments, the time period may be 2 seconds.

Moreover, in some embodiments, the partially-fabricated device 300q may be placed in a vacuum chuck before placing the first material on the partially-fabricated device 300q.

The first step may further involve baking the first material at a temperature for a time period. In some embodiments, the temperature is 65 degrees C. Moreover, in some embodiments, the time period may be 10 minutes.

In such an example, a second step may involve placing a second material on the first material, applying a spread cycle, applying a spin cycle, and applying a deceleration cycle.

In some embodiments, placing the second material on the first material may include pouring (or pipetting) the second material onto the first material.

Moreover, in some embodiments, applying the spread cycle may include rotating the partially-fabricated device 300q at a first rate for a first time period. And in such embodiments, the first rate may be 500 rpm. And in such embodiments, the first time period may be 5 seconds. With this arrangement, the second material may be spread over the first material. The spread cycle may further include accelerating the partially-fabricated device 300q at a second rate for a second time period before rotating the partially-fabricated device 300q at the first rate for the first time period. In some embodiments, the second rate may be 100 rpm per second. Moreover, in some embodiments, the second time period may be 5 seconds.

Further, in some embodiments, applying the spin cycle may include rotating the partially-fabricated device 300q at a first rate for a first time period. And in such embodiments, the first rate may be 1000 rpm. And in such embodiments, the first time period may be 118 seconds. With this arrangement, a second portion of the thickness of the etch mask 382 may be formed. The spin cycle may further include accelerating the partially-fabricated device 300p at a second rate for a second time period before rotating the partially-fabricated device 300p at the first rate for the first time period. In some embodiments, the second rate may be 500 rpm per second. Moreover, in some embodiments, the second time period may be 2 seconds.

Further still, in some embodiments, applying deceleration cycle comprises decelerating the partially-fabricated device 300q at a rate for a time period. And in such embodiments, the rate may be 500 rpm per second. And in such embodiments, the time period may be 2 seconds.

And in some embodiments, the partially-fabricated device 300q may be removed from the vacuum chuck after applying the deceleration cycle.

After the first and second material is spin coated, the first and second material may be baked at a first temperature to a second temperature at a rate for a time period. In some embodiments, the first temperature is 65 degrees C. Moreover, in some embodiments, the second temperature is 90 degrees C. Further, in some embodiments, the rate is 120 degrees C. per hour. Further still, in some embodiments, the time period may around 15 minutes. In another example, the first and second material may then be baked at the second temperature for a second time period. In some embodiments, the second time period may be 105 minutes.

After the first and second material is baked, the first and second material may be cooled to room temperature at a rate. In some embodiments, the rate is 120 degrees C. per hour. After the first and second material are cooled, the first and second material may sit for a time period before further processing. In some embodiments, the time period may be 2 hours.

The etch mask may 382 be patterned in a variety of ways. For example, the first and second material may be patterned by exposing and developing. And, in such an example, the first and second material may be exposed and developed in steps.

In such an example, a first step may involve exposing the first and second material to light at an intensity for a first time period. In some embodiments, the light may be UV light that may be generated by a mercury lamp. Moreover, in some embodiments, the intensity may be the intensity may be 19 mW/cm². Further, in some embodiments, the first time period may be 70 seconds. Further still, in such an example, a second step may involve baking the first and second material at a temperature for a second time period. In some embodiments, the temperature may be 90 degrees C. Moreover, in some embodiments, the second time period may be 5 minutes. Further still, in such an example, a third step may involve developing the first and second material using a fluid comprising 1-methoxy-2-propyl acetate. In such an example, the fluid may be SU-8 Developer® sold by Micro Chem. In some embodiments, the time period may be 30 minutes. Moreover, in such an example, a fourth step may involve rinsing the first and second material in a fluid. In some embodiments, the fluid may be IPA.

Moreover, the partially-fabricated device 300r may be further processed after formation of the etch mask 382 over the portion 384 of the third bio-compatible layer 378. The partially-fabricated device 300r may be further processed in a variety of ways. For example, the partially-fabricated device 300r may be further processed by rinsing in a fluid, blow drying with a gas, and baking at a temperature for a time period. In some embodiments, the fluid may include IPA. Moreover, in some embodiments, the gas may include nitrogen. Further, in some embodiments, the temperature may be 90 degrees C. Further still, in some embodiments, the time period may be 60 minutes.

Moreover, the partially-fabricated device 300q may be cleaned before forming the etch mask 382 over the portion 384 of the third bio-compatible layer 378. The partially-fabricated device 300q may be cleaned in a variety of ways. For example, the partially-fabricated device 300q may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

Further, the partially-fabricated device 300q may be baked before forming the etch mask 382 over the portion 384 of the third bio-compatible layer 378. The partially-fabricated device 300q may be baked in a variety of ways. For example, the partially-fabricated device 300q may be baked at a temperature for a time period. In some embodiments, the temperature may be 90 degrees C. Moreover, in some embodiments, the time period may be 2 minutes. Further, in some embodiments, the partially-fabricated device 300q may be baked on a hot plate. After the partially-fabricated device 300q is baked, the partially-fabricated device 300q may be cooled to room temperature.

As shown in FIG. 3s, exposed portions 386 of the third bio-compatible layer 378 (i.e., the portions that are not covered by the etch mask 382) are etched using an etchant to provide a partially-fabricated device 300s. In an example, the etchant may be an inductively coupled plasma and the exposed portions 386 of the third bio-compatible layer 384 are etched using inductively coupled plasma at a power for a time period. In some embodiments, the inductively coupled plasma may include an oxygen plasma. Moreover, in some embodiments, the power may be 400 W at a 300 W bias. Further, in some embodiments, the time period may be 80 minutes. And, in such an example, the etching may comprise one or more cycles that comprises an etch period followed by a rest period, such that the partially-fabricated device 300r may cool down. In some embodiments, the etch period may be 2 minutes. Moreover, in some embodiments, the rest period may be 2 minutes. Further, in some embodiments, the one or more cycles may be 20 cycles. And, in some embodiments, the one or more cycles may be applied in sequence. Other plasmas and/or types of plasmas may be used as well, such as a plasma asher, a reactive ion etcher, etc.

In such an example, a first portion 386A of the exposed portions 386 of the third bio-compatible layer 378 that is located over the fifth mask 370 is etched to thereby form an opening 388 in the third bio-compatible layer 378, remove a portion of the second coating 374 that is located over the fifth mask, and remove the fifth mask 370 thereby exposing the sensor electrodes 336. In some embodiments, the opening 388 may have a dimension of between 500 to 700 micrometers. The opening 388 may have a variety of shapes, such as a square shape with rounded corners, a rectangular shape, a circular shape, etc.

The etch stop 320 inhibits etching of the first portion 323 of the first bio-compatible layer 308 by the etchant during the etching of the first portion 386A of the exposed portions 386 of the third bio-compatible layer 378. In some embodiments, the etch stop 320 may inhibit etching the first portion 323 by the etchant through the sensor electrodes 336. For example, as shown in FIG. 3s-2, the etch stop 320 may inhibit etching the first portion 323 by the etchant through the spacing between each of the fingers of the counter electrode 336B from a respective finger of the working electrode 336A. Additionally, the etch stop 320 may inhibit etching of a portion of the first coating 314 by the etchant during the etching of the first portion 386A of the exposed portions 386 of the third bio-compatible layer 378. For example, the etch stop 320 may inhibit etching of a portion of the first coating 314 that is covered by the etch stop 320 by the etchant.

Moreover, at least a portion of the seed layer 326B and/or at least a portion of the second bio-compatible layer 322 may be etched by the etchant during the etching of the exposed portions 386 of the third bio-compatible layer 386. For example, at least a portion of the seed layer 326B and/or at least some portions of the second bio-compatible layer 322 may be etched by the etchant through the spacing between each of the fingers of the counter electrode 336B from a respective finger of the working electrode 336A.

Further, in such an example, a second portion 386B of the exposed portions 386 of the third bio-compatible layer 378 (and portions of the second coating 374, the second bio-compatible layer 322, the first coating 314, and the first-bio-compatible layer 308 under the second portion 386B) is etched, such that a portion 304A of the sacrificial layer 304 is exposed. The portion 304A of the sacrificial layer 304 that is exposed may be referred to as a release region.

In other examples (not shown), when the second portion 386B of the exposed portions 386 of the third bio-compatible layer 378 (and portions of the second coating 374, the second bio-compatible layer 322, the first coating 314, and the first-bio-compatible layer 308 under the second portion 386B) is etched, the portion 304A of the sacrificial layer 304 may be etched.

Additionally, the etching of the second portion 386B of the exposed portions 386 of the third bio-compatible layer 378 (and portions the second coating 374, the second bio-compatible layer 322, the first coating 314, and the first-bio-compatible layer 308 under the second portion 386B) leaves excess material 390. With this approach, the etch mask 382 may define a shape 392 of the bio-compatible device 300t and/or a shape 394 of the antenna 346.

Further, as illustrated in FIG. 3s, at least a portion of the etch mask 382 is removed thereby leaving a portion 382B of the etch mask 382. In an example, the portion of the etch mask 382 is removed by the etchant that etches the exposed portions 384 of the third bio-compatible layer 378.

As shown in FIG. 3t, the portion 382B of the etch mask 382 is removed and the sacrificial layer 304 is removed to release the bio-compatible device 300t from the carrier substrate 302.

The portion 382B of the etch mask 382 may be removed in a variety of ways. For example, the portion 382B may be removed by soaking in a first fluid for a time period at a temperature and rinsing in a second fluid. In some embodiments, the first fluid may comprise n-methyl pyrrolidinone. And in such embodiments, the first fluid may be Remover PG® sold by Micro Chem. Moreover, in some embodiments, the time period may be 2 minutes. Further, in some embodiments, the temperature may be 90 degrees C. Further still, in some embodiments, the second fluid may include IPA.

Moreover, the sacrificial layer 304 may be removed in a variety of ways. For example, the sacrificial layer 304 may be removed by dissolving the sacrificial layer 304 in a fluid at a temperature for a time period. In some embodiments, the fluid may comprise nitric acid. And in such embodiments, the fluid may be Chromium Etchant 1020 sold by Transene Company. Moreover, in some embodiments, the temperature may be room temperature. Further, in some embodiments, the time period may be 6 to 10 hours. After the sacrificial layer 304 is dissolved, the bio-compatible device 300t may be rinsed with a fluid. In some embodiments, the fluid may be IPA.

In such an example, the sacrificial layer 304 may be dissolved in the fluid through the portion 304A of the sacrificial layer 304 that is exposed (or that was etched) when the second portion 386B of the exposed portions 386 of the third bio-compatible layer 358 (and the portions of the second coating 374, the second bio-compatible layer 322, the first coating 314, and the first-bio-compatible layer 308 under the second portion 386B) is etched. As another example, the sacrificial layer 304 may be removed by etching (e.g., wet etching) using an etchant that might not etch the third bio-compatible layer 378, the second coating 374, the second bio-compatible layer 322, the first coating 314, the first bio-compatible layer 308, and/or the conductive pattern 360.

After the bio-compatible device 300t is released from the carrier substrate 302, the bio-compatible device 300t may be rinsed in a fluid. In some embodiments, the fluid may include DI water.

As illustrated in FIG. 3t, the bio-compatible device 300t includes the first bio-compatible layer 308, the first coating 314, the second bio-compatible layer 322, the antenna 346, the electrical contacts 348, the electrical interconnects 350, the electrical interconnects 358, the sensor electrodes 336, the second coating 374, the third bio-compatible layer 378, the opening 388, the first side 312 of the bio-compatible device, and the second side 380 of the bio-compatible device. The first bio-compatible layer 308, the first coating 314, the second bio-compatible layer 322, the second coating 374, and the third bio-compatible layer 378 encapsulate the assembled components, except that the sensor electrodes 336 are exposed by the opening 388.

The bio-compatible device 300t is suitable for incorporation into a biological environment, such as within a body-mountable device or an implantable medical device, for example. Due to the encapsulating bio-compatible material, the surrounding environment is sealed from the embedded components. For example, if the bio-compatible device 300t is implanted in a biological host, or placed in an eye-mountable device to be exposed to tear fluid, the bio-compatible device 300t is able to be exposed to fluids of the biological host (e.g., tear fluid, blood, etc.), because the entire exterior surface is coated with bio-compatible material, except that the sensor electrodes 336 are exposed to allow detection of one or more analytes in the fluid.

The description in FIGS. 3a-t describes one example of a process for fabricating a bio-compatible device that can be embedded in an eye-mountable device. However, the process described with reference to FIGS. 3a-t may be employed to create bio-compatible devices for other applications, such as other mountable devices or implantable electronic medical device applications. Such implantable electronic medical devices may include an antenna for communicating information (e.g., sensor results) and/or inductively harvesting energy (e.g., radio frequency radiation). Implantable electronic medical devices may also include electrochemical sensors or they may include other electronic devices. The process described with reference to FIGS. 3a-t may be used to create bio-compatible devices suitable to be mounted on or in another part of the body, such as the skin, a tooth, or on a tissue in the mouth, for example.

The description in FIGS. 3a-t describes one example of a process for fabricating a bio-compatible device. Numerous variations to the example process described above are possible. For instance, the arrangement of a first coating, an etch stop, and a second bio-compatible layer in a bio-compatible device may take various different forms in various different embodiments.

For example, in some embodiments, in the bio-compatible device 300t the etch stop 320 may be formed on the first bio-compatible layer 308, the first coating 314 may be formed on the etch stop 320 and the first bio-compatible layer 308, and the second bio-compatible layer 322 may be formed on the first coating 314. Moreover, in some embodiments, in the bio-compatible device 300t the etch stop 320 may be formed on the first bio-compatible layer 308, the second bio-compatible layer 322 may be formed on the etch stop 320 and the first bio-compatible layer 320, and the first coating 314 may be formed on the second bio-compatible layer 322.

Figure 4A:
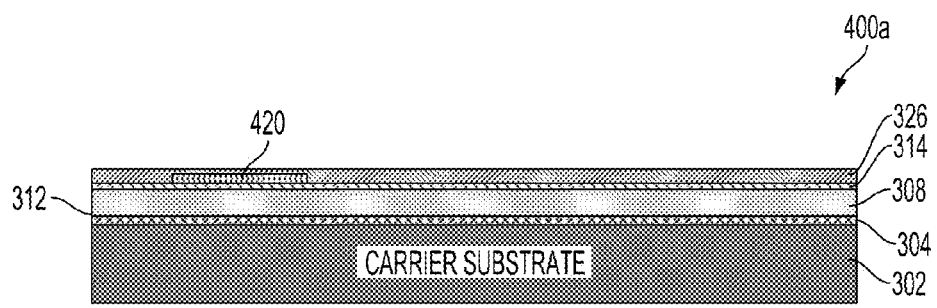
FIGS. 4a and 4b show other stages of fabricating a bio-compatible device, according to an example embodiment.
Figure 4B:
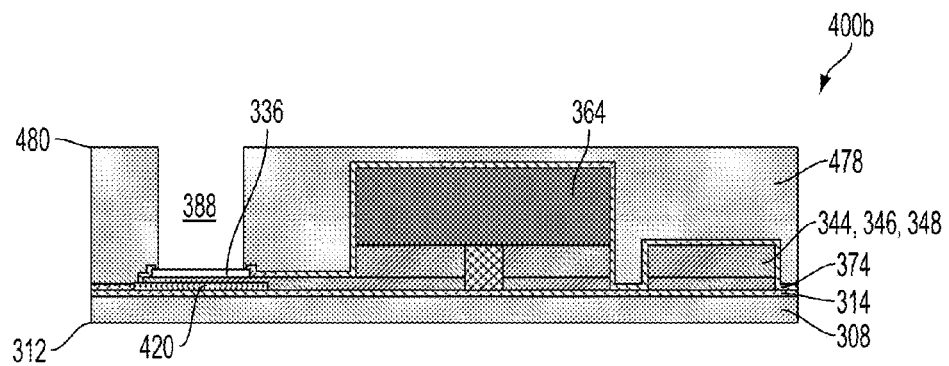

Further, in some examples, a bio-compatible device may not include three bio-compatible layers. Instead, in such examples, a bio-compatible device may include two bio-compatible layers. FIGS. 4a and 4b illustrate two stages of a process for forming a bio-compatible device, such as a bio-compatible device 400b shown in FIG. 4b. As shown in FIG. 4a, the seed layer 326 is formed on the etch stop 320 and the first coating 314 to provide a partially-fabricated device 400a. The seed layer 326 may be formed on an etch stop 420 and the first coating 314 the same or similar way as the seed layer 326 may be formed on the second bio-compatible layer 322 as described with reference to FIG. 3g. In such an example, the etch stop 420 may be composed of any of the non-conductive materials that the etch stop 320 may include. In addition, the etch stop 420 may have the same or similar thickness as the etch stop 320.

Further, as illustrated in FIG. 4a, the partially-fabricated device 400a includes the carrier substrate 302, the sacrificial layer 304, the first bio-compatible layer 308, the first coating 314, and the etch stop 420. In such an example, the sacrificial layer 304, the first bio-compatible layer 308, the first coating 314, and the etch stop 420 may be formed the same or similar way as the sacrificial layer 304, the first bio-compatible layer 308, the first coating 314, and the etch stop 320 may be formed as described with reference to FIGS. 3a-e.

As shown in FIG. 4b, the bio-compatible device 400b is released from the carrier substrate 302. The bio-compatible device 400b may be released from the carrier substrate 302 in the same or similar way as the bio-compatible device 300t may be released from the carrier substrate 302 as described with reference to FIG. 3t.

Further, as illustrated in FIG. 4b, the bio-compatible device 400b includes the first bio-compatible layer 308, the first coating 314, the antenna 346, the electrical contacts 348, the electrical interconnects 350, the electrical interconnects 358, the sensor electrodes 336, the second coating 374, a second bio-compatible layer 478, the opening 388, the first side 312 of the bio-compatible device, and a second side 480 of the bio-compatible device.

In such an example, the second bio-compatible layer 478 may take the form of or be similar in form to the third bio-compatible layer 378. The second bio-compatible layer 478 defines the second side 480 of the bio-compatible device. The second side 480 of the bio-compatible device may take the form of or be similar in form to the second side 380 of the bio-compatible device.

Moreover, in such an example, the antenna 346, the electrical contacts 348, the electrical interconnects 350, the electrical interconnects 358, the sensor electrodes 336, the electronic component 364, the second coating 374, the second bio-compatible layer 478, the opening 388 may be formed in the same or similar way as the antenna 346, the electrical contacts 348, the electrical interconnects 350, the electrical interconnects 358, the sensor electrodes 336, the second coating 374, the third bio-compatible layer 378, and the opening 388 may formed as described with reference to FIGS. 3h-3s.

Figure 5:
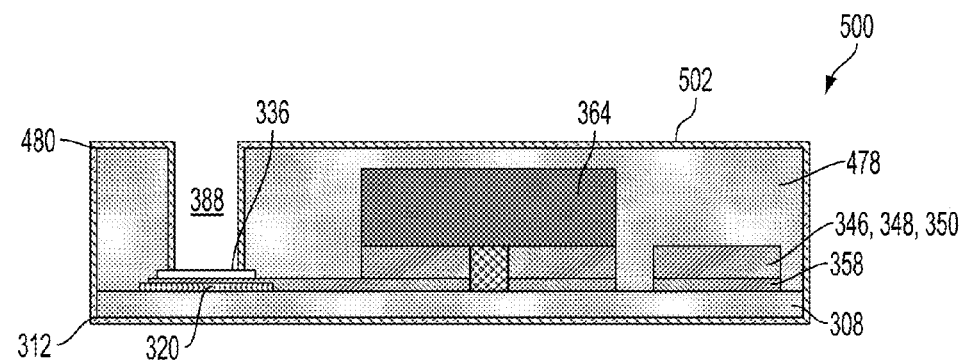
FIG. 5 shows forming a coating over a bio-compatible device, according to an example embodiment.

Further still, in some examples, a bio-compatible device may not include a first coating and/or a second coating. Instead, in such examples, a coating may be formed on at least a portion of the bio-compatible device. FIG. 5 illustrates a coating 502 formed on the bio-compatible device 500, according to an example embodiment. The coating 502 may help to protect the bio-compatible device 500 from moisture.

As illustrated in FIG. 5, the bio-compatible device 500 includes the first bio-compatible layer 308, the antenna 346, the electrical contacts 348, the electrical interconnects 350, the electrical interconnects 358, the sensor electrodes 336, the second bio-compatible layer 478, the opening 388, the first side 312 of the bio-compatible device, and a second side 480 of the bio-compatible device.

In an example, the coating 502 can be composed of the same material as the first coating 314 and/or the second coating 374 of the bio-compatible device. However, in other examples, the coating 502 can be composed of a different material than the first coating 314 and the second coating 374. The coating 502 may include any of the materials mentioned herein that the first coating 314 and the second coating 374 may include.

Moreover, the coating 502 may have a variety of thicknesses. In an example, the coating 502 may have the same or similar thickness as the first coating 314 and/or the second coating 374. For example, the coating 502 may have a thickness between 1 to 150 micrometers, such as 30 nanometers. However, in other examples, the coating 502 may have a thickness that is different than the thickness of the first coating 314 and the second coating 374.

In an example, the coating 502 may be formed by microfabrication process such as atomic layer deposition. The coating 502 may be formed on part of or all of the bio-compatible device 400b. For example, the coating 502 may be deposited to create a continuous layer that spans the entirety of the bio-compatible device 500. Alternatively, the coating 502 may be deposited only in certain locations on the bio-compatible device 500, such as certain locations on the first bio-compatible layer 308 and/or the second bio-compatible layer 478. In such an example, the coating 502 may be patterned only in certain locations on the bio-compatible device 500 using one or more masks. The sensor electrodes 336 may be covered by a mask during formation of the coating 502.

Moreover, the bio-compatible device 500 may be cleaned before forming the coating 502. The bio-compatible device 500 may be cleaned in a variety of ways. For example, the bio-compatible device 500 may be cleaned by soaking in a first fluid, rinsing in a second fluid, and drying with a gas. In some embodiments, the first fluid may include a solvent, such as acetone. Moreover, in some embodiments, the second fluid may include IPA. Further, in some embodiments, the gas may include nitrogen.

In an example, a surface of the first bio-compatible layer 308 and/or the second bio-compatible layer 478 is treated. With this arrangement, the surface may be roughened, such that adhesion of the coating 502 to the bio-compatible device 500 may be improved. The surface may be treated in a variety of ways. For example, the surface may be treated by etching using an inductively coupled plasma at a power for a time. In some embodiments, the inductively coupled plasma may include an argon plasma and/or an oxygen plasma. Moreover, in some embodiments, the power may be 400 W with a 300 W bias. In some examples, the inductively coupled plasma may unevenly etch the surface, such that the surface may be roughened. Further, in some embodiments, the time period may be 30 seconds. Other plasmas and/or types of plasmas may be used as well, such as plasma asher, a reactive ion etcher, etc.

In some embodiments, the coating 502 may be formed on at least a portion of the bio-compatible device 500 after the bio-compatible device 500 is released from a carrier substrate, such as the carrier substrate 302. However, in other embodiments, the bio-compatible device 500 may be conformed to a curvature of a polymer and the coating 502 may then be formed on at least a portion of the bio-compatible device 500. After the coating 502 is formed on the bio-compatible device 500, the bio-compatible device 500 may then be embedded in the polymer. For example, when conforming the bio-compatible device 500 to a curvature of a polymer involves bending the bio-compatible device 500 to the curvature of the polymer, the coating 502 may be formed on the bio-compatible device 500 after the bio-compatible device 500 is bent to the curvature of the polymer.

The arrangement of the first bio-compatible layer 308, the antenna 346, the electrical contacts 348, the electrical interconnects 350, the electrical interconnects 358, the sensor electrodes 336, the second bio-compatible layer 478, the opening 388, the first side 312 of the bio-compatible device, and a second side 480 of the bio-compatible device in the bio-compatible device 500 may be the same as or similar to the arrangement of the first bio-compatible layer 308, the antenna 346, the electrical contacts 348, the electrical interconnects 350, the electrical interconnects 358, the sensor electrodes 336, the second bio-compatible layer 478, the opening 388, the first side 312 of the bio-compatible device, and a second side 480 of the bio-compatible device in the bio-compatible device 400b.

Although the coating 502 has been described above as being formed on the bio-compatible device 500, the coating 502 may be formed on other bio-compatible devices as well.

For instance, the coating 502 may be formed on a bio-compatible device that includes three bio-compatible layers, such as the first bio-compatible layer 308, the second bio-compatible layer 322, and the third bio-compatible layer 378. Such a bio-compatible device may be similar in form to the bio-compatible device 500, except that such a bio-compatible device may not include the first coating 314 and/or the second coating 374.

For example, the coating 502 may be formed on a bio-compatible device that includes the first bio-compatible layer 308, the second bio-compatible layer 322, the antenna 346, the electrical contacts 348, the electrical interconnects 350, the electrical interconnects 358, the sensor electrodes 336, the third bio-compatible layer 378, and the opening 388.

Moreover, in some examples, a mask (e.g., the fifth mask 370) may not be formed on part of or all of a first metal layer (e.g., the first metal layer 332) during fabrication of a bio-compatible device. Instead, in such examples, a second coating (e.g., the second coating 374) may be formed on the first metal layer during fabrication of the bio-compatible device.

Further, in some examples, an etch stop (e.g., the etch stop 320) may not be formed over portion of a first bio-compatible layer (e.g., the first portion 323 of the first bio-compatible layer 308) during fabrication of a bio-compatible device. Instead, in some such examples, an etch stop or a protective layer may be formed over the sensor electrodes (e.g., the sensor electrodes 336). In addition, in such examples, at least a portion of the etch stop or the protective layer may be removed when a portion of a second bio-compatible layer is etched (e.g., the first portion 386A of the third bio-compatible layer 378) and any remaining portion of the etch stop or the protective layer may be removed to thereby expose the sensor electrodes.

In such examples, the etch stop and/or the protective layer may be similar in form to the etch stop 320. For example, the etch stop and/or the protective layer may include any of the materials that the etch stop 320 may include, and the etch stop and/or the protective layer may include any of the thicknesses that the etch stop 320 may include.

Moreover, in some embodiments, the etch stop and/or the protective layer may include one or more photoresist layers, such as a photoresist layer comprising 2-ethoxyethyl acetate. Further, in some embodiments, the etch stop and/or the protective layer may have thickness of 40 micrometers. Further still, in some embodiments, any remaining portion of the etch stop and/or the protective layer may be configured to be removed by dissolution in a fluid, such as a fluid comprising 2-ethoxyethyl acetate. Moreover, in some embodiments, any remaining portion of the etch stop and/or the protective layer may be removed by etching.

For instance, such an example may involve forming the first bio-compatible layer 308; forming the conductive pattern 360 over the first bio-compatible layer 308; forming an etch stop or a protective layer on the sensor electrodes 336, such that the sensor electrodes 336 are covered by the etch stop or the protective layer; mounting the electronic component 364 to the electrical contacts 348; forming the third bio-compatible layer 378 over the first bio-compatible layer 308, the electronic component 364, the antenna 346, the etch stop or the protective layer, the electrical contacts 348, the electrical interconnects 350, and the electrical interconnects 358; removing the first portion 386A of the third bio-compatible layer 378 to form the opening 388 and at least a portion of the etch stop or the protective layer; and removing any remaining portion of the etch stop or the protective layer to thereby expose the sensor electrodes 336.

In some such examples, the first coating 314 and the second coating 374 may be formed in the same or similar way as described with reference to FIGS. 3c and 3p. Moreover, in some such examples, the coating 502 may be formed in the same or similar way as described with reference to FIG. 5.

Further, in some examples, an etch stop may not be formed during the fabrication of a bio-compatible device. Instead, in some such examples, a bio-compatible layer (e.g., the third bio-compatible layer 378) may be formed over a conductive pattern (e.g., the conductive pattern 360), except for sensor electrodes (e.g., the sensor electrodes 336). In some embodiments, the bio-compatible may be formed over the conductive pattern, except for the sensor electrodes by spin coating and patterning.

For instance, such an example may involve forming the first bio-compatible layer 308; forming the conductive pattern 360 over the first bio-compatible layer 308; mounting the electronic component 364 to the electrical contacts 348; and forming the third bio-compatible layer 378 over the first bio-compatible layer 308, the electronic component 364, the antenna 346, the electrical contacts 348, the electrical interconnects 350, and the electrical interconnects 358.

In some such examples, the first coating 314 and the second coating 374 may be formed in the same or similar way as described with reference to FIGS. 3c and 3p. Moreover, in some such examples, the coating 502 may be formed in the same or similar way as described with reference to FIG. 5.

As another example, a first bio-compatible layer (e.g., the first bio-compatible layer 308) may be a different material from a second bio-compatible layer (e.g., the third bio-compatible layer 378) formed over the first bio-compatible layer and a conductive pattern (e.g., the conductive pattern 360). With this arrangement, when a portion of the second bio-compatible layer is etched (e.g., the first portion 386A of the third bio-compatible layer 378), the material of the first bio-compatible layer may inhibit etching of the first bio-compatible layer by the etchant. In some embodiments, the first bio-compatible layer may include polyimide and the second bio-compatible layer may include paralyene.

For instance, such an example may involve forming the first bio-compatible layer 308; forming the conductive pattern 360 over the first bio-compatible layer 308; mounting the electronic component 364 to the electrical contacts 348; forming the third bio-compatible layer 378 over the first bio-compatible layer 308, the electronic component 364, the antenna 346, the sensor electrodes 336, the electrical contacts 348, the electrical interconnects 350, and the electrical interconnects 358; etching, using an etchant, the first portion 386A of the third bio-compatible 378 to form the opening 388, wherein a material of the first bio-compatible layer 308 inhibits etching of the first bio-compatible layer 308 by the etchant.

In some such examples, the first coating 314 and the second coating 374 may be formed in the same or similar way as described with reference to FIGS. 3c and 3p. Moreover, in some such examples, the coating 502 may be formed in the same or similar way as described with reference to FIG. 5.

Figure 6:
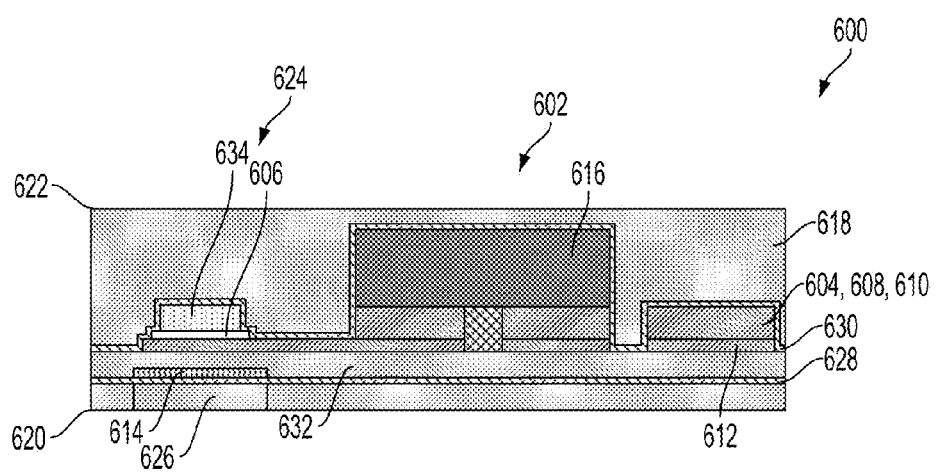
FIG. 6 shows a device, according to an example embodiment.

FIGS. 6-13 show example devices (or partially-fabricated devices) or example bio-compatible devices. For instance, FIG. 6 illustrates a device 600, according to an example embodiment. In particular, the device 600 includes a conductive pattern 602. The conductive pattern 602 defines an antenna 604, sensor electrodes 606, electrical contacts 608, electrical interconnects 610, and electrical interconnects 612. In addition, the device 600 includes an etch stop 614. As shown in FIG. 6, the sensor electrodes 606 are located over the etch stop 614.

Moreover, the device 600 further includes an electronic component 616 that is mounted to electrical contacts 608. Further, the device 600 further includes a bio-compatible layer 618 over the electronic component 616, the antenna 604, the sensor electrodes 606, the electrical contacts 608, the electrical interconnects 610, the electrical interconnects 612, and the etch stop 614. The bio-compatible layer 618 defines a first side 620 and a second side 622 of a bio-compatible device.

In another aspect, a first portion 624 of the bio-compatible layer 618 may be configured to be etched by an etchant to form an opening in the bio-compatible layer 618 and thereby expose the sensor electrodes 606. In some embodiments, the etch stop 614 may configured to inhibit etching of a second portion 626 of the bio-compatible layer 618 by the etchant. As shown in FIG. 6, the etch stop 614 is located over the second portion 626 of the bio-compatible layer 618.

In another aspect, the device 600 may further include a first coating 628 and a second coating 630. As shown in FIG. 6, the conductive pattern 602 is located over the first coating 628 and the second coating 630 is located over the conductive pattern 602 and the electronic component 616. Moreover, as shown in FIG. 6, a third portion 632 of the bio-compatible layer 618 is located between the first coating 628 and the second coating 630.

In yet another aspect, the device 600 may further include a mask 634. As shown in FIG. 6, the mask 634 is located over the sensor electrodes 606. In some embodiments, the mask 634 may be configured to be removed when the portion 624 of the bio-compatible layer 618 is etched.

In some embodiments, the conductive pattern 602 may take the form of or be similar in form to the conductive pattern 360, the antenna 604 may take the form of or be similar in form to the antenna 346, the sensor electrodes 606 may take the form of or be similar in form to the sensor electrodes 336, the electrical contacts 608 may take the form of or be similar in form to the electrical contacts 348, the electrical interconnects 610 may take the form of or be similar in form to the electrical interconnects 350, the electrical interconnects 612 may take the form of or be similar in form to the electrical interconnects 358, the etch stop 614 may take the form of or be similar in form to the etch stop 320, the electronic component 616 may take the form of or be similar in form to the electronic component 364, the bio-compatible layer 618 may take the form of or be similar in form to the first bio-compatible layer 308, the second bio-compatible layer 322, and the third bio-compatible layer 374, the first side 620 of the bio-compatible device may take the form of or be similar in form to the first side 312 of the bio-compatible device, the second side 622 of the bio-compatible device may take the form of or be similar in form to the second side 380 of the bio-compatible device, the first portion 624 of the bio-compatible layer 618 may take the form of or be similar in form to the first portion 386A of the exposed portions 386 of the third bio-compatible layer 378, the second portion 626 of the bio-compatible layer 618 may take the form of or be similar in form to the first portion 323 of the first bio-compatible layer 308, the first coating 628 may take the form or be similar in form to the first coating 314, the second coating 630 may take the form of or be similar in form to second coating 374, the third portion 632 of the bio-compatible layer 318 may take the form of or be similar in form to the second bio-compatible layer 322, and the mask 632 may take the form of or be similar in form to the fifth mask 370.

Figure 7A:
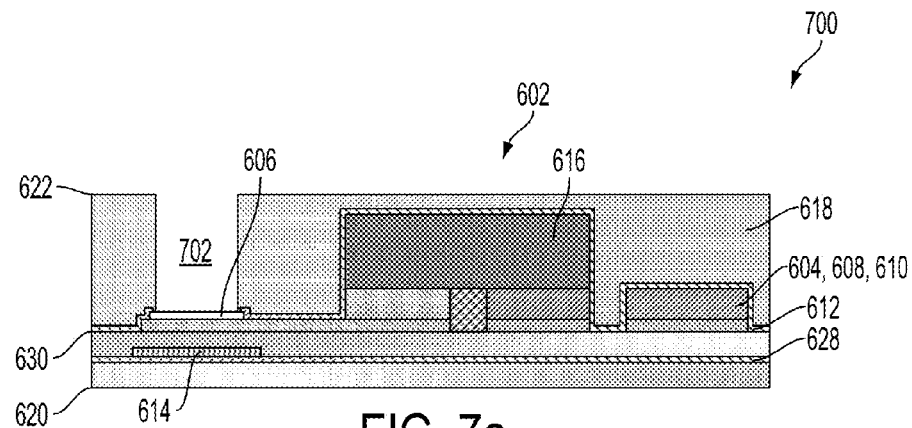
FIG. 7a shows a bio-compatible device, according to an example embodiment.

FIG. 7a illustrates a bio-compatible device 700, according to an example embodiment. In particular, the bio-compatible device 700 includes an opening 702 in the bio-compatible layer 618. As shown in FIG. 7a, the opening 702 is located over the sensor electrodes 606. The sensor electrodes 606 may be configured to receive one or more analytes via the opening 702.

Moreover, as shown in FIG. 7a, the bio-compatible device 700 includes the conductive pattern 602, the antenna 604, the electrical contacts 608, the electrical interconnects 610, the electrical interconnects 612, the etch stop 614, the electronic component 616, the first side 620 of the bio-compatible device, the second side 622 of the bio-compatible device, the first coating 628, and the second coating 630.

Figure 7B:
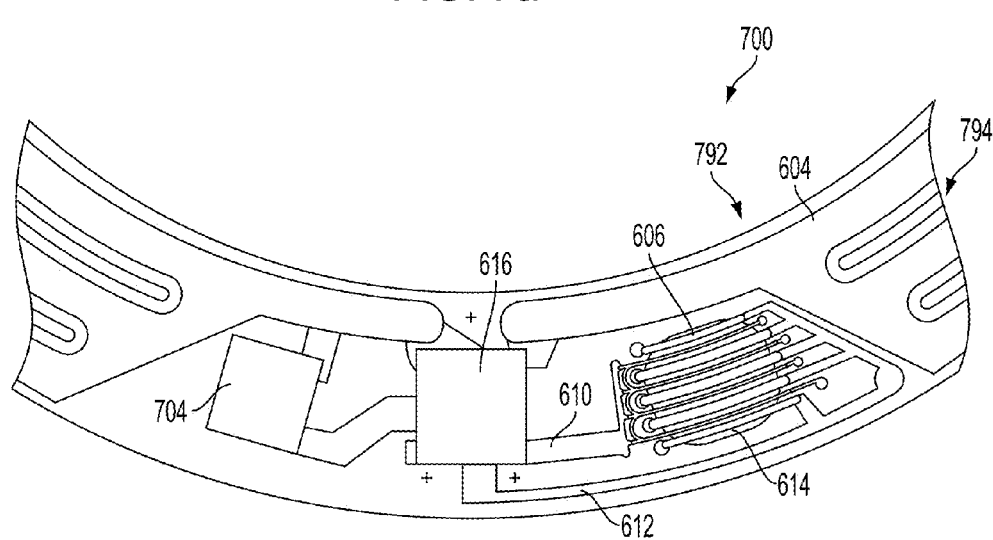
FIG. 7b shows a partial top view of a bio-compatible device, according to an example embodiment.

FIG. 7b illustrates a top view of a portion of the bio-compatible device 700, according to an example embodiment. As shown in FIG. 7b, the antenna 604 is electrically connected to the electronic component 616 via the electrical interconnects 610 and the sensor electrodes 606 are electrically connected to the electronic component 616 via the electrical interconnects 610. In other examples, the antenna 604 may be electrically connected to the electronic component 616 via the electrical interconnects 612 and/or the sensor electrodes 606 may be electrically connected to the electronic component 616 via the electrical interconnects 612. Moreover, in the illustrated example, the bio-compatible device 700 may include another electronic component 704. The electronic component 704 may take the form of or be similar in form to the electronic component 616. Further, as shown in FIG. 7b, the bio-compatible device 700 has a shape 792 and the antenna 646 has a shape 794. In addition, as shown in FIG. 7b, the etch stop 614 is visible through the interdigitated arrangement of the sensor electrodes 606.

The arrangement of the conductive pattern 602, the antenna 604, the sensor electrodes 606, the electrical contacts 608, the electrical interconnects 610, the electrical interconnects 612, the etch stop 614, the electronic component 616, the bio-compatible layer 618, the first side 620 of the bio-compatible device, the second side 622 of the bio-compatible device, the first coating 628, and the second coating 630 in the bio-compatible device 700 may be the same as or similar to the arrangement of the conductive pattern 602, the antenna 604, the sensor electrodes 606, the electrical contacts 608, the electrical interconnects 610, the electrical interconnects 612, the etch stop 614, the electronic component 616, the bio-compatible layer 618, the first side 620 of the bio-compatible device, the second side 622 of the bio-compatible device, the first coating 628, and the second coating 630 in the device 600.

Figure 8:
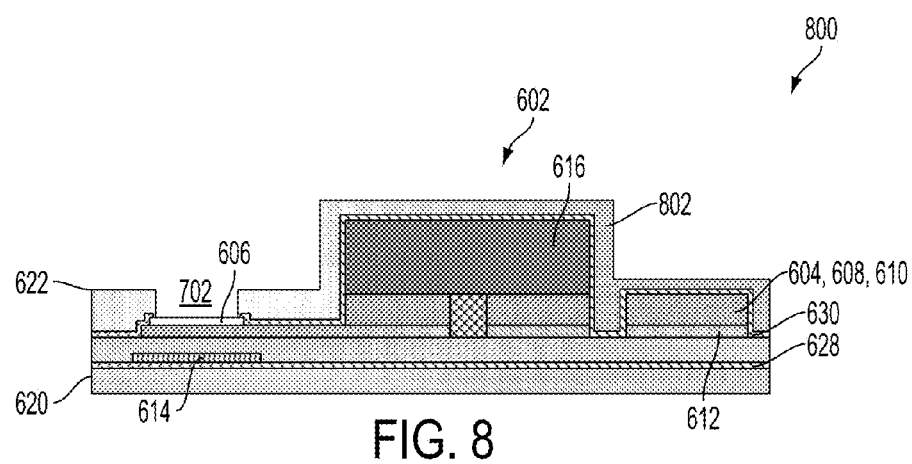
FIG. 8 shows another bio-compatible device, according to an example embodiment.

FIG. 8 illustrates another bio-compatible device 800, according to an example embodiment. In particular, the bio-compatible device 800 includes a bio-compatible layer 802. In the bio-compatible device 800, the opening 702 is in the bio-compatible layer 802.

As shown in FIG. 8, the bio-compatible device 800 includes the conductive pattern 602, the antenna 604, the sensor electrodes 606, the electrical contacts 608, the electrical interconnects 610, the electrical interconnects 612, the etch stop 614, the electronic component 616, the first side 620 of the bio-compatible device, the second side 622 of the bio-compatible device, the first coating 628, and the second coating 630. Moreover, as shown in FIG. 8, the bio-compatible layer 802 may include a conformal coat over the conductive pattern 602, the antenna 604, the electrical contacts 608, the electrical interconnects 610, the electrical interconnects 612. The bio-compatible layer 802 may be similar in form to the bio-compatible layer 618.

The arrangement of the conductive pattern 602, the antenna 604, the sensor electrodes 606, the electrical contacts 608, the electrical interconnects 610, the electrical interconnects 612, the etch stop 614, the electronic component 616, the bio-compatible layer 802, the first side 620 of the bio-compatible device, the second side 622 of the bio-compatible device, the first coating 628, the second coating 630, and the opening 702 in the bio-compatible device 800 may be the same as or similar to the arrangement of the conductive pattern 602, the antenna 604, the sensor electrodes 606, the electrical contacts 608, the electrical interconnects 610, the electrical interconnects 612, the etch stop 614, the electronic component 616, the bio-compatible layer 618, the first side 620 of the bio-compatible device, the second side 622 of the bio-compatible device, the first coating 628, the second coating 630, and the opening 702 in the bio-compatible device 700.

Figure 9:
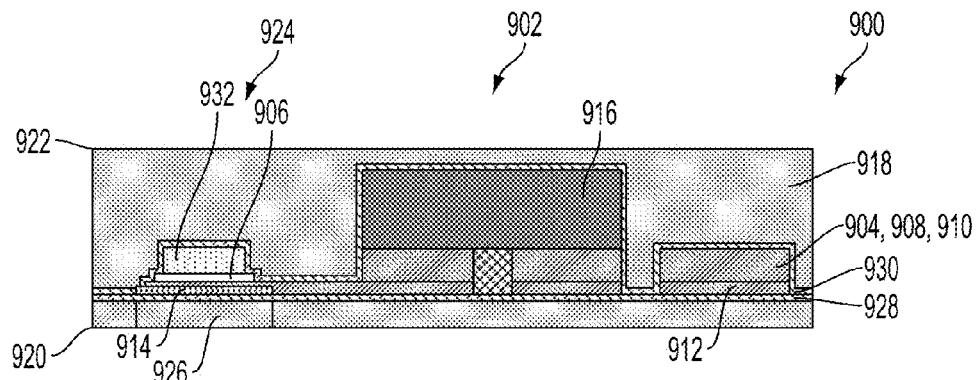
FIG. 9 shows another device, according to an example embodiment.

FIG. 9 illustrates another device 900, according to an example embodiment. In particular, the device 900 includes a conductive pattern 902. The conductive pattern 902 defines an antenna 904, sensor electrodes 906, electrical contacts 908, electrical interconnects 910, and electrical interconnects 912. In addition, the device 900 includes an etch stop 914. As shown in FIG. 9, the sensor electrodes 906 are located over the etch stop 914.

Moreover, the device 900 further includes an electronic component 916 that is mounted to electrical contacts 908. Further, the device 900 further includes a bio-compatible layer 918 over the electronic component 916, the antenna 904, the sensor electrodes 906, the electrical contacts 908, the electrical interconnects 910, the electrical interconnects 912, and the etch stop 914. The bio-compatible layer 918 defines a first side 920 and a second side 922 of a bio-compatible device.

In another aspect, a first portion 924 of the bio-compatible layer 918 may be configured to be etched by an etchant to form an opening in the bio-compatible layer 918 and thereby expose the sensor electrodes 906. In some embodiments, the etch stop 914 may configured to inhibit etching of a second portion 926 of the bio-compatible layer 918 by the etchant. As shown in FIG. 9, the second portion 926 of the bio-compatible layer 918 is located over the etch stop 914.

In another aspect, the device 900 may further include a first coating 928 and a second coating 930. As shown in FIG. 9, the conductive pattern 902 is located over the first coating 928 and the second coating 930 is located over the conductive pattern 902 and the electronic component 916.

In yet another aspect, the device 900 may further include a mask 932. As shown in FIG. 9, the mask 932 is located over the sensor electrodes 906. In some embodiments, the mask 932 may be configured to be removed when the portion 924 of the bio-compatible layer 918 is etched.

In some embodiments, the conductive pattern 902 may take the form of or be similar in form to the conductive pattern 360, the antenna 904 may take the form of or be similar in form to the antenna 346, the sensor electrodes 906 may take the form of or be similar in form to the sensor electrodes 336, the electrical contacts 908 may take the form of or be similar in form to the electrical contacts 348, the electrical interconnects 910 may take the form of or be similar in form to the electrical interconnects 350, the electrical interconnects 912 may take the form of or be similar in form to the electrical interconnects 358, the etch stop 914 may take the form of or be similar in form to the etch stop 320, the electronic component 616 may take the form of or be similar in form to the electronic component 364, the bio-compatible layer 918 may take the form of or be similar in form to the first bio-compatible layer 308 and the second bio-compatible layer 478, the first side 920 of the bio-compatible device may take the form of or be similar in form to the first side 312 of the bio-compatible device, the second side 922 of the bio-compatible device may take the form of or be similar in form to the second side 380 of the bio-compatible device, the first portion 924 of the bio-compatible layer 918 may take the form of or be similar in form to the first portion 386A of the exposed portions 386 of the third bio-compatible layer 378, the second portion 926 of the bio-compatible layer 918 may take the form of or be similar in form to the first portion 323 of the first bio-compatible layer 308, the first coating 928 may take the form or be similar in form to the first coating 314, the second coating 930 may take the form of or be similar in form to second coating 374, and the mask 932 may take the form of or be similar in form to the fifth mask 370.

Figure 10:
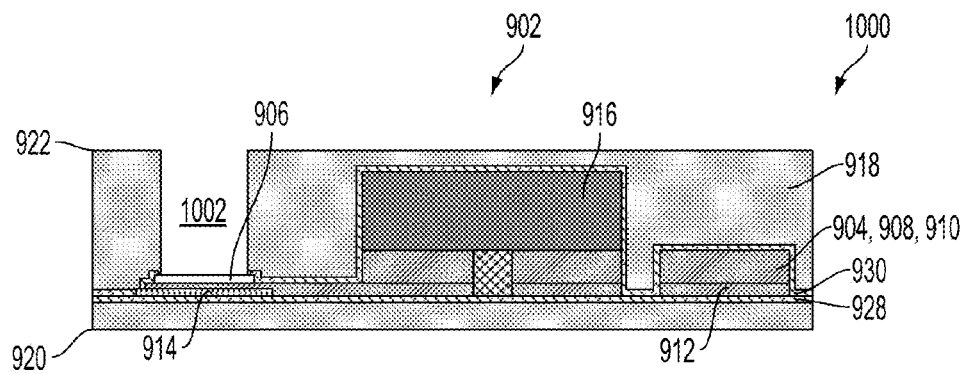
FIG. 10 show another bio-compatible device, according to an example embodiment.

FIG. 10 illustrates another bio-compatible device 1000, according to an example embodiment. In particular, the bio-compatible device 1000 includes an opening 1002 in the bio-compatible layer 918. As shown in FIG. 10, the opening 1002 is located over the sensor electrodes 906. The sensor electrodes 906 may be configured to receive one or more analytes via the opening 1002.

Moreover, as shown in FIG. 10, the bio-compatible device 1000 includes the conductive pattern 902, the antenna 904, the electrical interconnects 910, the electrical interconnects 912, the etch stop 914, the electronic component 916, the first side 920 of the bio-compatible device, the second side 922 of the bio-compatible device, the first coating 928, and the second coating 930.

The arrangement of the conductive pattern 902, the antenna 904, the sensor electrodes 906, the electrical contacts 908, the electrical interconnects 910, the electrical interconnects 912, the etch stop 914, the electronic component 916, the bio-compatible layer 918, the first side 920 of the bio-compatible device, the second side 922 of the bio-compatible device, the first coating 928, and the second coating 930 in the bio-compatible device 1000 may be the same as or similar to the arrangement of the conductive pattern 902, the antenna 904, the sensor electrodes 906, the electrical contacts 908, the electrical interconnects 910, the electrical interconnects 912, the etch stop 914, the electronic component 916, the bio-compatible layer 918, the first side 920 of the bio-compatible device, the second side 922 of the bio-compatible device, the first coating 928, and the second coating 930 in the device 900.

Figure 11:
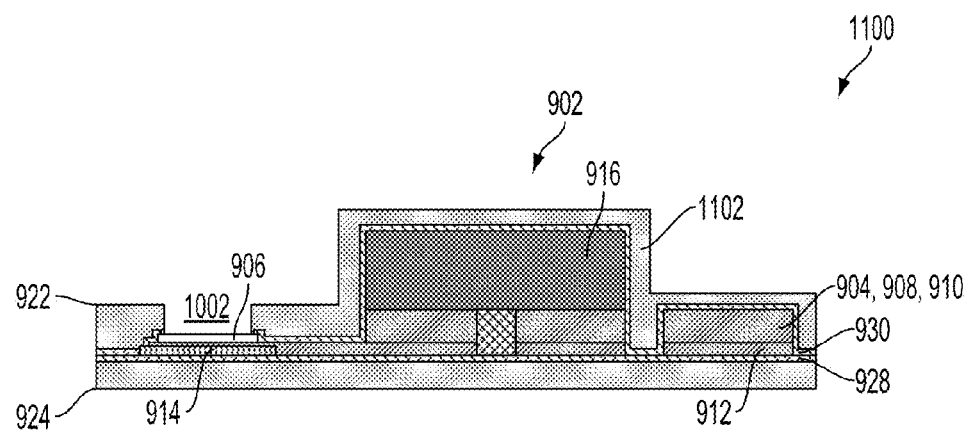
FIG. 11 shows another bio-compatible device, according to an example embodiment.

FIG. 11 illustrates another bio-compatible device 1100, according to an example embodiment. In particular, the bio-compatible device 1100 includes a bio-compatible layer 1102. In the bio-compatible device 1100, the opening 1002 is in the bio-compatible layer 1102.

As shown in FIG. 11, the bio-compatible device 1100 includes the conductive pattern 902, the antenna 904, the sensor electrodes 906, the electrical contacts 908, the electrical interconnects 910, the electrical interconnects 912, the etch stop 914, the electronic component 916, the first side 920 of the bio-compatible device, the second side 922 of the bio-compatible device, the first coating 928, and the second coating 930. Moreover, as shown in FIG. 11, the bio-compatible layer 1102 may include a conformal coat over conductive pattern 902, the antenna 904, the electrical contacts 908, the electrical interconnects 910, the electrical interconnects 912. The bio-compatible layer 1102 may be similar in form to the bio-compatible layer 918.

The arrangement of the conductive pattern 902, the antenna 904, the sensor electrodes 906, the electrical contacts 908, the electrical interconnects 910, the electrical interconnects 912, the etch stop 914, the electronic component 916, the bio-compatible layer 1102, the first side 920 of the bio-compatible device, the second side 922 of the bio-compatible device, the first coating 928, the second coating 930, and the opening 902 in the bio-compatible device 1100 may be the same as or similar to the arrangement of the conductive pattern 902, the antenna 904, the sensor electrodes 906, the electrical contacts 908, the electrical interconnects 910, the electrical interconnects 912, the etch stop 914, the electronic component 916, the bio-compatible layer 918, the first side 920 of the bio-compatible device, the second side 922 of the bio-compatible device, the first coating 928, the second coating 930, and the opening 1002 in the bio-compatible device 1000.

Figure 12:
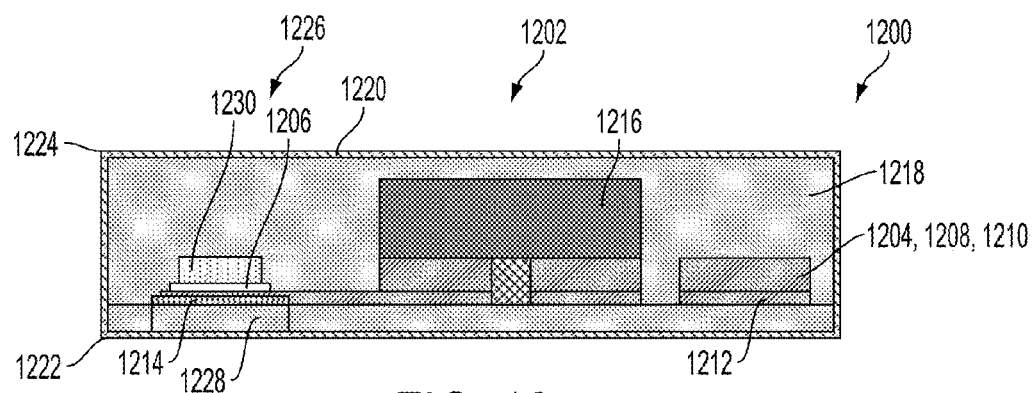
FIG. 12 shows another device, according to an example embodiment.

FIG. 12 illustrates another device 1200, according to an example embodiment. In particular, the device 1200 includes a conductive pattern 1202. The conductive pattern 1202 defines an antenna 1204, sensor electrodes 1206, electrical contacts 1208, electrical interconnects 1210, and electrical interconnects 1212. In addition, the device 1200 includes an etch stop 1214. As shown in FIG. 12, the sensor electrodes 1206 are located over the etch stop 1214.

Moreover, the device 1200 further includes an electronic component 1216 that is mounted to electrical contacts 1208. Further, the device 1200 further includes a bio-compatible layer 1218 over the electronic component 1216, the antenna 1204, the sensor electrodes 1206, the electrical contacts 1208, the electrical interconnects 1210, the electrical interconnects 1212, and the etch stop 1214.

In another aspect, the device 1200 may include a coating 1220 on the bio-compatible layer 1218. In some embodiments, the coating 1220 may surround the bio-compatible layer 1218. And in at least one such embodiment, the coating 1220 may define a first side 1222 and a second side 1224 of a bio-compatible device.

In another aspect, a first portion 1226 of the coating 1220 (and a portion of the bio-compatible layer 1218 under the first portion 1226) may be configured to be etched by an etchant to form an opening and thereby expose the sensor electrodes 1206. In some embodiments, the etch stop 1214 may configured to inhibit etching of a second portion 1228 of the coating 1220 (and a portion of the bio-compatible layer 1218 over the second portion 1228) by the etchant. As shown in FIG. 12, the etch stop 1214 is located over the second portion 1228 of the coating 1220.

The first portion 1226 of the coating 1220 (and the portion of the bio-compatible layer 1218 under the first portion 1226) may be configured to be etched the same or similar way as the first portion 624 of the bio-compatible layer 618 may be configured to be etched as described with reference to FIG. 6. Moreover, the etch stop 1214 may be configured to inhibit etching of the second portion 1228 of the coating 1220 (and the portion of the bio-compatible layer 1218 over the second portion 1228) the same or similar way as the etch 614 may be configured to inhibit etching of the second portion 626 of the bio-compatible layer 618 as described with reference to FIG. 6.

In yet another aspect, the device 1200 may further include a mask 1230. As shown in FIG. 12, the mask 1230 is located over the sensor electrodes 1206. In some embodiments, the mask 1230 may be configured to be removed when the portion 1220 (and the portion of the bio-compatible layer 1218 under the first portion 1226) is etched.

In some embodiments, the conductive pattern 1202 may take the form of or be similar in form to the conductive pattern 360, the antenna 1204 may take the form of or be similar in form to the antenna 346, the sensor electrodes 1206 may take the form of or be similar in form to the sensor electrodes 336, the electrical contacts 1208 may take the form of or be similar in form to the electrical contacts 348, the electrical interconnects 1210 may take the form of or be similar in form to the electrical interconnects 350, the electrical interconnects 1212 may take the form of or be similar in form to the electrical interconnects 358, the etch stop 1214 may take the form of or be similar in form to the etch stop 420, the electronic component 1216 may take the form of or be similar in form to the electronic component 364, the bio-compatible layer 1218 may take the form of or be similar in form to the first bio-compatible layer 308 and the second bio-compatible layer 478, the coating 1220 may take the form or be similar in form to the coating 502 and the mask 1230 may take the form of or be similar in form to the fifth mask 370.

Figure 13:
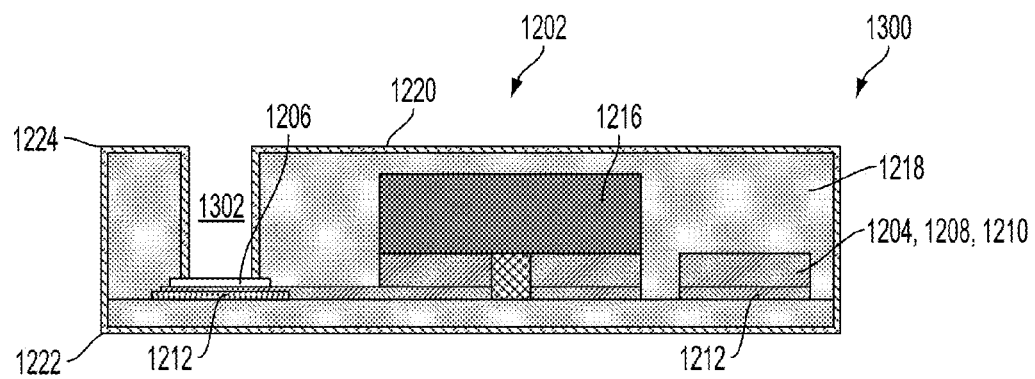
FIG. 13 shows another bio-compatible device, according to an example embodiment.

FIG. 13 illustrates another bio-compatible device 1300, according to an example embodiment. In particular, the bio-compatible device 1300 includes an opening 1302 in the coating 1220 and bio-compatible layer 1218. As shown in FIG. 13, the opening 1302 is located over the sensor electrodes 1206. The sensor electrodes 1206 may be configured to receive one or more analytes via the opening 1302.

Moreover, as shown in FIG. 13, the bio-compatible device 1300 includes the conductive pattern 1202, the antenna 1204, the electrical contacts 1208, the electrical interconnects 1210, the electrical interconnects 1212, the etch stop 1214, the electronic component 1216, the first side 1222 of the bio-compatible device, and the second side 1224 of the bio-compatible device.

The arrangement of the conductive pattern 1202, the antenna 1204, the sensor electrodes 1206, the electrical contacts 1208, the electrical interconnects 1210, the electrical interconnects 1212, the etch stop 1214, the electronic component 1216, the bio-compatible layer 1218, the coating 1220, the first side 1222 of the bio-compatible device, and the second side 1224 of the bio-compatible device in the bio-compatible device 1300 may be the same as or similar to the arrangement of the conductive pattern 1202, the antenna 1204, the sensor electrodes 1206, the electrical contacts 1208, the electrical interconnects 1210, the electrical interconnects 1212, the etch stop 1214, the electronic component 1216, the bio-compatible layer 1218, the coating 1220, the first side 1220 of the bio-compatible device, and the second side 1222 of the bio-compatible device in the device 1200.

Although example devices and bio-compatible devices have been described above with reference to FIGS. 6-13, other devices and bio-compatible devices are possible as well. For instance, a device may include a coating, such as the coating 1220, formed on a bio-compatible layer that takes the form of or be similar in form to the bio-compatible layer 618. Such a device may be similar in form to the device 600, except that such a bio-compatible device may not include the first coating 628 and/or the second coating 630. In such a device, for example, a portion of the bio-compatible layer may be located between the etch stop and the conductive pattern. The portion of the bio-compatible layer may be configured to insulate the etch stop so as to reduce shorting of the conductive pattern.

Further, a bio-compatible device may include a coating, such as the coating 1220, formed on at least a portion of a bio-compatible that takes the form of or be similar in form to the bio-compatible layer 618. Such a device may be similar in form to the bio-compatible device 700 and/or the bio-compatible device 800, except that such a bio-compatible device may not include the first coating 628 and/or the second coating 630. In such a device, for example, a portion of the bio-compatible layer may be located between the etch stop and the conductive pattern. The portion of the bio-compatible layer may be configured to insulate the etch stop so as to reduce shorting of the conductive pattern.

Further still, a device may include a coating, such as the coating 1220, formed on at least a portion of a bio-compatible layer that includes a conformal coat over a conductive pattern. Moreover, a bio-compatible device may include a coating, such as the coating 1220, formed on at least a portion of a bio-compatible layer that includes a conformal coat over a conductive pattern.

Like the bio-compatible device 300t, each of the other bio-compatible devices described above may be embedded in an eye-mountable device or may be mounted in other parts of the body, such as the skin, a tooth, or a tissue in the mouth.

Figure 14:
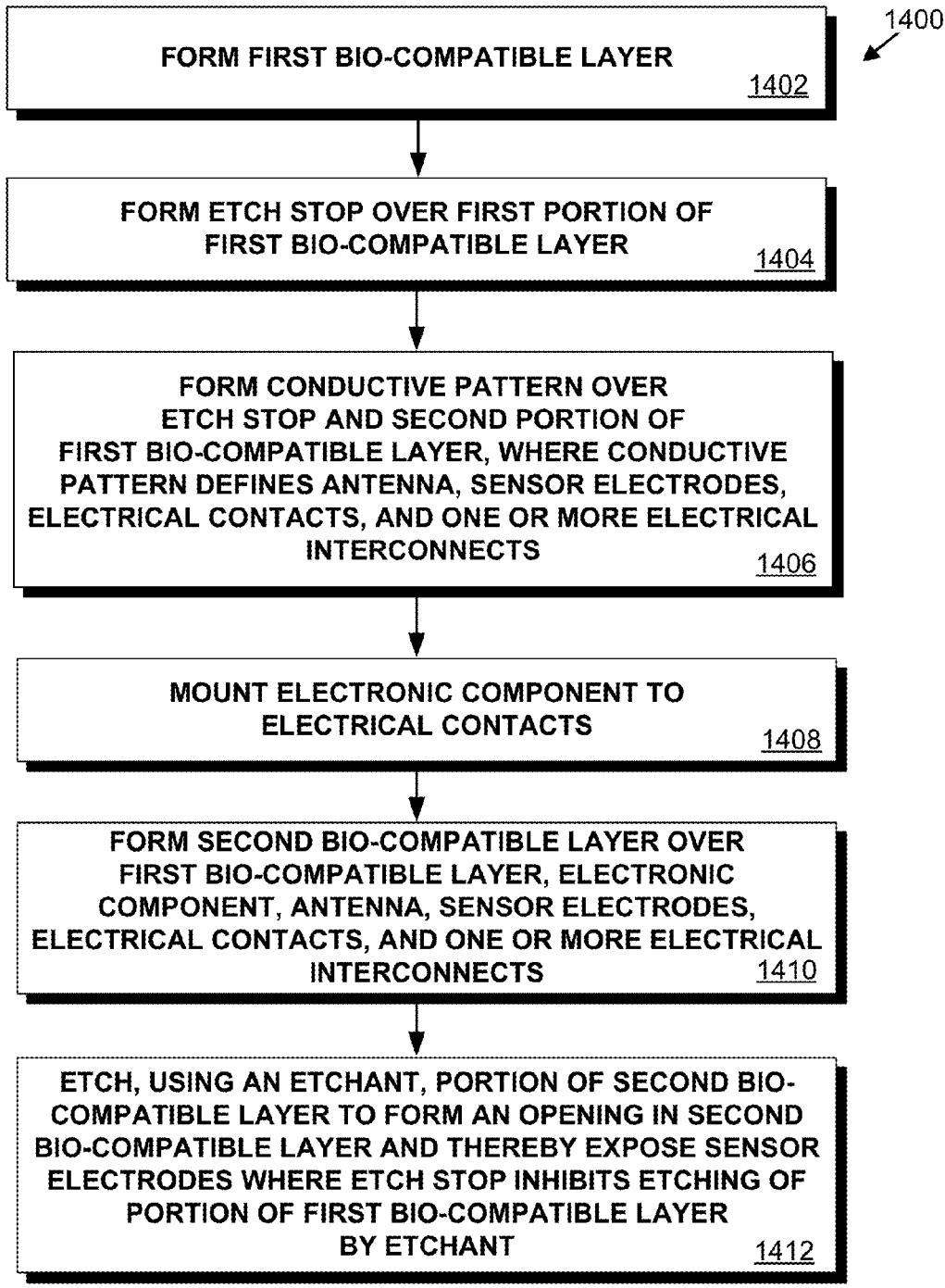
FIG. 14 is a flow chart illustrating a method for fabricating a bio-compatible device, according to an example embodiment.

FIG. 14 is a flowchart of a method 1400 for fabricating a bio-compatible device, according to an example embodiment. The method 1400 may involve forming a first bio-compatible layer (block 1402). The first bio-compatible layer defines a first side of a bio-compatible device. The first bio-compatible layer may be the same as or similar to the first bio-compatible layer 308. Moreover, the first bio-compatible layer may be formed the same or similar way as the first bio-compatible layer 308 may be formed as described with reference to FIG. 3b.

The method 1400 may involve forming an etch stop over a portion of the first bio-compatible layer (block 1404). The etch stop may be the same as or similar to the etch 320, the etch stop 420, the etch stop 614, the etch stop 914, and/or the etch stop 1214. In addition, the portion of the bio-compatible layer may be the same as or similar to the first portion 323 of the first bio-compatible layer 308. Moreover, the etch stop may be formed the same or similar way as the etch stop 320 may be formed as described with reference to FIG. 3e.

For instance, in some embodiments, the etch stop may have a dimension between 1 to 500 nanometers. Moreover, in some embodiments, the etch stop may comprise one or more non-conductive materials selected from the group consisting of silicon oxide, silicon nitride, and aluminum oxide. Further, in some embodiments, the etch stop may comprise one or more metals selected from the group consisting of aluminum, titanium, nickel, and chromium.

The method 1400 may involve forming a conductive pattern over the etch stop and the first bio-compatible layer (block 1406). The conductive pattern may define the antenna, sensor electrodes, electrical contacts, and one or more electrical interconnects. The conductive pattern may be the same as or similar to the conductive pattern 360, the conductive pattern 602, the conductive pattern 902, and/or the conductive pattern 1202; the antenna may be the same as or similar to the antenna 346, the antenna 604, the antenna 904, and/or the antenna 1204; the sensor electrodes may be the same as or similar to the sensor electrodes 336, the sensor electrodes 606, the sensor electrodes 906, and/or the sensor electrodes 1206; the electrical contacts may be same as or similar to the electrical contacts 348, the electrical contacts 608, the electrical contacts 908, the electrical contacts 1208; and the one or more electrical interconnects may be the same as or similar to the electrical interconnects 350, the electrical interconnects 610, the electrical interconnects 910, and/or the electrical interconnects 1210.

The method 1400 may involve mounting an electronic component to the electrical contacts (block 1408). The electronic component may be the same as or similar to the electronic component 364, the electronic component 616, the electronic component 916, and/or the electronic component 1216. Moreover, the electronic component may be mounted the same or similar way as the electronic component 364 may be mounted as described with reference to FIG. 3n.

The method 1400 may involve forming a second bio-compatible layer over the first bio-compatible layer, the electronic component, the antenna, the sensor electrodes, the electrical contacts, and the one or more electrical interconnects (block 1410). The second bio-compatible layer defines a second side of the bio-compatible device. The second bio-compatible layer may be the same as or similar to the third bio-compatible layer 378 and/or the second bio-compatible layer 478. Moreover, the second bio-compatible layer may be formed the same or similar way as the third bio-compatible layer 378 may be formed as described with reference to FIG. 3q.

The method 1400 may involve etching, using an etchant, a portion of the second bio-compatible layer to form an opening in the second bio-compatible layer and thereby expose the sensor electrodes (block 1412). The etch stop inhibits etching of the portion of the first bio-compatible layer. Moreover, the portion of the second bio-compatible layer may be etched to form the opening in the second bio-compatible layer and thereby expose the sensor electrodes the same or similar way as the first portion 386A of the exposed portions 386 of the third bio-compatible layer 378 may be etched to form the opening 388 in the third bio-compatible layer 378 and thereby expose the sensor electrodes 336 as described with reference to FIG. 3s. Moreover, the etch stop may inhibit etching of the portion of the first bio-compatible layer the same or similar way as the etch stop 320 may inhibit etching of the first portion 323 of the first bio-compatible layer 308 as described with reference to FIGS. 3s and 3s-2.

The method 1400 may further involve forming a third bio-compatible layer over the etch stop and the first bio-compatible layer. The third bio-compatible layer may be the same as or similar to the second bio-compatible layer 322. Moreover, the third bio-compatible layer may be formed the same or similar way as the second bio-compatible layer 322 may be formed as described with reference to FIG. 3f. In some embodiments, forming the conductive pattern over the etch stop and the first bio-compatible layer may involve forming the conductive pattern on the third bio-compatible layer.

Moreover, method 1400 may further involve forming a first coating over part of or all of the first bio-compatible layer and forming a second coating on at least a portion of the electronic component, the antenna, the sensor electrodes, the electrical contacts, and the one or more electrical interconnects. The first coating may be the same as or similar to the first coating 314, the first coating 628, and/or the first coating 928. Moreover, the first coating may be formed the same or similar way as the first coating 314 may be formed as described with reference to FIG. 3c. In some embodiments, forming the etch stop over the first portion of the first bio-compatible layer may involve forming the etch stop on a portion of the first coating.

In addition, the second coating may be the same as or similar to the second coating 374, the second coating 630, and/or the second coating 930. Moreover, the second coating may be formed the same or similar way as the second coating 374 may be formed as described with reference to FIG. 3p. In some embodiments, forming the second bio-compatible layer over the electronic component, the antenna, the sensor electrodes, the electrical contacts, and the one or more electrical interconnects may involve forming the second bio-compatible layer on a portion of the second coating.

Further, in at least one such embodiment, forming the second coating over at least a portion of the electronic component, the antenna, the sensor electrodes, the electrical contacts, and the one or more electrical interconnects may involve forming a second portion of the second coating over the sensor electrodes; and etching, using an etchant, the portion of the second bio-compatible layer to form an opening in the second bio-compatible layer and thereby expose the sensor electrodes may involve etching the second portion of the second coating.

Further, the method 1400 may further involve forming a coating over at least a portion of the bio-compatible device. The coating may be the same as or similar to the coating 502 and/or the coating 1220. The coating may be formed the same or similar way as the coating 502 may be formed as described with reference to FIG. 5.

For instance, in some embodiments, the coating may comprise one or more inorganic material layers. And in at least one such embodiment, the one or more inorganic material layers may comprise one or more inorganic materials selected from the group consisting of aluminum oxide, silicon oxide, and silicon nitride. Moreover, in some embodiments, the coating may comprise one or more inorganic material layers and one or more polymer layers. Further, in some embodiments, the coating may have a thickness between 1 to 50 nanometers.

Further still, the method 1400 may further involve conforming the bio-compatible device to a curvature of a polymer, forming a coating over at least a portion of the bio-compatible device, and embedding the bio-compatible device in the polymer.

Moreover, the method 1400 may further involve forming a sacrificial layer on a carrier substrate, and removing the sacrificial layer to release the bio-compatible device from the carrier substrate. The sacrificial layer may be the same as or similar to the sacrificial layer 304. In addition, the carrier substrate may be the same as or similar to the carrier substrate 302. Moreover, the sacrificial layer may be formed the same or similar way as the sacrificial layer 304 may be formed as described with reference to FIG. 3a. Further, the sacrificial layer may be removed the same or similar way as the sacrificial layer 304 may be removed as described with reference to FIG. 3t.

Figure 15:
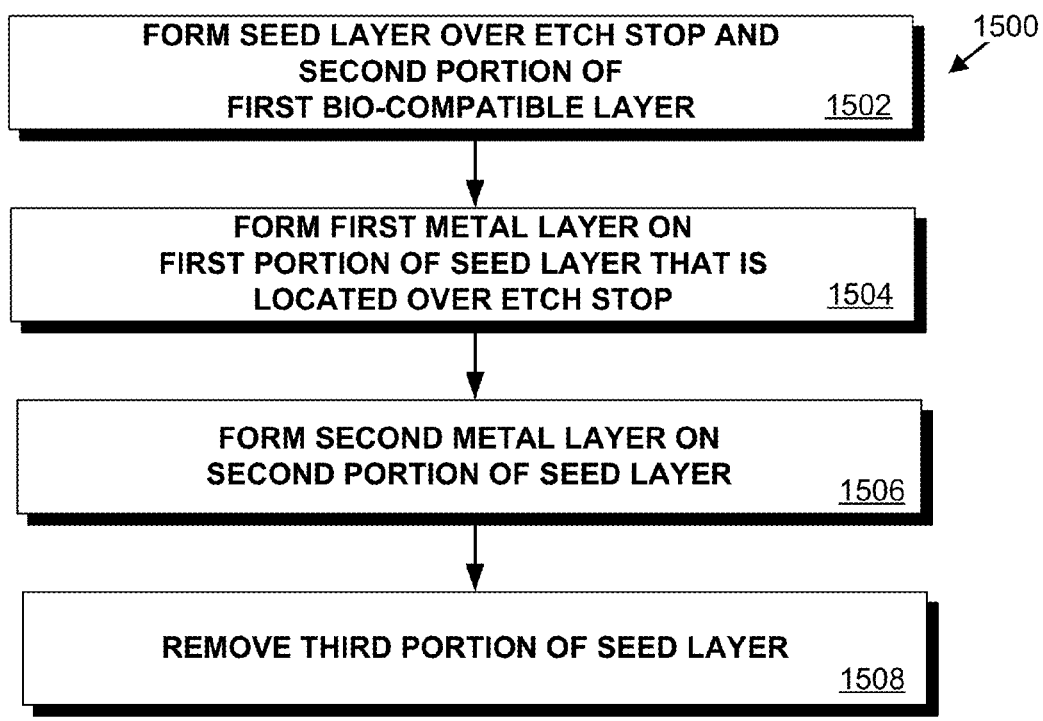
FIG. 15 is a flow chart illustrating a method for forming a conductive pattern, according to an example embodiment.

FIG. 15 is a flow chart illustrating a method 1500 for forming a conductive pattern, according to an example embodiment. The method 1500 may be performed in connection with block 1406 of method 1400. The method 1500 may involve forming a seed layer over the etch stop and the first bio-compatible layer (block 1502). The seed layer may be the same as or similar to the seed layer 326. Moreover, the seed layer 326 may be formed the same or similar way as the seed layer 326 may be formed as described with reference to FIG. 3g and/or the seed layer 326 may be formed as described with reference to FIG. 4a.

The method 1500 may involve forming a first metal layer on a first portion of the seed layer that is located over the etch stop (block 1504). The first metal layer defines the sensor electrodes. The first metal layer may be the same as or similar to the first metal layer 332. In addition, the first portion of the seed layer may be the same as or similar to the exposed portion 334 of the seed layer 326. Moreover, the first metal layer may be formed the same or similar way as the first metal layer 334 may be formed as described with reference to FIG. 3*i*.

The method 1500 may involve forming a second metal layer on a second portion of the seed layer (block 1506). The second metal layer defines the antenna, the electrical contacts, and a first electrical interconnects. The first electrical interconnects may be the same as or similar to the electrical interconnects 350. The second metal layer may be the same as or similar to the second metal layer 342. In addition, the second portion of the seed layer may be the same as or similar to the exposed portion 344 of the seed layer 326. Moreover, the second metal layer may be formed the same or similar way as the second metal layer 342 may be formed as described with reference to FIG. 3*k*.

The method 1500 may involve removing a third portion of the seed layer (block 1508). Part of the remaining portions of the seed layer define a second electrical interconnects. The remaining portions of the seed layer may be the same as or similar to the portion 326B of the seed layer 326. In addition, the second electrical interconnects may be the same as or similar to the electrical interconnects 358. And, the third portion of the seed layer may be the same as or similar to the exposed portion 356 of the seed layer 326. Moreover, the third portion of the seed layer may be removed the same or similar way as the portion 356 of the seed layer 326 may be removed as described with reference to FIG. 3*m*.

Figure 16:
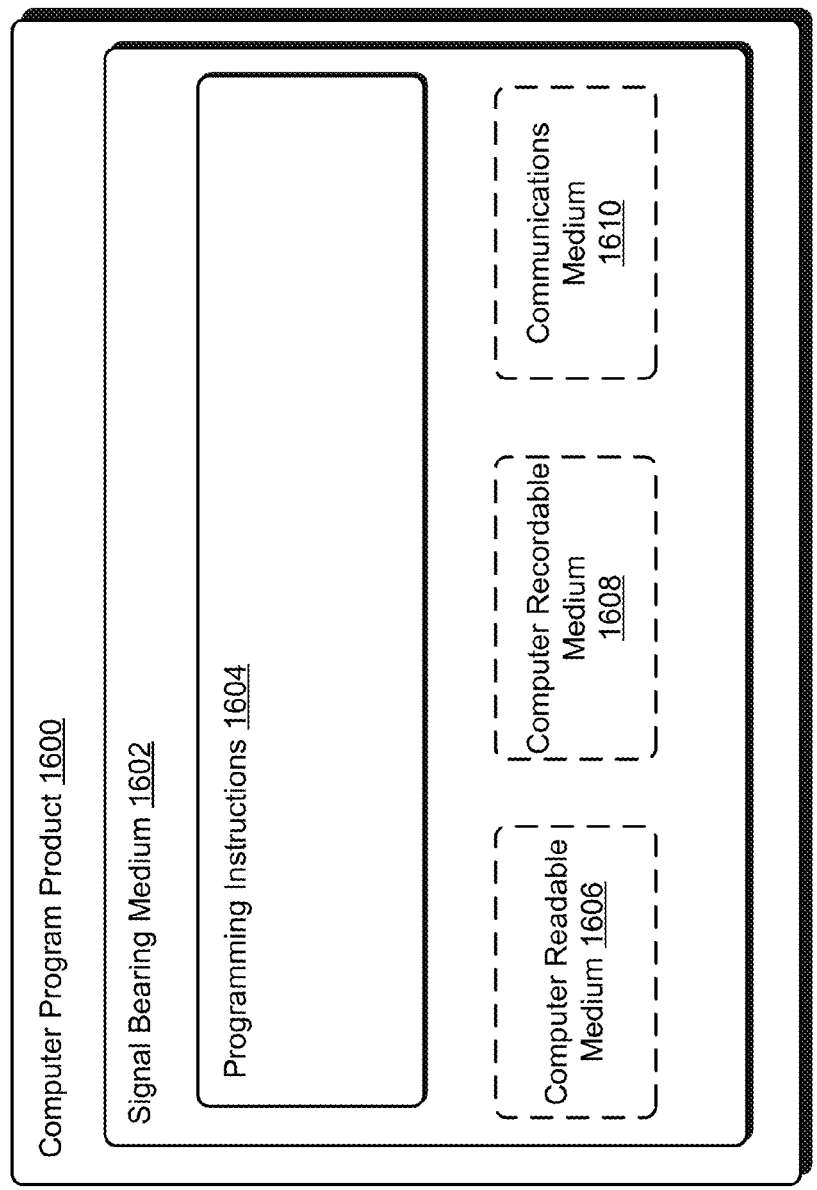
FIG. 16 depicts a computer-readable medium configured according to an example embodiment.

FIG. 16 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause a system to carry out the various functions, tasks, capabilities, etc., described above.

In some embodiments, the disclosed techniques can be implemented by computer program instructions encoded on a non-transitory computer-readable storage media in a machine-readable format, or on other non-transitory media or articles of manufacture. FIG. 16 is a schematic illustrating a conceptual partial view of a computer program product 1600 that includes a computer program for executing a computer process on a computing device, to perform any of the methods described herein.

In one embodiment, the computer program product 1600 is provided using a signal bearing medium 1602. The signal bearing medium 1602 may include one or more programming instructions 1604 that, when executed by one or more processors may provide functionality or portions of the functionality described above with respect to FIGS. 1-15. In some examples, the signal bearing medium 1602 can include a non-transitory computer-readable medium 1606, such as, but not limited to, a hard disk drive, a Compact Disc (CD), a Digital Video Disk (DVD), a digital tape, memory, etc. In some implementations, the signal bearing medium 1602 can be a computer recordable medium 1608, such as, but not limited to, memory, read/write (R/W) CDs, R/W DVDs, etc. In some implementations, the signal bearing medium 1602 can be a communications medium 1610, such as, but not limited to, a digital and/or an analog communication medium (e.g., a fiber optic cable, a waveguide, a wired communications link, a wireless communication link, etc.). Thus, for example, the signal bearing medium 1602 can be conveyed by a wireless form of the communications medium 1610.

The one or more programming instructions 1604 can be, for example, computer executable and/or logic implemented instructions. In some examples, a computing device is configured to provide various operations, functions, or actions in response to the programming instructions 1604 conveyed to the computing device by one or more of the computer readable medium 1606, the computer recordable medium 1608, and/or the communications medium 1610.

The non-transitory computer readable medium 1606 can also be distributed among multiple data storage elements, which could be remotely located from each other. The computing device that executes some or all of the stored instructions can be a microfabrication controller, or another computing platform. Alternatively, the computing device that executes some or all of the stored instructions could be remotely located computer system, such as a server.

IV. Conclusion

It should be understood that arrangements described herein are for purposes of example only. As such, those skilled in the art will appreciate that other arrangements and other elements (e.g., machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A method comprising:
   forming a first bio-compatible layer, wherein the first bio-compatible layer defines a first side of a bio-compatible device;
   forming an etch stop over a portion of the first bio-compatible layer;
   forming a conductive pattern over the etch stop and the first bio-compatible layer, wherein the conductive pattern defines an antenna, a sensor, electrical contacts, and one or more electrical interconnects;
   mounting an electronic component to the electrical contacts;
   forming a second bio-compatible layer over the first bio-compatible layer, the electronic component, the antenna, the sensor, the electrical contacts, the one or more electrical interconnects, and the etch stop, wherein the second bio-compatible layer defines a second side of the bio-compatible device; and
   etching, using an etchant, a portion of the second bio-compatible layer to form an opening in the second bio-compatible layer and thereby expose the sensor, wherein the etch stop inhibits etching of the portion of the first bio-compatible layer by the etchant.

2. The method of claim 1, wherein the etch stop has a dimension between 1 to 500 nanometers.

3. The method of claim 1, wherein the etch stop comprises one or more non-conductive materials selected from the group consisting of silicon oxide, silicon nitride, and aluminum oxide.

4. The method of claim 1, wherein the etch stop comprises one or more metals selected from the group consisting of aluminum, titanium, nickel, and chromium.

5. The method of claim 1 further comprising:
   forming a third bio-compatible layer over the etch stop and the first bio-compatible layer, wherein forming the conductive pattern over the etch stop and the first bio-compatible layer comprises forming the conductive pattern on the third bio-compatible layer.

6. The method of claim 1 further comprising:
   forming a coating over at least a portion of the bio-compatible device.

7. The method of claim 6, wherein the coating comprises one or more inorganic material layers.

8. The method of claim 7, wherein the one or more inorganic material layers comprise one or more inorganic materials selected from the group consisting of aluminum oxide, silicon oxide, and silicon nitride.

9. The method of claim 6, wherein the coating comprises one or more inorganic material layers and one or more polymer layers.

10. The method of claim 6, wherein the coating has a thickness between 1 to 50 nanometers.

11. The method of claim 1, further comprising:
    conforming the bio-compatible device to a curvature of a polymer;
    forming a coating over at least a portion of the bio-compatible device; and
    embedding the coated bio-compatible device in the polymer.

12. The method of claim 1 further comprising:
    forming a first coating over part of or all of the first bio-compatible layer, wherein forming the etch stop over the first portion of the first bio-compatible layer comprises forming the etch stop on a portion of the first coating; and
    forming a second coating on at least a portion of the electronic component, the antenna, the sensor, the electrical contacts, and the one or more electrical interconnects, wherein forming the second bio-compatible layer over the electronic component, the antenna, the sensor, the electrical contacts, and the one or more electrical interconnects comprises forming the second bio-compatible layer on a portion of the second coating.

13. The method of claim 12, wherein forming the second coating over at least the portion of the electronic component, the antenna, the sensor, the electrical contacts, and the one or more electrical interconnects comprises forming a second portion of the second coating over the sensor, and wherein etching, using the etchant, the portion of the second bio-compatible layer to form an opening in the second bio-compatible layer and thereby expose the sensor comprises etching the second portion of the second coating.

14. The method of claim 1 further comprising:
    forming a sacrificial layer on a carrier substrate, wherein the first bio-compatible layer is formed on the sacrificial layer; and
    removing the sacrificial layer to release the bio-compatible device from the carrier substrate.

15. The method of claim 1, wherein forming the conductive pattern over the etch stop and the second portion of the first bio-compatible layer comprises:
    forming a seed layer over the etch stop and the first bio-compatible layer;
    forming a first metal layer on a first portion of the seed layer that is located over the etch stop, wherein the first metal layer defines the sensor;
    forming a second metal layer on a second portion of the seed layer, wherein the second metal layer defines the antenna, the electrical contacts, and a first electrical interconnects; and
    removing a third portion of the seed layer, wherein part of the remaining portions of the seed layer define a second electrical interconnects.

* * * * *